US012758676B2

(12) United States Patent
Dagger et al.

(10) Patent No.: US 12,758,676 B2
(45) **Date of Patent: *Oct. 13, 2026**

(54) POLYMER FOAM MATERIAL, DEVICE AND USE

(71) Applicant: Smith & Nephew PLC, Watford (GB)

(72) Inventors: Anthony Dagger, York (GB); Nicholas Fry, Pocklington (GB); Helene Anne Lecomte, York (GB); David Stephenson, Hull (GB); Matthew Wray, Hessle (GB)

(73) Assignee: Smith & Nephew PLC, Watford (GB)

( * ) Notice: Subject to any disclaimer, the term of this patent is extended or adjusted under 35 U.S.C. 154(b) by 121 days.

This patent is subject to a terminal disclaimer.

(21) Appl. No.: 18/224,901

(22) Filed: Jul. 21, 2023

(65) Prior Publication Data

US 2024/0024531 A1 Jan. 25, 2024

Related U.S. Application Data

(62) Division of application No. 16/630,339, filed as application No. PCT/EP2018/069018 on Jul. 12, 2018, now Pat. No. 11,730,854.

(30) Foreign Application Priority Data

Jul. 12, 2017 (GB) ..................................... 1711181

(51) Int. Cl.
*A61L 15/26* (2006.01)
*A61F 13/00* (2024.01)
(Continued)

(52) U.S. Cl.
CPC ........ *A61L 15/26* (2013.01); *A61F 13/00063* (2013.01); *A61F 13/01017* (2024.01);
(Continued)

(58) Field of Classification Search
CPC .......... A61F 13/00063; A61F 13/01017; A61F 13/01042; A61F 13/05; A61L 15/26;
(Continued)

(56) References Cited

U.S. PATENT DOCUMENTS 3,586,648 A * 6/1971 Sambeth ................ C08J 9/0061
521/905
3,969,498 A 7/1976 Catania et al.
(Continued)

FOREIGN PATENT DOCUMENTS

CA 2523365 A1 10/2004
CN 101862470 A 10/2010
(Continued)

OTHER PUBLICATIONS

BBC BITESITE, "Rates of Reaction," National 5 Chemistry Revision, Retrieved from the Internet: www.bbc.co.uk/bitesize/guides/zct4fcw/revision/4, accessed on Mar. 4, 2022, 36 pages.
(Continued)

*Primary Examiner* — Hai Vo
(74) *Attorney, Agent, or Firm* — Knobbe, Martens, Olson & Bear, LLP

(57) ABSTRACT

Flexible polyurethane (PU) material which comprises
- a flexible hydrophilic polyurethane foam porous matrix comprising two matrix faces and therebetween a structural matrix framework defining a network of cells, having a cell network surface and therein a network of pores and
- a powder charge comprising one or more additives loaded in said structural matrix framework
- wherein said material is a foamed polymer of a system comprising an isocyanate prepolymer or monomer phase and an aqueous phase, wherein said system comprises one or more slurry phases or solid concen- (Continued)

Manufacture of PU foam: isocyanate-slurry phase or solid concentrate or carrier liquid phase upstream of or at MH trates of said powder charge, or an insoluble portion thereof, as said isocyanate phase or part thereof and/or as said aqueous phase or part thereof and/or in a carrier liquid phase;

and/or comprising a powder charge of silver salt loaded in said structural matrix framework in a population of silver salt particles defined by particle size distribution about a mean particle size of greater than or equal to 1 micron, said material comprising silver salt in population of particles corresponding to silver salt comprised in powder charge pre-loading;

methods for manufacture thereof, systems for control thereof, devices containing said material and methods for treatment therewith and uses thereof.

17 Claims, 25 Drawing Sheets

(51) Int. Cl.

| | |
|---|---|
| ***A61F 13/01*** | (2024.01) |
| ***A61F 13/05*** | (2024.01) |
| ***A61L 15/42*** | (2006.01) |
| ***A61L 15/44*** | (2006.01) |
| ***A61L 15/60*** | (2006.01) |
| ***C08G 18/10*** | (2006.01) |
| ***C08G 18/48*** | (2006.01) |
| ***C08G 18/76*** | (2006.01) |
| ***C08J 9/00*** | (2006.01) |

(52) U.S. Cl.

CPC ........ *A61F 13/01042* (2024.01); *A61F 13/05* (2024.01); *A61L 15/425* (2013.01); *A61L 15/44* (2013.01); *A61L 15/60* (2013.01); *C08G 18/10* (2013.01); *C08G 18/4833* (2013.01); *C08G 18/7621* (2013.01); *C08J 9/0066* (2013.01); *A61L 2300/104* (2013.01); *A61L 2300/106* (2013.01); *A61L 2300/404* (2013.01); *C08G 2110/0008* (2021.01); *C08J 2205/06* (2013.01); *C08J 2207/10* (2013.01); *C08J 2375/08* (2013.01)

(58) Field of Classification Search

CPC ........ A61L 15/425; A61L 15/44; A61L 15/60; A61L 2300/104; A61L 2300/106; A61L 2300/404; C08G 18/10; C08G 18/4833; C08G 18/7621; C08G 2110/0008; C08G 2110/0083; C08J 2205/06; C08J 2207/10; C08J 2207/12; C08J 2375/04; C08J 2375/08; C08J 9/0066; C08K 2003/3045; C08K 2201/005; C08K 3/105; C08K 3/30; C08L 75/04

See application file for complete search history.

(56) References Cited

U.S. PATENT DOCUMENTS

| | | | | |
|---|---|---|---|---|
| 4,340,043 | A | 7/1982 | Seymour | |
| 4,559,050 | A | 12/1985 | Iskra | |
| 4,728,323 | A | 3/1988 | Matson | |
| 5,147,338 | A | 9/1992 | Lang et al. | |
| 6,271,277 | B1 * | 8/2001 | Bleys | C08G 18/10 521/137 |
| 6,488,670 | B1 | 12/2002 | Schild et al. | |
| 8,084,663 | B2 | 12/2011 | Watson, Jr. | |
| 8,263,100 | B2 | 9/2012 | Areskoug et al. | |
| 9,345,803 | B2 | 5/2016 | Bradford | |
| 9,877,872 | B2 | 1/2018 | Mumby et al. | |
| 11,730,852 | B2 * | 8/2023 | Brewster | A61L 15/20 424/443 |
| 11,730,854 | B2 * | 8/2023 | Dagger | A61L 15/26 604/369 |
| 12,064,523 | B2 * | 8/2024 | Brewster | A61L 15/20 |
| 12,083,232 | B2 * | 9/2024 | Dagger | A61F 13/00063 |
| 2004/0091677 | A1 | 5/2004 | Topolkaraev | |
| 2006/0127437 | A1 | 6/2006 | Kennedy et al. | |
| 2007/0122462 | A1 | 5/2007 | Chandra et al. | |
| 2007/0275043 | A1 | 11/2007 | Freeman et al. | |
| 2010/0055437 | A1 | 3/2010 | Fink et al. | |
| 2010/0196501 | A1 | 8/2010 | Areskoug et al. | |
| 2010/0260824 | A1 | 10/2010 | Shah et al. | |
| 2011/0144599 | A1 | 6/2011 | Croizat et al. | |
| 2012/0130332 | A1 | 5/2012 | Cotton et al. | |
| 2012/0177720 | A1 | 7/2012 | Patel et al. | |
| 2012/0322903 | A1 | 12/2012 | Karandikar et al. | |
| 2014/0107555 | A1 | 4/2014 | Patel | |
| 2014/0276491 | A1 | 9/2014 | Luckemeyer et al. | |
| 2014/0336557 | A1 | 11/2014 | Durdag et al. | |
| 2015/0044449 | A1 * | 2/2015 | Foss | C08J 3/128 428/221 |
| 2015/0119837 | A1 * | 4/2015 | Thompson, Jr. | A61F 13/53713 502/402 |
| 2015/0283287 | A1 | 10/2015 | Agarwal et al. | |
| 2016/0045635 | A1 | 2/2016 | Jayakody et al. | |
| 2016/0228909 | A1 | 8/2016 | Marduel | |
| 2017/0098818 | A1 | 4/2017 | Cheng et al. | |
| 2018/0125721 | A1 | 5/2018 | Hoggarth et al. | |
| 2019/0083675 | A1 | 3/2019 | Carr et al. | |
| 2022/0118151 | A1 | 4/2022 | Gardiner et al. | |

FOREIGN PATENT DOCUMENTS

| | | | |
|---|---|---|---|
| CN | 203576752 | U | 5/2014 |
| EP | 0059049 | A1 | 9/1982 |
| EP | 0065370 | A1 | 11/1982 |
| EP | 2653140 | B1 | 3/2015 |
| EP | 2833929 | B1 | 7/2016 |
| GB | 2145126 | A | 3/1985 |
| WO | WO-9636757 | A2 | 11/1996 |
| WO | WO-9636758 | A2 | 11/1996 |
| WO | WO-03055941 | A1 | 7/2003 |
| WO | WO-03097727 | A1 | 11/2003 |
| WO | WO-2014086186 | A1 | 6/2014 |
| WO | WO-2014140608 | A1 | 9/2014 |
| WO | WO-2018115453 | A1 | 6/2018 |
| WO | WO-2019012068 | A1 | 1/2019 |
| WO | WO-2019012069 | A1 | 1/2019 |
| WO | WO-2019012072 | A1 | 1/2019 |

OTHER PUBLICATIONS

Hu J., "Practical Hospital Pharmacy 2nd Edition," 2007, 7 pages.

International Preliminary Report on Patentability for Application No. PCT/EP2018/069018, mailed on Jan. 23, 2020, 7 pages.

International Search Report and Written Opinion, for Application No. PCT/EP2018/069018, mailed on Oct. 25, 2018, 8 pages.

Mao L., "Medicinal Aerosols," 1996, 8 pages.

Office Action and Search Report mailed Jan. 17, 2018 for Great Britain Application No. 1711181.6, 3 pages.

"Pharmacopoeia of the People's Republic of China," compiled by the Pharmacopoeia Committee of the Ministry of Health of the People's Republic of China, 1995, p. 1120.

Woo K.Y., et al., "A Randomized Controlled Trial to Evaluate an Antimicrobial Dressing with Silver Alginate Powder for the Management of Chronic Wounds," Advances in Skin and Wound Care, vol. 25, No. 11, Nov. 2012, pp. 503-508.

Zhao Y., "Key Technology about Traditional Chinese Medicine and Natural Product Extraction and Preparation," Chapter 16, Section 1, 2012, 7 pages.

* cited by examiner

Figure 1: Manufacture of PU foam: line up with recirculation
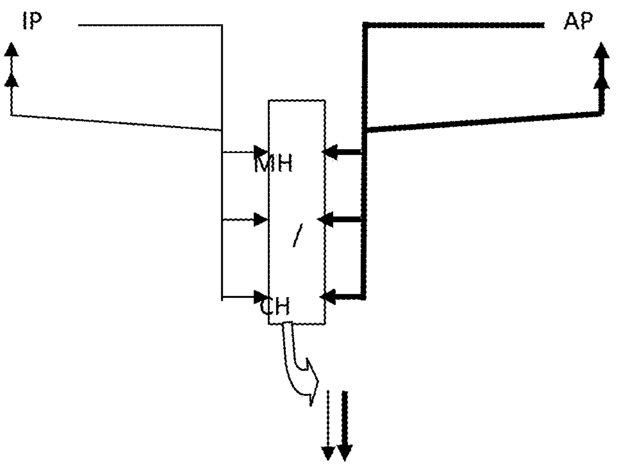
Figure 2a : Manufacture of PU foam: aqueous-slurry phase
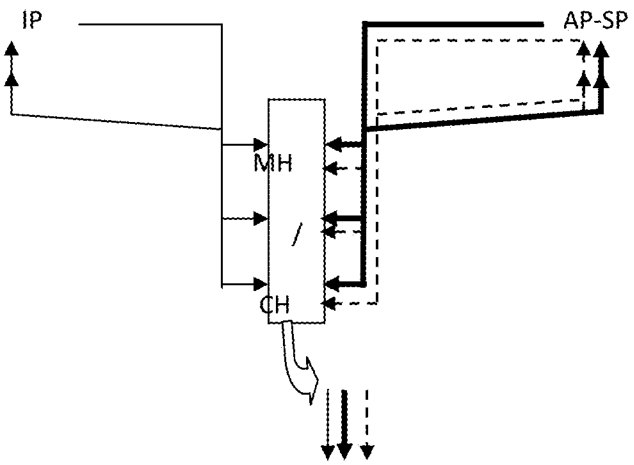
Figure 2b : Manufacture of PU foam: isocyanate-slurry phase
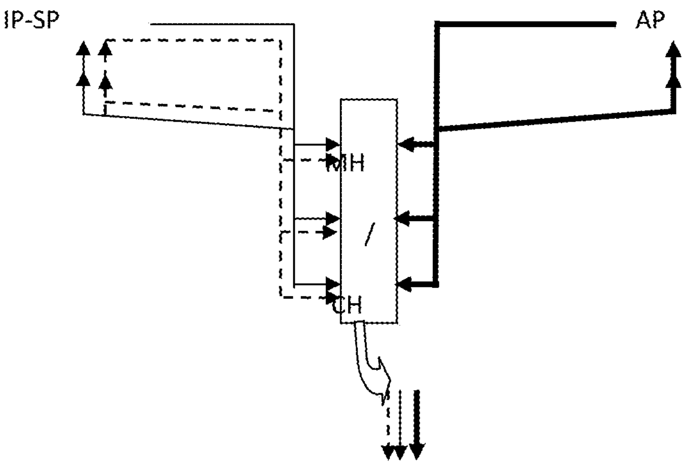

Figure 3a: Manufacture of PU foam: isocyanate-slurry phase or solid concentrate or carrier liquid phase upstream of or at MH
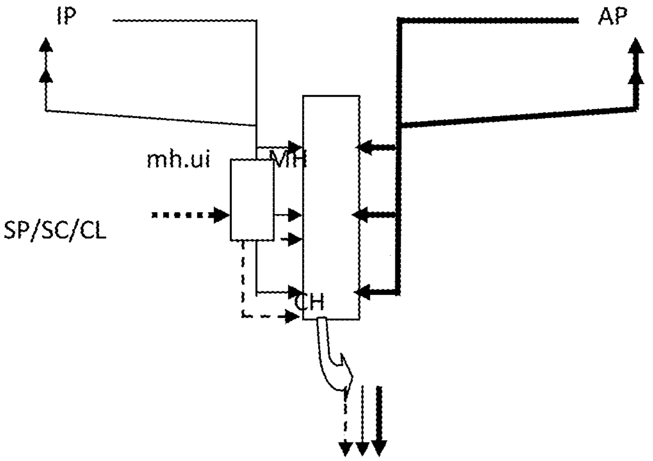
Figure 3b: Manufacture of PU foam: aqueous-slurry phase or solid concentrate or carrier liquid phase upstream of or at MH
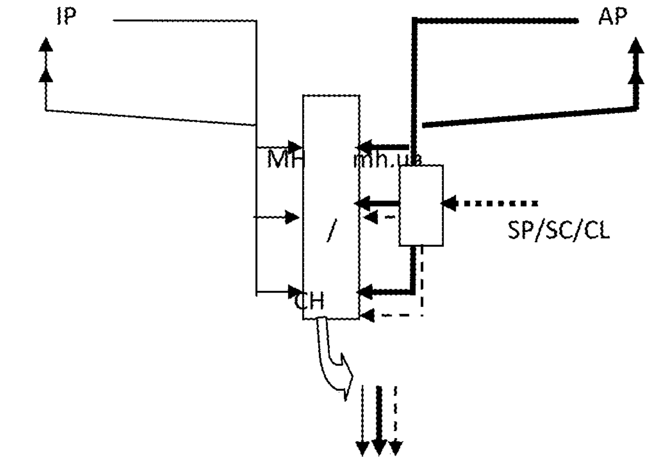

Fig. 4 P.O.M (aqueous) loaded PU foam (CE1.1)
a) 40-70micron
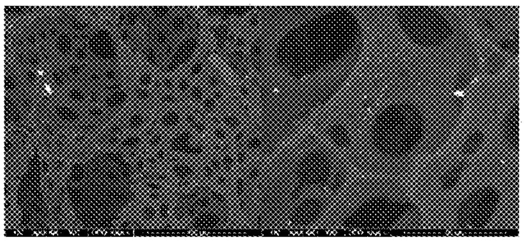
Fig. 5a – 5b P.O.M (isocyanate) loaded a) 6.7% b) 3.35%
a) 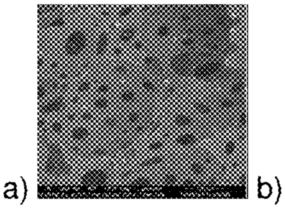 b) 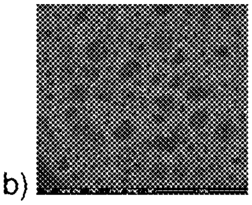
Fig. 6 P.O.M (isocyanate) loaded PU foam 7I
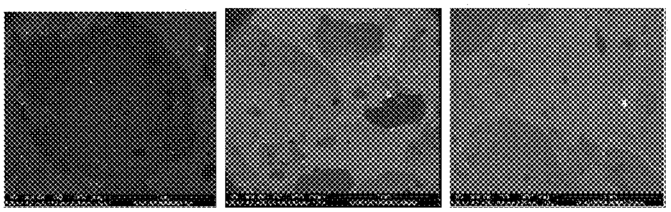

Wound dressing formats including P.O.M silver loaded PU foam material ('PU foam", "hydrocellular foam", 'foam")

POLYMER FOAM MATERIAL, DEVICE AND USE

CROSS-REFERENCE TO RELATED APPLICATIONS

This application is a divisional of U.S. application Ser. No. 16/630,339, filed Jan. 10, 2020, which is a U.S. national stage application of International Patent Application No. PCT/EP2018/069018, filed Jul. 12, 2018, which claims priority to U.K. Provisional Application No. 1711181.6 filed on Jul. 12, 2017, which is incorporated by reference in its entirety.

FIELD

This application discloses polyurethane (PU) foam materials and devices such as wound care materials and devices, methods for their manufacture, uses and methods of treatment therewith. The materials comprise additive loaded at point of manufacture of PU foam, with advantageous handling and dosing of additive and homogeneous distribution within said foam. Silver loaded materials and devices provide effective release of antimicrobial silver ion.

BACKGROUND

Reactive hydrophilic PU foam chemistry uses an "aqueous" phase which may include "surfactant" polyol, which reacts with an organic "isocyanate" phase of a prepolymer or monomer containing isocyanate groups. In this chemistry system, certain foam additives have been mixed, dissolved or dispersed in the aqueous or polyol phase, in a large scale process.

For example antimicrobial wound dressings often contain silver salts as the antimicrobial additive, combined with an absorbent foam which handles the exudate coming from the wound. Silver salts have been combined into porous foam via a liquid phase solution or suspension, and in the case of polyurethane foam this can be at the time of manufacture of the absorbent foam itself, where the silver salt is dissolved or (at higher concentrations) part dissolved and part suspended in the aqueous phase of the polymerisation reaction.

However, these show limitations on the quantity of silver salt that can be introduced (solubility limit or stability of the suspension), the type of salt being used (solubility in the liquid phase, density, degradation or reaction during the loading process), or the physical characteristics of the silver salt (poor control on the particle size created from solution or suspension), all of which can affect the antimicrobial performance of the wound dressing.

In particular, where additives have a high density and/or poor solubility in water, the process required to evenly distribute a suspension is complex, as the dense or poorly soluble salt will tend to precipitate rapidly. This also limits the maximum dose of such an additive that can be added, before it settles too readily in the process equipment, necessitating the aid of constant agitation in the polyol or aqueous phase.

Hitherto, fillers or additives have not been added to the isocyanate phase, because of the further compounded complexities with evenly distributing a suspension, and the risk of starting the self-polymerisation of the isocyanate phase, while the mixture is recirculating in the processing equipment. This would be problematic, as the viscosity of the phase will increase, potentially seizing up the equipment.

SUMMARY

We have now found that additive may be introduced to advantageous effect as a solid at point of PU manufacture by means of a slurry phase or solid concentrate as part of or additional to the isocyanate phase and/or aqueous phase and/or an inert fluid carrier phase.

For example additive, such as silver salt advantageous for PU foam-based wound dressings, is mixed into a part of the isocyanate phase of a reactive PU foam-forming system, to a concentration suitable for achieving the desired effect such as antimicrobial effect in the finished foam material. Surprisingly, the viscosity of the resulting isocyanate-additive slurry or solid concentrate remains pumpable, and the slurry or solid concentrate is stable over 3 months, with little or no increase in the viscosity thereof after the initial viscosity increase due to presence of additive. Said additive may likewise be provided in high concentration as a slurry or solid concentrate in aqueous phase or in inert organic or aqueous fluid carrier phase.

We provide herein PU foam material comprising additive, including very dense or poorly water-soluble additives, loaded in the foam, at the point of manufacture of said foam, without the problems of limited stability or solubility or maintaining an unstable suspension of solid in liquid.

More particularly, we provide herein PU foam material such as a wound dressing or a component thereof comprising additive, such as antimicrobial silver salt, including very dense or poorly water-soluble silver salt, loaded in the foam, by means of a stable slurry or solid concentrate of said salt, at the point of manufacture of said foam.

In embodiments there is provided herein flexible polyurethane (PU) material which comprises

- a flexible hydrophilic polyurethane foam porous matrix comprising two matrix faces and therebetween a structural matrix framework defining a network of cells, having a cell network surface and therein a network of pores and
- a powder charge comprising one or more additives loaded in said structural matrix framework
- wherein said material is a foamed polymer of a system comprising an isocyanate prepolymer or monomer phase and an aqueous phase, wherein said system comprises one or more slurry phases or solid concentrates of said powder charge, or an insoluble portion thereof, as said isocyanate phase or part thereof and/or as said aqueous phase or part thereof and/or in a carrier liquid phase.

Aqueous phase herein is any foam generating or initiating or inducing phase, as known in the art, and is selected from water and admixtures thereof with non-ionic surfactants.

Isocyanate phase herein comprises polymerisable isocyanate-terminated prepolymer or monomer, more particularly, isocyanate terminated prepolymer or monomer having functionality of more than 2, herein referred as isocyanate.

Carrier liquid herein may be organic or aqueous. Carrier liquid is preferably inert having regard to said additive. Carrier liquid may be inert having regard to the isocyanate phase and/or aqueous phase or may participate in the foaming reaction. Carrier liquid may be selected from a polymer or surfactant of same or similar type as the monomeric or prepolymeric backbone of said polymerisable isocyanate, or of said surfactant, for example differing in molecular weight, viscosity, or compatible backbone variants thereof. Carrier liquid may for example be selected from liquid polyols including polyethylene glycol (PEG), polypropylene glycol (PPG), polyether polyol, polyester polyol and the like.

In embodiments powder charge and additive comprised therein is insoluble or of very low solubility in said isocyanate phase and/or said carrier liquid and/or said aqueous phase. In an advantage powder charge and additive comprised therein may be readily soluble or of very low solubility in said aqueous phase but insoluble in said isocyanate phase or in carrier liquid, and comprised as a slurry phase or solid concentrate in said isocyanate phase or part thereof or in said carrier liquid. Powder charge and additive comprised in slurry phase or solid concentrate herein is provided in said system in a particular disposition of particles advantageous for additive performance, and is comprised in said material as solid-loaded additive, i.e. loaded as solid particles, thereby retaining pre-loading particle properties. For example silver salt retains particle properties advantageous for the release profile of silver ion, and additive such as particulate absorbent retains pre-loading absorbent capacity.

In embodiments there is provided herein flexible polyurethane (PU) material which comprises

- a flexible hydrophilic polyurethane porous foam matrix comprising two matrix faces and therebetween a structural matrix framework defining a network of cells, having a cell network surface and therein a network of pores and
- a powder charge of silver salt loaded in said structural matrix framework in a population of silver salt particles defined by particle size distribution about a mean particle size of greater than or equal to 1 micron.

Said material comprises silver salt in population of particles corresponding to silver salt comprised in powder charge pre-loading. Silver salt may be comprised in a single population having a single mean particle size or in plural populations having a plurality of mean particles sizes.

Powder charge of additive herein is solid-loaded in said structural matrix framework, i.e. comprises a powder charge of additive presented in powder form and comprised in said polyurethane foam material with retained powder form.

In embodiments polyurethane material comprises additive in homogeneous distribution as a function of stability and/or homogeneity of said slurry phase or solid concentrate.

Advantageously PU foam material herein comprises accurately dosed and/or homogeneously distributed additive. Additive or powder charge thereof, in slurry phase or solid concentrate, is maintained as a stable presentation of additive in liquid. An additive dose herein may be determined as a function of an amount of slurry phase or solid concentrate dosed to said system, i.e. to said isocyanate phase-aqueous phase system.

Preferably polyurethane material comprises additive in dose determined as a function of volume of said slurry phase or solid concentrate, or amount delivered in a given time for a given flow rate of said slurry phase or solid concentrate.

Yet more advantageously material herein comprises additive homogeneously distributed within said polyurethane phase as a function of homogeneity of both said slurry, as a stable suspension of powder in liquid, and said isocyanate phase-aqueous phase admixture. For example polyurethane foams produced from a silver salt-isocyanate slurry phase or solid concentrate mixed into an isocyanate phase reacted with an aqueous phase, display a good homogeneity of silver content throughout the foam, with a portion of the salt loaded in structural matrix framework at said matrix faces and cell network surface, and readily available for up-front contact by fluid at a locus, while another portion is embedded in the structural matrix framework, i.e. the polymer matrix.

Yet more advantageously, material herein comprises additive distributed within said structural matrix framework by means of said isocyanate-additive slurry or solid concentrate or organic carrier-additive slurry phase or solid concentrate, wherein additive retains particle form. For example, antimicrobial species-releasing additive such as silver salt retains species-releasing profile, such as silver ion-releasing profile, characteristic of additive powder provided in said powder charge, as a function of particle size and surface area thereof. Advantageously absorbent additive, such as SAP, retains aqueous absorption capacity characteristic of absorbent powder provided in said powder charge.

A flexible PU material, PU foam or PU matrix herein is both conformable and elastically extensible. Flexible material, foam or matrix herein may be conformed to a surface, such as a shaped-surface, for example irregular or regular, static or mobile. For example material, foam or matrix may be conformable to a surface of a body part or wound surface or the like and dynamically conform to changes resulting from movement, skin drag, stretch, flex and the like. Such material, foam or matrix may attain and retain a shape or profile with or without the aid of adhesive or other restraint.

A cell and cell network herein may be any interconnecting cell, void or free space and network thereof comprised in a polyurethane structural matrix framework. A pore and pore network herein includes any pore, cell-opening or cell window interconnecting adjacent cells, and network thereof. A pore and pore network herein permits fluid (liquid and gas) transmission between cells, and provides a fluid pathway.

A powder herein may take its ordinary meaning, and may be understood to denote fine, dry particle(s), including primary particles, and agglomerations and aggregates thereof, defined as secondary particles. Primary particles, are characterised by particle size or in case of a range of particle sizes, by particle size distribution.

Agglomerations and aggregates retain cumulative surface area of primary particles. An individual agglomeration or aggregate is thus typically of greater surface area than a corresponding size single primary particle.

Reference herein to a powder charge is to a charge of powder as delivered and comprised in the PU material, so as to confer characteristic powder properties on said material, that is to say retaining powder form throughout generation of said foam from delivery to provision within said polyurethane foam material. A powder charge delivered by means of a slurry phase or solid concentrate retains powder form throughout generation of said foam for the entire powder charge or an insoluble portion thereof.

A powder charge may be a non-quantitative charge or may be a quantitative charge. A powder charge may be a batch or discontinuous charge or a continuous charge, for example may be the total charge on or in a discontinuous PU foam material/structure such as a PU foam slab or PU foam pad, or may be a charge per unit volume or area on or in a continuous PU foam material/structure such as a roll thereof.

A powder charge herein is a charge of additive powder or a combination thereof, optionally together with other powders as processing aids.

Slurry herein takes the commonly accepted meaning thereof, typically a sloppy or viscous fluid mixture or “mud” of a pulverized solid with a liquid. Slurry phase herein is thus a sloppy, viscous mixture of additive powder charge in isocyanate phase or part thereof and/or aqueous phase or part thereof and/or organic carrier liquid as herein defined. Slurry herein behaves in some ways like a thick fluid, flowing under gravity and also capable of being pumped.

A solid concentrate herein is a suspension of insoluble or poorly soluble additive particles in a part of said isocyanate phase or a part of said aqueous phase or in an organic or aqueous carrier liquid phase provided in volume less than that of said isocyanate phase or of said aqueous phase respectively.

A slurry comprised in a part of said isocyanate phase or part of said aqueous phase or in said organic carrier liquid, or solid concentrate herein may be provided from a reservoir dosed to said system conferring operational benefits whereby a recirculating stream or line for either isocyanate or aqueous phase in a continuous manufacturing method need not be additive contaminated.

A slurry phase or solid concentrate herein therefore provides a convenient way of handling solid additive or powder charge in bulk.

Polyurethane material herein conveniently comprises additive or active component thereof in liquid as herein defined in an amount of from a trace amount up to 50 wt % or 99 wt %, more particularly from 0.3 wt % up to 20 wt % or 50 wt %, such as from 1 wt % or 2 wt % or 3.5 wt % up to 20 wt %, for example from 2 wt % to 15 wt %, or 3.35 wt % or 3.8 wt % to 10 wt %. Additive may be for example silver salt, and active component thereof elemental silver, indicated as total silver (TS) herein.

This compares with commercially available polyurethane foams such as Mepilex Ag which typically comprise additive such as silver sulfate in amount of about 2.25 wt % of total aqueous phase. This would compare to an amount in isocyanate of about 5.2 wt % of total isocyanate phase as herein. Materials and methods herein are therefore of particular advantage in providing elevated content of additive with the further processing advantages herein disclosed.

Silver salt is suitably comprised in material herein or assembled with matrix component herein in an amount of 0.05 mg to 3.5 mg or 0.05 mg to 4 mg silver ion/cm$^2$ of material as herein defined, such as 0.1 mg to 3.5 mg or 4 mg silver ion/cm$^2$ of material as herein defined or 0.2 mg to 3.5 mg or 4 mg silver ion/cm$^2$ material as herein defined. Material may comprise additive in amount at a face and/or in cell network in excess of 1.4 mg/cm$^2$ up to 4 mg/cm$^2$ such as in the range 1.75 mg/cm$^2$ to 3.5 mg/cm$^2$.

Antimicrobial additive is suitably characterised by species release profile, such as silver ion release profile, i.e. amount of species such as silver ion as hereinbefore defined released with time, such as amount released into 50 mL of aqueous media given as mg/cm$^2$ of material per unit time. In embodiments release profile is rapid onset, i.e. bolus release, within 24 hours, thereafter maintaining a sustained steady state secondary release for duration up to 10 days, for example up to 7 or 8 days.

In an advantage material herein comprises additive up to that amount for which slurry phase or solid concentrate viscosity is still such as to be pumpable and capable of being mixed in a system as hereinbefore defined.

Foam herein is suitably cross linked polyurethane foam. Favoured hydrophilic foams of this type include those known as Hypol foams, generated from favoured Hypol hydrophilic isocyanate prepolymers which are commercially available, for example marketed by W.R. Grace & Co.

Additive herein is suitably selected from one or more additives which modifies the structure or properties of said PU foam, for example its absorption or antimicrobial or other properties, more preferably modifies structure or properties of said PU foam as a wound care material, more particularly as a wound dressing material, such as its absorption of wound fluid and/or antimicrobial effect within said material and/or within a wound locus or other property thereof.

In embodiments an additive herein additive is selected from any one or more of antimicrobial additives and wound dressing additives including odour control, protein-breaking, enhanced wicking, colour or masking, conductive, structure-supporting or reinforcing, enhanced absorbency, aqueous absorber such as super absorbent polymer (SAP), prevention of PU foam yellowing (optical brighteners, oxidation prevention), activated charcoal, and combinations thereof and with other agents such as viscosity modifying agents and the like. Preferably an additive herein is an antimicrobial additive or a fluid absorbent and combinations thereof and with one or more colour control, odour control, conduction or reinforcing additives.

In embodiments antimicrobial additive herein is an antimicrobial release additive adapted to release antimicrobial into a locus, suitably an antimicrobial species-releasing additive adapted to release antimicrobial species into a locus wherein an antimicrobial species is selected from one or more or atomic species and one or more diatomic species. An antimicrobial species-releasing additive may be activated to release antimicrobial species as defined, by a release event comprising contact with moist or aqueous medium. Antimicrobial species-releasing additive or part thereof is therefore soluble or leaches into water, preferably has solubility in excess of 0.15 mg/L at 25° C. Material as herein defined is ideally stored away from moisture or aqueous medium, for example packaged in water impermeable packaging. Thereby premature release of antimicrobial species is avoided.

Atomic or diatomic species may be charged or uncharged. Antimicrobial atomic species herein is preferably antimicrobial ion, more preferably antimicrobial cation, most preferably silver cation. Antimicrobial diatomic species herein is suitably uncharged, more preferably is homonuclear diatomic species such as I2. Antimicrobial species-releasing additive is suitably selected from elemental silver, silver salt, silver complex and caged forms thereof and from caged forms of iodine and combinations thereof.

In embodiments absorbent herein is an absorbent polymer, preferably is a super absorbent polymer (SAP) preferably medical grade SAP.

Preferably there is provided herein a flexible polyurethane (PU) material a flexible hydrophilic polyurethane foam porous matrix comprising two matrix faces and therebetween a structural matrix framework defining a network of cells, having a cell network surface and therein a network of pores and a powder charge comprising one or more additives loaded in said structural matrix framework wherein said material is a foamed polymer of a system comprising an isocyanate phase and an aqueous phase, wherein said system comprises one or more slurry phases or solid concentrates of powder charge in said isocyanate phase or part thereof and/or said aqueous phase or part thereof and/or a carrier liquid wherein said additive is selected from antimicrobial species-releasing additive and absorbent additive and combinations thereof, wherein antimicrobial species-releasing additive and absorbent additive are selected from elemental silver, silver salt, silver complex, caged forms thereof, caged forms of iodine, super absorbent polymer and combinations thereof.

Preferred silver complexes and silver salts are selected from one or more of colloidal silver, silver zeolite, silver sulfadiazine, silver sulfate, silver carbonate, silver chloride, silver nitrate, silver oxide, silver phosphate, silver citrate, silver acetate, silver lactate, and combinations thereof. Preferably caged iodine is selected from cadexomer iodine.

Preferred super absorbent polymer is selected from sodium polyacrylate, cross linked carboxymethyl cellulose (CMC or other absorbent functionalised (by carboxylation or sulfonation) cellulose derivatives, cross linked polyethylene oxide and PVA copolymer.

Material herein may comprise a plurality of powder charges, comprising same or different additive, said charges may be provided in same or different slurry phases herein and have same or different dosing control and distribution throughout said structural matrix framework.

In a further aspect there is provided a method for manufacture of a flexible hydrophilic polyurethane foam porous matrix comprising two matrix faces and therebetween a structural matrix framework defining a network of cells, having a cell network surface and therein a network of pores and a powder charge comprising one or more additives loaded in said structural matrix framework said method comprising providing an isocyanate phase and an aqueous phase making up a foamable polymerisable system;

and providing one or more slurry phases or solid concentrates of said powder charge, or insoluble portion thereof, making up said isocyanate phase or part thereof and/or said aqueous phase or part thereof and/or in an inert carrier liquid phase; and intimately admixing said isocyanate phase and said aqueous phase with reaction and foaming thereof;

wherein in case that said slurry phase or solid concentrate makes up a part of one of said phases or makes up a carrier liquid phase, said method comprises prior to, simultaneously with or subsequent to admixing the other part thereof with the other phase thereof, or admixing said phases, combining said slurry phase or solid concentrate with the other part thereof or with one or both of said phases.

In embodiments there is further provided a method of manufacture of a polyurethane material as hereinbefore and hereinbelow defined.

Preferably said method comprises additionally shaping said material, for example by casting said mixed phases onto or into a liner, shaped liner or mould, prior to, simultaneously with or subsequent to foaming and reaction thereof, and drying said shaped foam.

Preferably said step of providing a slurry phase or solid concentrate comprises dosing powder charge to isocyanate phase or part thereof and/or aqueous fluid or part thereof and/or carrier fluid in sufficient quantity to generate a slurry or solid concentrate. In an advantage said slurry or solid concentrate exhibits homogeneous fluid behaviour. In a further advantage said slurry or solid concentrate is in additive concentration independent of additive solubility. In a further advantage a slurry or solid concentrate is stable.

In embodiments said slurry phase or solid concentrate comprises said isocyanate phase and/or said aqueous phase. In embodiments said method comprises providing powder charge in both isocyanate-additive slurry phase or solid concentrate and aqueous-additive slurry phase or solid concentrate. Powder charge and/or additive comprised therein may be same or different in respective slurry phases or solid concentrates.

In embodiments said slurry phase or solid concentrate comprises said additive in a part of said isocyanate phase and/or a part of said aqueous phase, in volume less than the total volume of said isocyanate phase or of said aqueous phase, preferably less than or equal to 60% of the volume thereof, for example 20%-50% of the volume thereof.

Continuous polyurethane foam manufacturing processes provide continuous flow and steady flow rate of isocyanate phase and aqueous phase in supply lines, and batchwise admixing at mixing head and casting at casting head, by provision of recirculation circuits for respective phases upstream of said mixing head. Recirculation circuits permit continuous flow in feed line to mixing head during dosing and in a circuit including feed line to a point upstream of mixing head, in between dosing at mixing head. Preferably said slurry or solid concentrate of powder charge in a part of said isocyanate phase and/or a part of said aqueous phase is provided intermittently to said mixing head or point upstream or downstream thereof without recirculation thereof or is provided in an independent recirculation circuit. Thereby a manufacturing process can be easily switched between manufacture of foams with different additives without contamination by residual additive in isocyanate or aqueous recirculation circuits.

In embodiments said method comprises providing isocyanate phase and/or aqueous phase in a primary, optionally recirculating, part and a secondary, optionally non-recirculating, slurry phase or solid concentrate part. Said method comprises combining said secondary slurry phase or solid concentrate part with said primary part or said admixed phases.

Aqueous-powder charge slurry phase or solid concentrate may be powder charge in water, in surfactant, optionally with non-aqueous diluent, or in aqueous surfactant. In case that aqueous-powder charge slurry phase or solid concentrate is powder charge in one of water or non-aqueous surfactant, said slurry phase or solid concentrate may be combined with the other thereof, thereby making up said aqueous surfactant phase, prior or simultaneously with or subsequent to admixing said phases.

In further embodiments said method comprises providing slurry phase or solid concentrate of powder charge in carrier liquid. Said method comprises combining said carrier-powder charge slurry phase or solid concentrate with said isocyanate phase, said aqueous phase or said admixed phases.

In accordance with established methods, isocyanate, preferably isocyanate-terminated polyol is typically absent from or present in incidental or insignificant amount in said aqueous phase, and water or aqueous surfactant is absent from or present in incidental or insignificant amount in said isocyanate phase.

Powder charge herein comprises additive herein which is commercially available and may be comprised as supplied in powder charge or may be processed, for example by drying, by particle size reduction such as selection of a desired particle size grade thereof, or by methods known in the art or novel methods herein.

In embodiments herein slurry phase or solid concentrate comprises powder charge characterised by weight loss on drying (L.O.D) less than 2%.

L.O.D is suitably determined in a sample of powder charge herein as weight loss during 4 hours in vacuum oven at 50° C. or in non-vacuum oven at 105° C., of less than 2%, such as less than 1% or of less than 0.5%, such as less than 0.4% or less than 0.3% or less than 0.2% or 0.1%.

L.O.D as defined permits accurate dosing of additive or powder charge thereof, without additional or variable moisture content in said dosed amount.

In embodiments slurry phase or solid concentrate comprises powder charge in isocyanate and is characterised by L.O.D less than 0.5% and permits mixing into reactive isocyanate phase herein with upheld stability of said phase, i.e. without initiating self-polymerisation thereof.

L.O.D may be determined as powder charge or additive. Alternatively L.O.D may be determined as material comprising additive and includes loss of moisture from the matrix and from the additive. Material humidity varies with atmospheric conditions and may be determined and decoupled in suitable manner.

It may be desired that additive is provided in only one slurry phase or solid concentrate herein. Unless otherwise indicated, powder charge or additive present in one of said isocyanate phase and said aqueous phase is absent from or present in incidental or insignificant amount in the other thereof.

In embodiments the method herein is discontinuous, comprising providing said isocyanate phase, aqueous phase and slurry phase or solid concentrate, where separate therefrom, in respective volumes and mixing thereof into or in a reaction and foaming vessel. Mixing means may be provided in said reaction and foaming vessel, in a dedicated mixing vessel or in one or more mixing heads leading into said reaction and foaming vessel. Said reaction and foaming vessel may provide shaping of said material, alternatively shaping may be on or in a dedicated liner or mould.

In embodiments the method herein is continuous as hereinbefore defined, comprising providing each of isocyanate phase, aqueous phase and slurry phase(s) or concentrate(s), where separate therefrom, in respective streams and within respective feed lines with mixing thereof as hereinbefore defined, in one or more mixing heads leading to a reaction and foaming unit such as a vessel or reaction line and/or a liner or mould for shaping thereof. Continuously providing a phase or concentrate herein is by known means for transporting, conveying or otherwise moving fluids such as pump. A slurry phase or solid concentrate may be provided in a line including agitating or mixing means such as sonic or static mixing elements and the like.

Preferably said method is continuous and comprises dosing slurry phase or solid concentrate to a 2-way mixing head with a stream of said isocyanate phase or part thereof, or said aqueous phase or part thereof and thence to a further 2-way mixing head with a stream of other said phase; or to a 2-way mixing head with a stream of said intimately admixed isocyanate phase or part thereof and aqueous phase or part thereof; or to a 3-way mixing head with respective streams of said isocyanate phase or part thereof and said aqueous phase or part thereof. Said mixing head may be a combined mixing and casting head or the method herein may comprise conveying said admixed phases from said mixing head or heads to a casting head.

Isocyanate phase and aqueous phase herein are known in the art and for example as detailed in EP0059049, the contents of which are incorporated herein by reference.

Isocyanate phase is suitably selected from Hypol isocyanate prepolymers including Hypol 2000, 2001, 3000, 3001, 2002 (for example herein PEG-TDI) and 2000HD, marketed by W.R Grace & Co. and other isocyanate-polyol prepolymers where the isocyanate is TDI or MDI and the polyol comprises a backbone selected from PEG, PPG and the like of varying molecular weight or chain length. Hypols are described in a booklet published by W.R Grace & Co. "Hypol: formable hydrophilic polymers-laboratory procedures and foam formulation". Their preparation and use are disclosed in British Patent Specifications No. 1,429,711 and 1,507,232.

Isocyanate-powder charge slurry phase or solid concentrate herein may comprise 100% of the total isocyanate phase, by volume, or may comprise an amount such as of 20%-60% or 80% by volume thereof, the remainder comprised in said isocyanate phase, for example a recirculating isocyanate phase herein.

Aqueous phase is suitably selected from water and admixtures thereof with surfactant selected from non-ionic surfactants for example selected from low molecular weight PEG, and oxypropylene-oxyethylene block copolymers known as Pluronic™ marketed by BASF Wyandotte. Preferred Pluronics include L64, F87, P38, P75, L65 and L62. Another favoured non-ionic surfactant is a polyoxyethylene stearyl ether known as Brij 72 marketed by Honeywell Atlas.

Aqueous-powder charge slurry phase or solid concentrate herein may comprise up to 93% or 100% of the total aqueous liquid, such as water or aqueous surfactant, by volume, or may comprise an amount such as of 20%-60% or 80% by volume thereof, the remainder comprised in said aqueous phase, for example a recirculating aqueous phase herein.

Slurry phase or solid concentrate may comprise solid content of 1.5%-50% by weight of additive in liquid. In an advantage slurry or concentrate herein is in concentration independent of additive solubility and may be in a concentration in excess of a solution saturation concentration thereof. A slurry phase herein may comprise solid content selected to give a desired homogeneous fluid flow behaviour, wherein slurry phase flow rate may be adjusted for a required additive loading in polyurethane material herein. A concentrate herein may comprise solid content as desired for a required additive loading, for example in higher solid content in case that low fluid volume is desirable or in lower solid content in case that high fluid volume is desirable.

Selection of slurry phase or concentrate may be dependent on a given additive, for example the density thereof.

In an advantage embodiments as hereinbefore and hereinbelow defined enable the use of dense (e.g. silver sulfate), sparingly water-soluble salts, without the need for liquid-phase processing or, with reduced solvent levels, reduced aqueous solvent content in finished foam or solvent recycle reducing solvent disposal concerns (process is simpler, cheaper, no need for large volumes of solvent)

In a further advantage embodiments as hereinbefore and hereinbelow defined provide the ability to use water-unstable additives, water-insoluble or poorly soluble additives, dense powders, and higher concentrations of additives, than would be achievable if those were formulated in the aqueous phase only.

In a further advantage embodiments as hereinbefore and hereinbelow defined provide foams where such additives are homogeneously distributed throughout the thickness of the PU slabstock.

In a further advantage embodiments as hereinbefore and hereinbelow defined provide a means to overcome the natural tendency to settle of this type of additive composition mixed in an aqueous phase, which leads to inhomogeneous delivery of additive concentration to the mixing head.

In a further advantage embodiments as hereinbefore and hereinbelow defined comprise control of particle size of species-releasing additive such as silver salt in the case of isocyanate-additive slurry or organic carrier-additive slurry, and this is particularly of interest where small particle size enhances the release of an antimicrobial species such as silver ions. When processed in a liquid phase, the particle size of the salt or species of interest can vary greatly depending on temperature, concentration, and the tendency of the powder to self-aggregate. This can be overcome by keeping the powder dry by incorporation into the finished porous material via an isocyanate-additive slurry or an organic carrier-additive slurry as hereinbefore defined.

In a further advantage embodiments as hereinbefore and hereinbelow defined comprising providing additive or powder charge thereof in isocyanate phase or organic carrier phase, which may aid in preventing self-agglomeration.

In an advantage embodiments as hereinbefore and hereinbelow defined comprise additive homogeneously loaded within the structural matrix framework of the porous matrix. Thereby a matrix such as a slabstock can be cut to any size or shape, exposing an additive loaded face and structural matrix framework in uniform loading irrespective of originating portion of slabstock.

In further embodiments there is provided a system for process control of a method for manufacture of material as hereinbefore defined. Advantageously such system provides control selected from control of flow rates, control of flow intervals, control or recirculation volume or rates or intervals for respective phases or concentrate herein, control of dosing of slurry phase or solid concentrate and the like.

In embodiments said system is a system for process control of continuous flow and steady flow rate of isocyanate phase and aqueous phase in supply lines, and batchwise admixing at mixing head and casting at casting head, and of recirculation circuits for respective phases upstream of said mixing head wherein said slurry or solid concentrate of powder charge in a part of said isocyanate phase and/or a part of said aqueous phase is provided intermittently to said mixing head or point upstream or downstream thereof without recirculation thereof or process control thereof in an independent recirculation circuit.

In the case of a continuous method, said system may be a system for process control of dosing slurry phase or solid concentrate to a 2-way mixing head with a stream of said isocyanate phase or part thereof, or said aqueous phase or part thereof and thence to a further 2-way mixing head with a stream of other said phase; or to a 2-way mixing head with a stream of said intimately admixed isocyanate phase or part thereof and aqueous phase or part thereof; or to a 3-way mixing head with respective streams of said isocyanate phase or part thereof and said aqueous phase or part thereof.

In a further aspect there is provided herein a device comprising hydrophilic polyurethane material as herein defined together with one or more additional materials, preferably comprising a layer of polyurethane material herein together with one or more additional material layers.

In embodiments said device is an antimicrobial device for application to a locus and activation by contact with aqueous medium provided at said locus, said device comprising (a) a locus contacting surface or layer and/or (b) an opposing non-locus contacting surface or layer together with (c) an aqueous medium absorbing layer comprised between or in combination with (a) and/or (b)

wherein (c) comprises polyurethane material as herein defined.

In embodiments said device is a wound dressing or part thereof for application to a wound locus and activation by contact with fluid at said wound locus, said wound dressing comprising (a) a wound contacting surface or layer and/or (b) an opposing non-wound contacting surface or layer together with (c) one or more optional fluid absorbing layers comprised therebetween between or in combination with one thereof wherein (c) comprises polyurethane material loaded with additive as herein defined.

Layer or surface (a) may be adhesive or non-adhesive, for example is a conformable elastomeric apertured film.

Layer or surface (b) is conveniently a breathable top film permitting fluid and air regulation at the locus and providing an antimicrobial barrier, preferably a continuous moisture vapour transmitting conformable polymer film. A layer (b) may comprise a border about the perimeter of material (c).

Said device may comprise additional layers selected from a masking layer (b') comprised between a layer (b) and a layer (c), a superabsorbent layer (b") comprised between a layer (b) and a layer (c) and the like.

Layers may be laminated and/or sealed within a pouch formed by outer layers in a contiguous and co-extensive relationship.

Material or device herein may be sterile, terminally sterile and/or sealed in moisture and/or microbe impermeable packaging such as a silver foil pouch.

In further embodiments there is provided a method for manufacture of a device herein.

In further embodiments there is provided a method for treating a locus so as to aid in locus health or condition, for example rendering or maintaining a locus free from microbes deleterious to the health of said locus which comprises contacting the locus with material or device such as antimicrobial material or device as hereinbefore defined thereby enabling release of antimicrobial species into said locus. Preferably such method is a method of treating a wound locus thereby enabling release of antimicrobial species into said wound locus. In an advantage antimicrobial material and device herein release antimicrobial species, notably silver ion, rapidly in high concentration, with release sustained for a required duration, for example up to 7, 8 or 10 days or more.

In another aspect, a method of treating a wound is provided. The method comprises:

placing a wound dressing comprising a loaded wound dressing layer into or over the wound, wherein the loaded wound dressing layer comprises a polyurethane foam and a powder charge of antimicrobial release additive pre-loaded within the foam, wherein the antimicrobial release additive is homogeneously distributed within the loaded wound dressing layer by admixing the powder charge with one or more of an isocyanate phase precursor, an aqueous phase precursor and a liquid carrier phase for the polyurethane foam prior to polymerization;

wherein the antimicrobial release additive is activated for the release of an antimicrobial agent into the wound from the wound dressing upon contact with moist or aqueous medium.

In some embodiments, the homogeneous distribution of antimicrobial release additive within the loaded wound dressing is formed by admixing one or more slurry phases of said powder charge or solid concentrate of said powder charge with one or more of the isocyanate phase precursor, the aqueous phase precursor and the liquid carrier phase for the polyurethane foam prior to polymerization. In some embodiments, the homogeneous distribution of antimicrobial release additive within the loaded wound dressing may be formed by including the powder charge within the isocyanate phase precursor of the polyurethane foam prior to polymerization. In some embodiments, the homogeneous distribution of antimicrobial release additive within the loaded wound dressing may be formed by including the powder charge within the aqueous phase precursor of the polyurethane foam prior to polymerization. In some embodiments, the homogeneous distribution of antimicrobial release additive within the loaded wound dressing may be formed by including the powder charge within the carrier liquid phase for the polyurethane foam prior to polymerization. In some embodiments, the method may further comprise releasing said antimicrobial agent for 7 days or more. In some embodiments, the method may further comprise releasing said antimicrobial release agent in an amount up to 1.8 mg/cm$^2$ per day. The method may further comprise allowing wound exudate to contact the loaded wound dressing layer before releasing at least a portion of the antimicrobial agent toward the wound, wherein the antimicrobial agent is configured to diffuse into wound exudate upon contact with wound exudate. The method may further comprise applying negative pressure to the wound dressing. In some embodiments, the antimicrobial release additive may be selected from a group consisting of elemental silver, silver salts, silver complexes, caged forms thereof, caged forms of iodine and combinations thereof. The antimicrobial release additive may be selected from a group consisting of silver sulfadiazine, silver zeolite, silver sulfate, silver carbonate, silver chloride, silver nitrate, silver oxide, silver phosphate, silver citrate, silver acetate, silver lactate, cadexomer iodine, copper salts and complexes, zinc salts and complexes, gold salts and complexes, chlorhexidine gluconate, polyhexamethylenebiguanide hydrochloride, and combinations thereof. In one embodiment the antimicrobial release additive may be selected from a group consisting of silver sulfadiazine, silver zeolite, silver sulfate, silver carbonate, silver chloride, silver nitrate, silver oxide, silver phosphate, silver citrate, silver acetate, silver lactate, cadexomer iodine. and combinations thereof. The antimicrobial agent may comprise silver ion and/or iodine. The powder charge of antimicrobial additive may further comprise super absorbent polymer. The antimicrobial release additive may have a particle size distribution of D50<10 micron. In some embodiments, the wound dressing may further comprise an absorbent layer that absorbs wound exudate; and/or a wound contact layer positioned in contact with the wound below the loaded wound dressing layer.

In some embodiments, the wound dressing may further comprise one or more active ingredients in place of, or in addition to the antimicrobial release additive. The active ingredients may for example include powdered growth factors and small active organic molecules (useful for debridement e.g., collagenase, or useful for promoting healing response e.g. MMP-inhibitors), topical oxygen delivery compounds (e.g. variants on haemoglobin), and any other organic or inorganic bacteriostatic, antibacterial, antiseptic or antimicrobial agent.

If the disclosed technology is in the form of a slurry, active For example the active ingredients in a slurry may exclude the growth factors, MMP-inhibitors, collagenase, haemoglobin variants.

In another aspect, a wound dressing is provided. The wound dressing comprises:

- a loaded wound dressing layer comprising:
  - a polyurethane foam comprising a wound facing face and a reverse face; and
  - a powder charge of antimicrobial release additive preloaded within the foam, wherein the antimicrobial release additive is homogeneously distributed within the loaded wound dressing layer by admixing the powder charge with one or more of an isocyanate phase precursor, an aqueous phase precursor, and a liquid carrier phase for the polyurethane foam prior to polymerization.

In some embodiments, the homogeneous distribution of antimicrobial release additive within the loaded wound dressing is formed by admixing one or more slurry phases of said powder charge or solid concentrate of said powder charge with one or more of the isocyanate phase precursor, the aqueous phase precursor and the liquid carrier phase for the polyurethane foam prior to polymerization. In some embodiments, the homogeneous distribution of antimicrobial release additive within the loaded wound dressing may be formed by including the powder charge within the isocyanate phase precursor of the polyurethane foam prior to polymerization. In some embodiments, the homogeneous distribution of antimicrobial release additive within the loaded wound dressing may be formed by including the powder charge within the aqueous phase precursor of the polyurethane foam prior to polymerization. In some embodiments, the homogeneous distribution of antimicrobial release additive within the loaded wound dressing may be formed by including the powder charge within the carrier liquid phase for the polyurethane foam prior to polymerization. In some embodiments, the antimicrobial release additive comprises elemental silver, silver salts, silver complexes, caged forms thereof, caged forms of iodine and combinations thereof. In some embodiments, the antimicrobial release additive may be selected from a group consisting of silver sulfadiazine, silver zeolite, silver sulfate, silver carbonate, silver chloride, silver nitrate, silver oxide, silver phosphate, silver citrate, silver acetate, silver lactate, cadexomer iodine and combinations thereof. In some embodiments, the antimicrobial release additive may be in an amount of 1.4 mg/cm$^2$ to 4 mg/cm$^2$ at the wound facing face. In some embodiments, the wound dressing may further comprise a wound contact layer below the loaded wound dressing layer; a cover layer over the loaded wound dressing layer; a fluidic connector configured to connect the cover layer to a source of negative pressure; and/or an absorbent layer over the loaded wound dressing layer. The absorbent layer may comprise superabsorbent particles. In some embodiments, the powder charge may further comprise superabsorbent polymer. The antimicrobial release additive may have a particle size distribution of D50<10 micron. The foam may comprise a plurality of cells and wherein the antimicrobial release additive is at least partially embedded within said cells.

Variations and modifications of these embodiments will occur to those of skill in the art after reviewing this disclosure. The foregoing features and aspects may be implemented, in any combination and sub-combinations (including multiple dependent combinations and sub-combinations), with one or more other features described herein. The various features described or illustrated above, including any components thereof, may be combined or integrated in other systems. Moreover, certain features may be omitted or not implemented.

Further areas of applicability of the disclosed devices and methods will become apparent from the detailed description provided hereinafter. It should be understood that the detailed description and specific examples, while indicating particular embodiments, are intended for purposes of illustration only and are not intended to limit the scope of the disclosure or any of the claims that may be pursued.

BRIEF DESCRIPTION OF THE DRAWINGS

The foregoing and other objects and advantages will be appreciated more fully upon consideration of the following detailed description, taken in conjunction with the accompanying drawings, in which like reference numbers refer to like parts throughout. These depicted embodiments are to be understood as illustrative and not limiting in any way:

FIGS. **1-3*b*** illustrate prior art and herein methods for preparing polyurethane foam materials;

FIG. 4 illustrates by cross-section SEM, prior art point of manufacture loaded polyurethane material;

Figure 7:
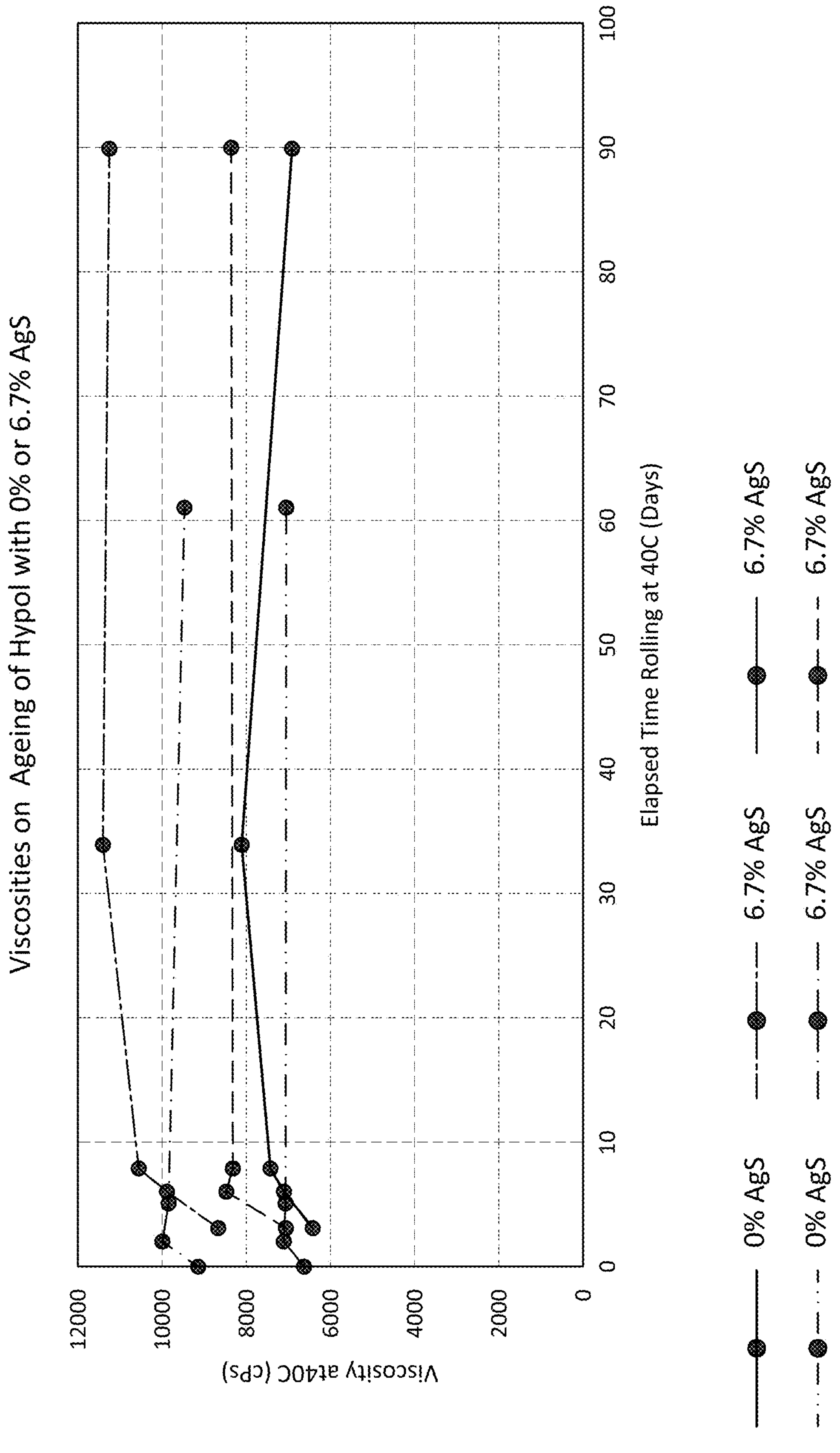
Figure 8A:
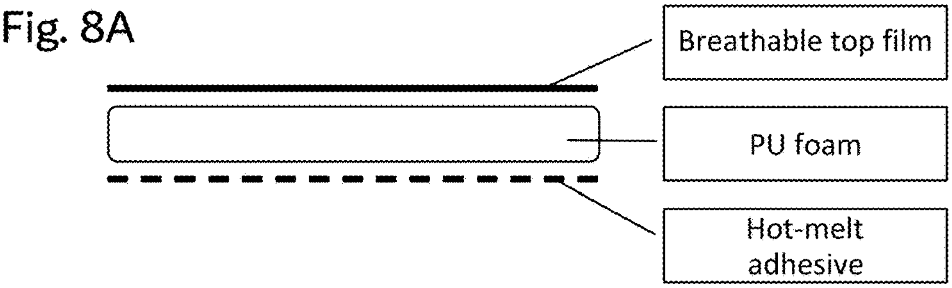
Figure 8B:
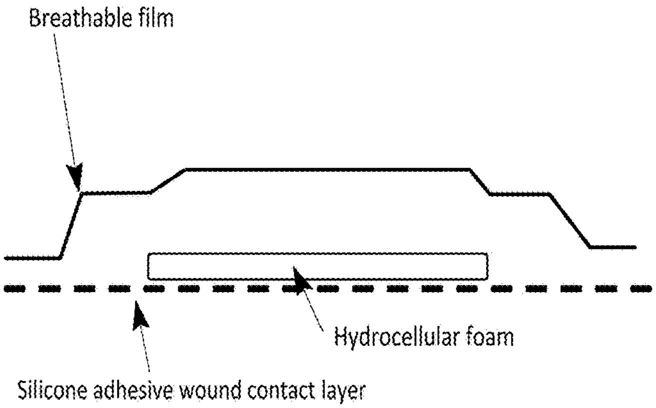
Figure 8C:
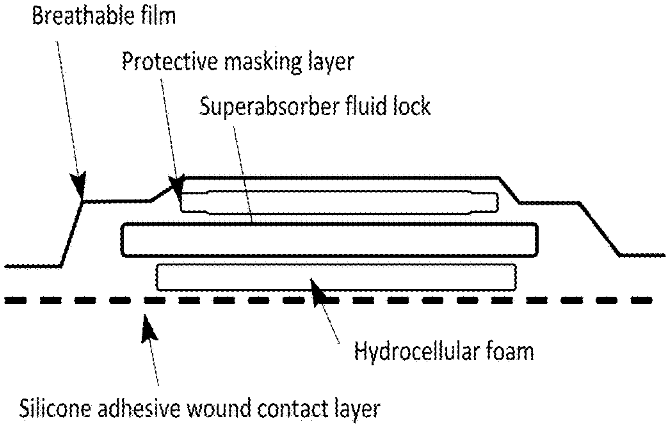
Figure 8D:
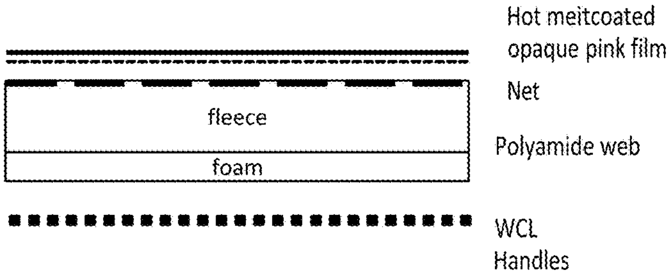
Figure 9:
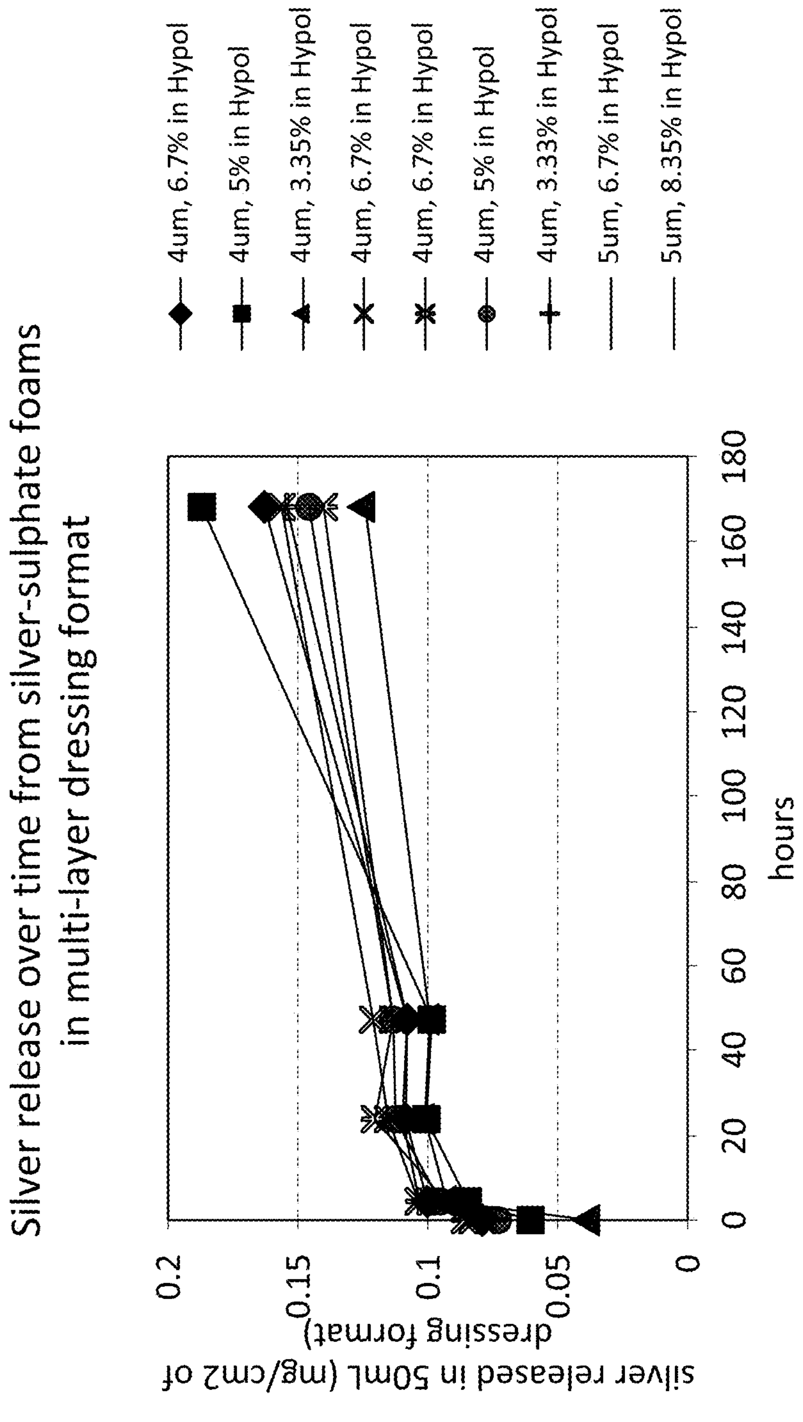
Figure 10:
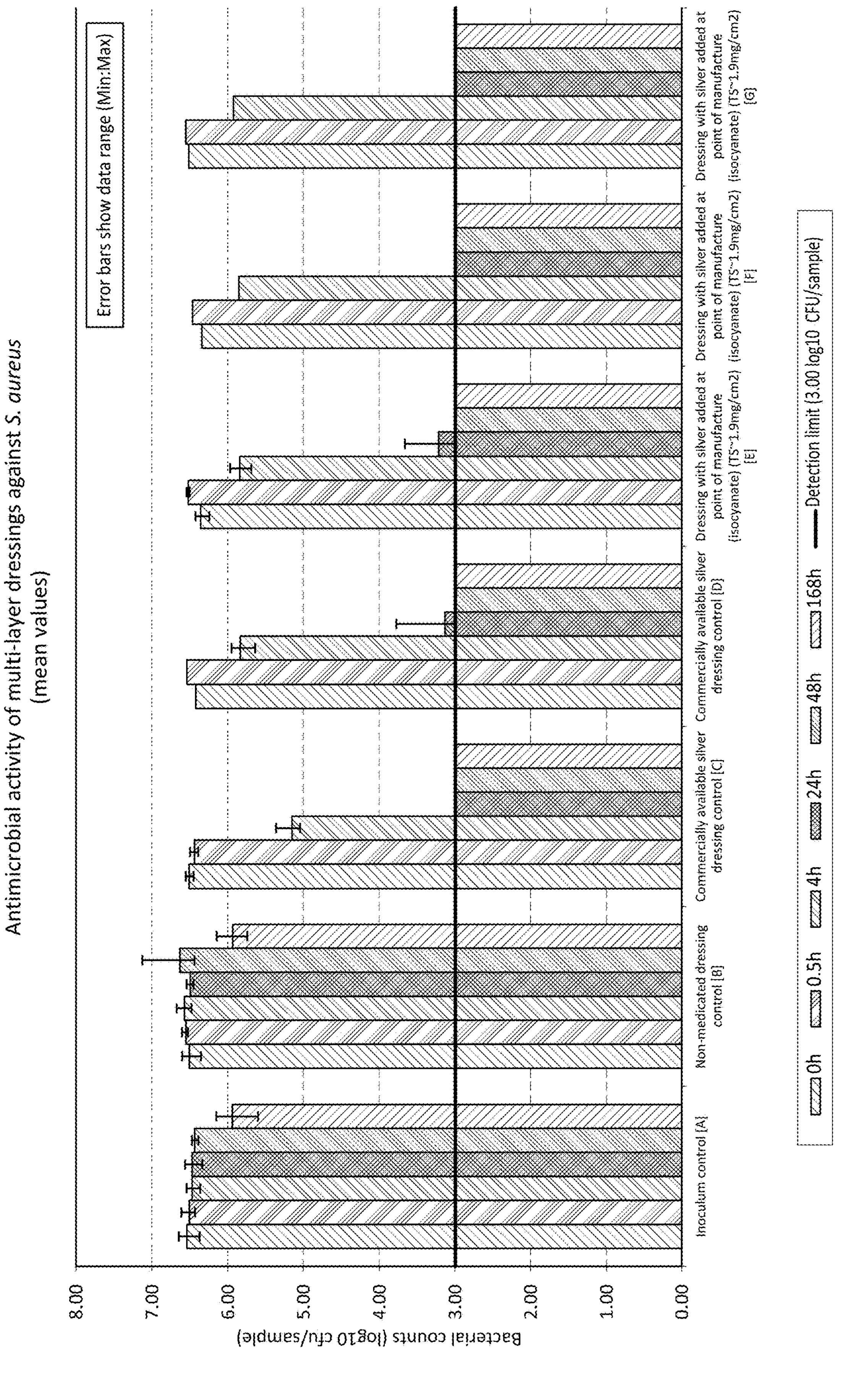
Figure 11:
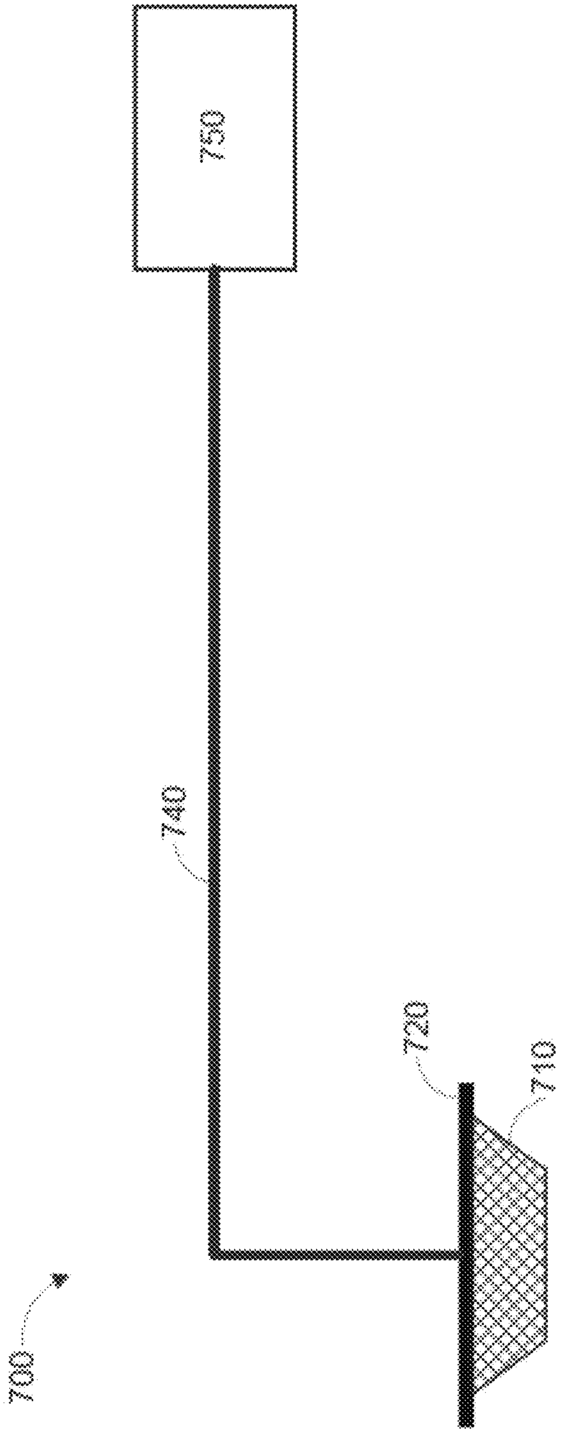
Figure 12A:
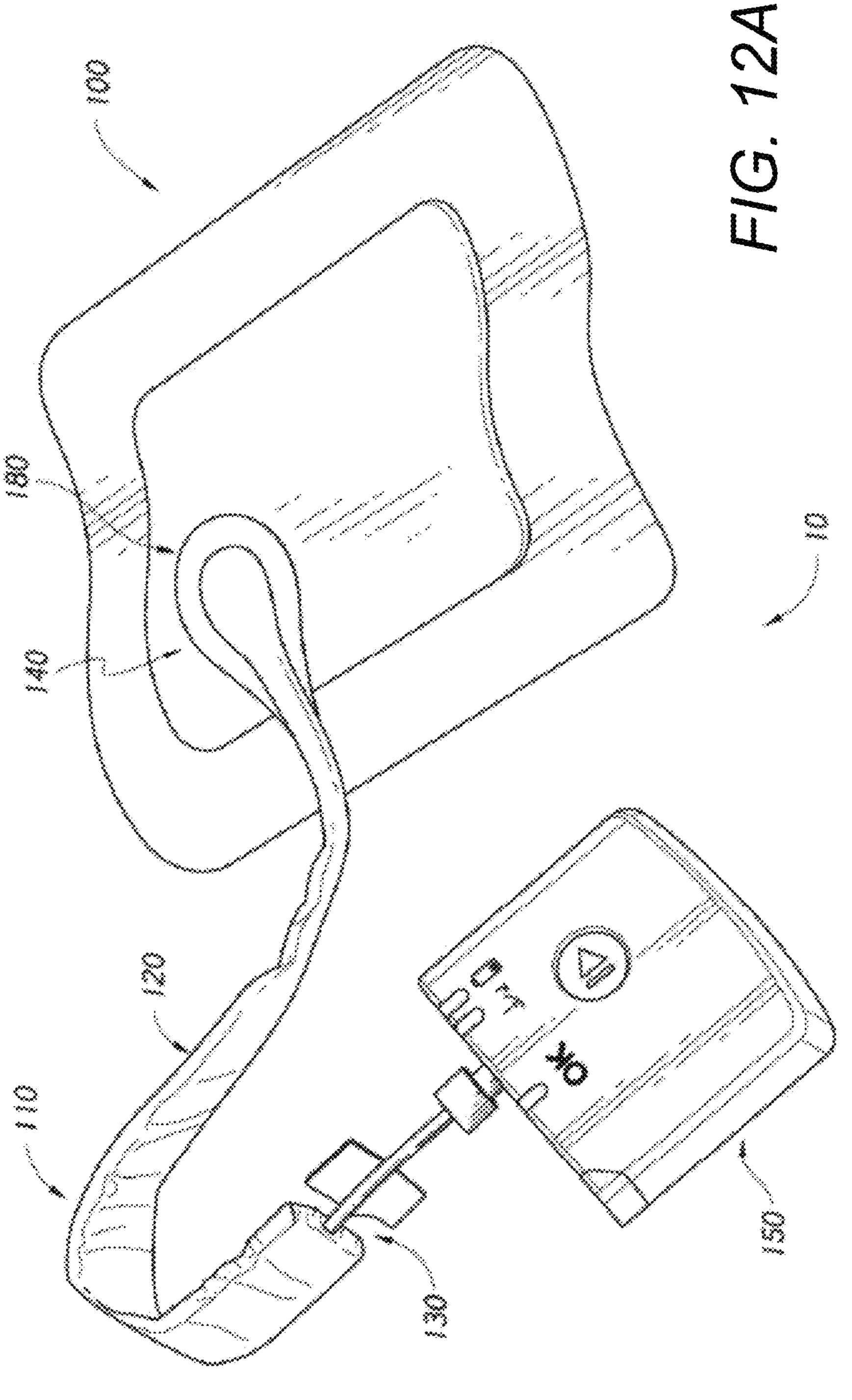
Figure 12B:
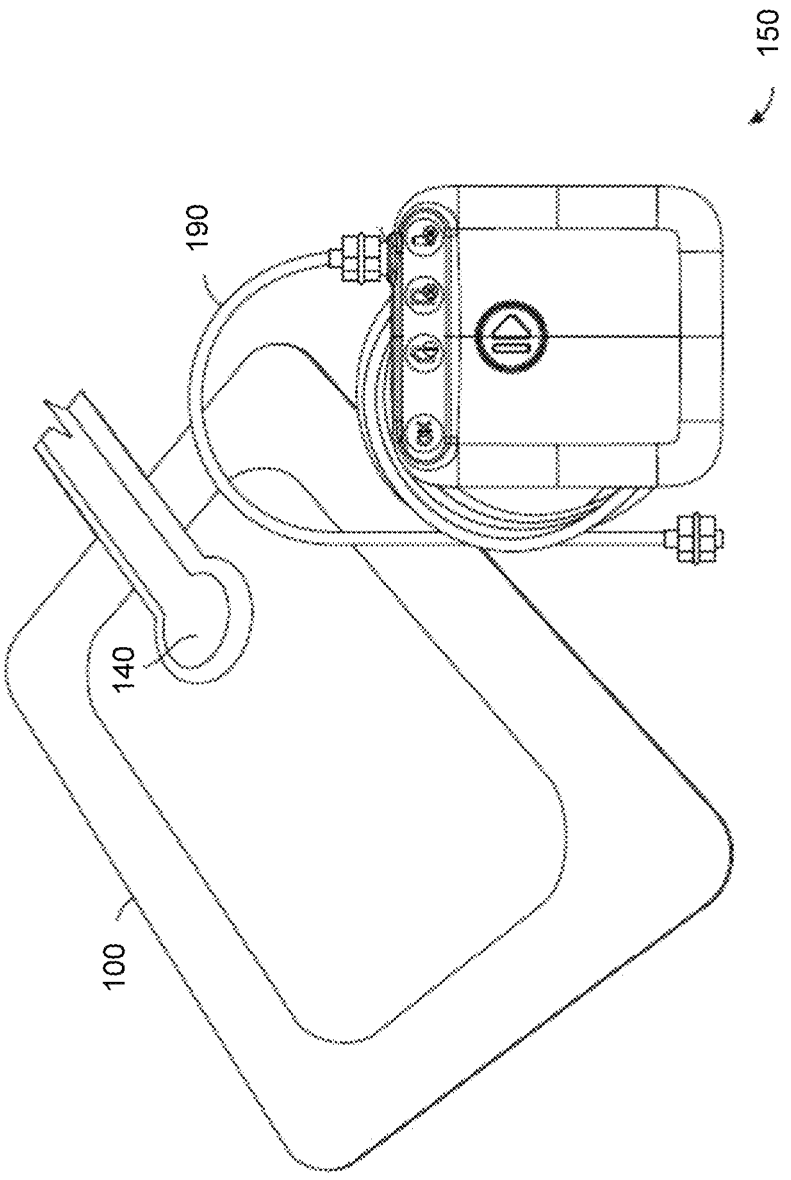
Figure 12C:
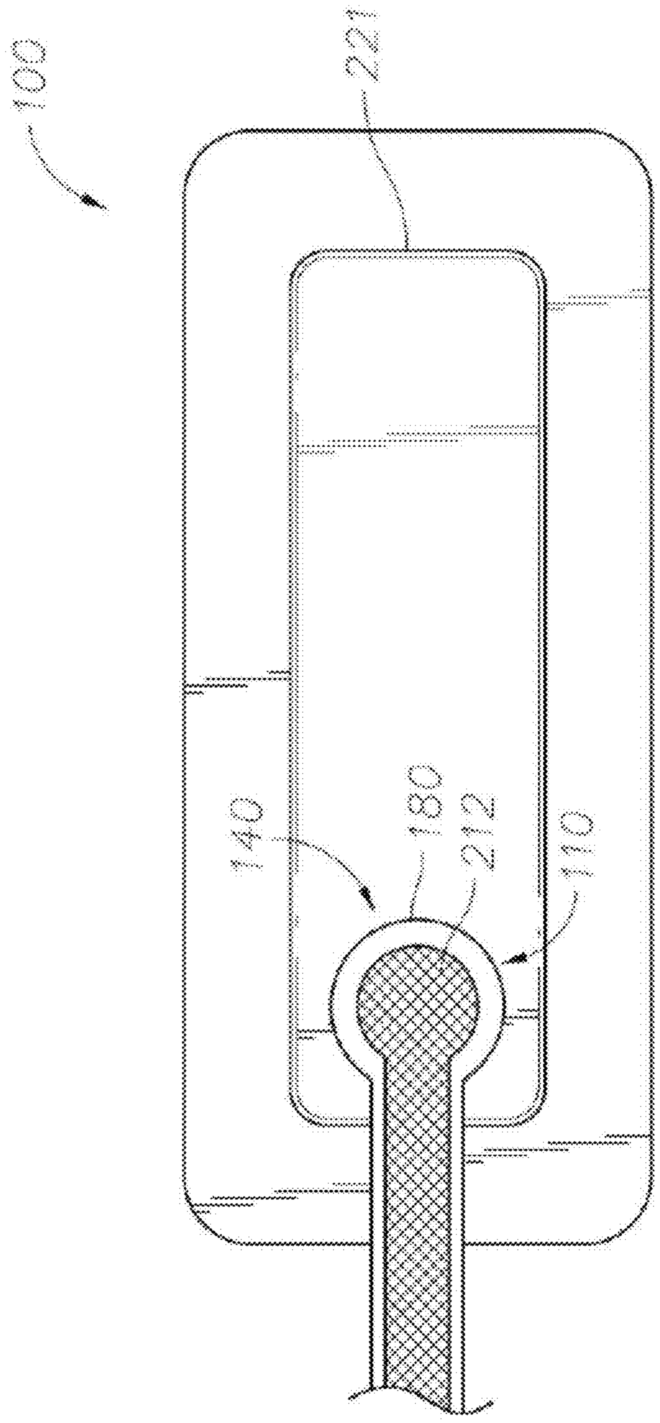
Figure 12D:
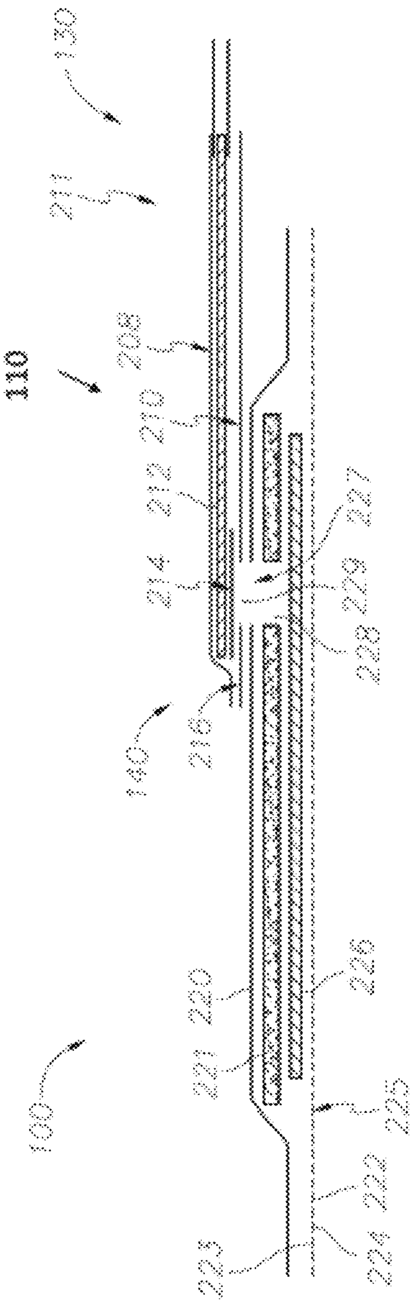
Figure 13A:
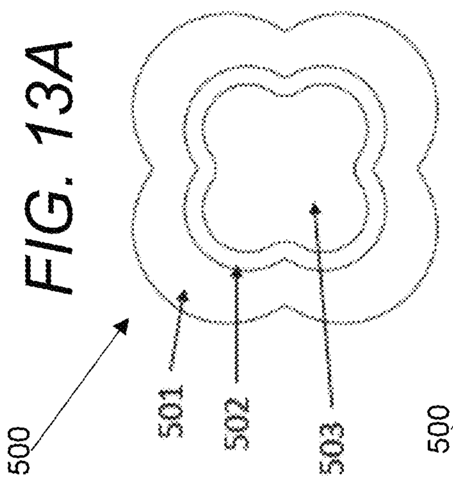
Figure 13B:
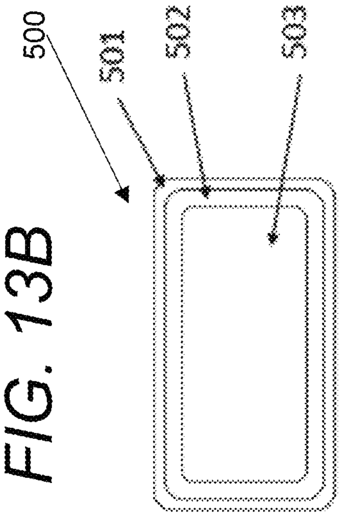
Figure 13C:
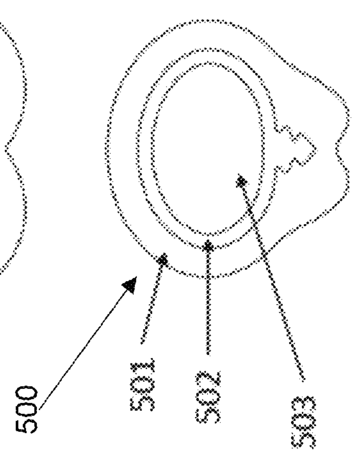
Figure 13D:
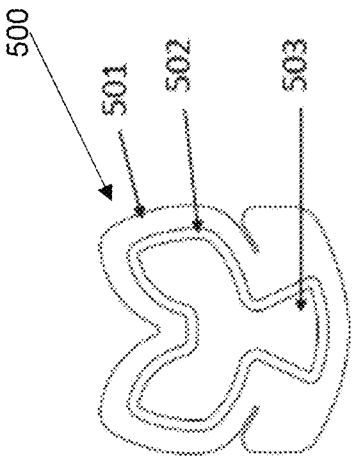
Figure 13E:
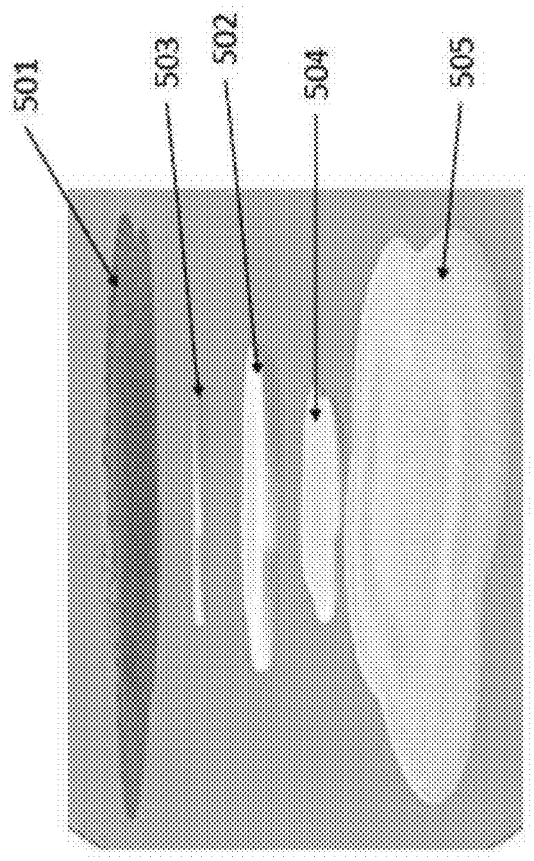
Figure 14A:
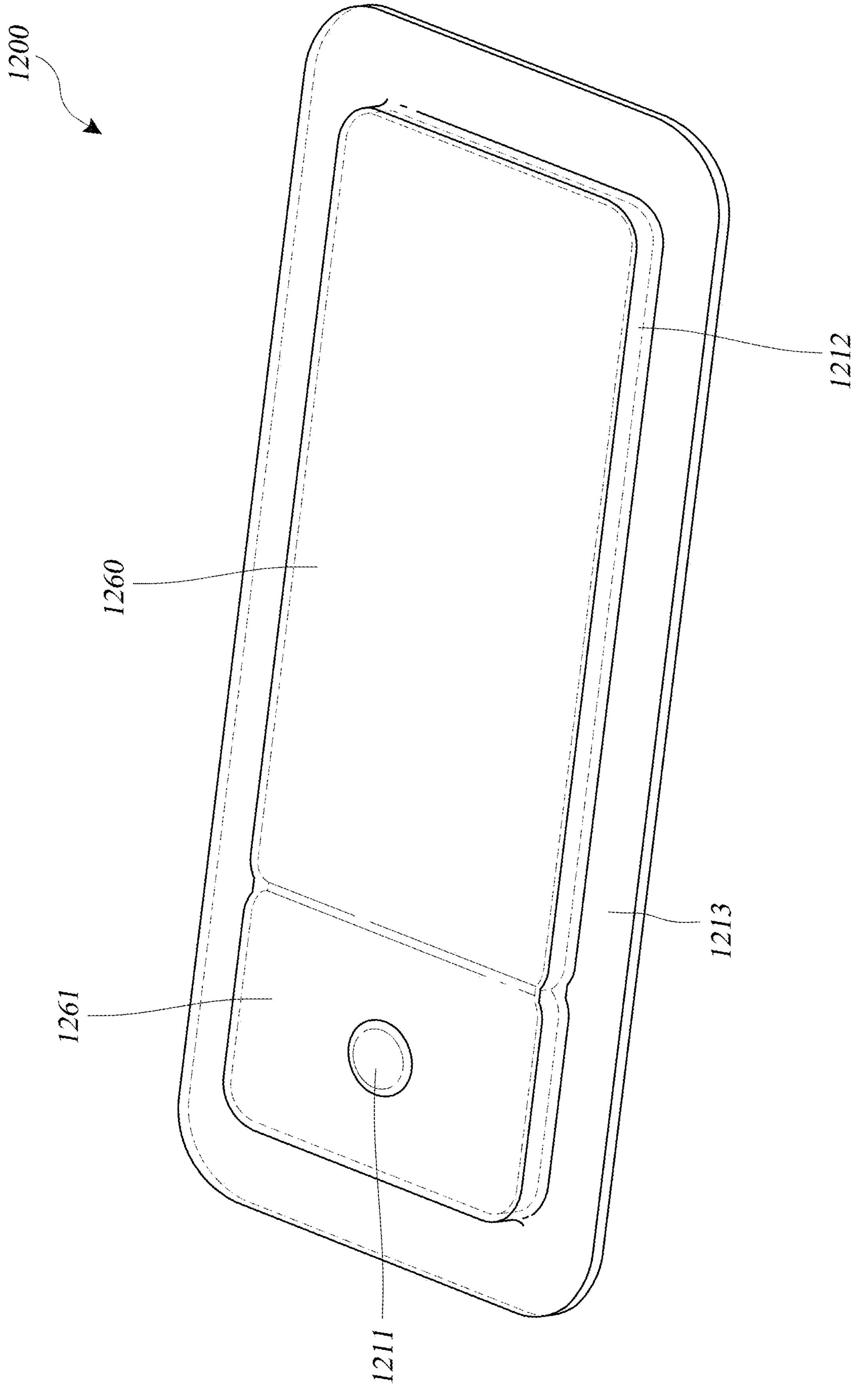
Figure 14B:
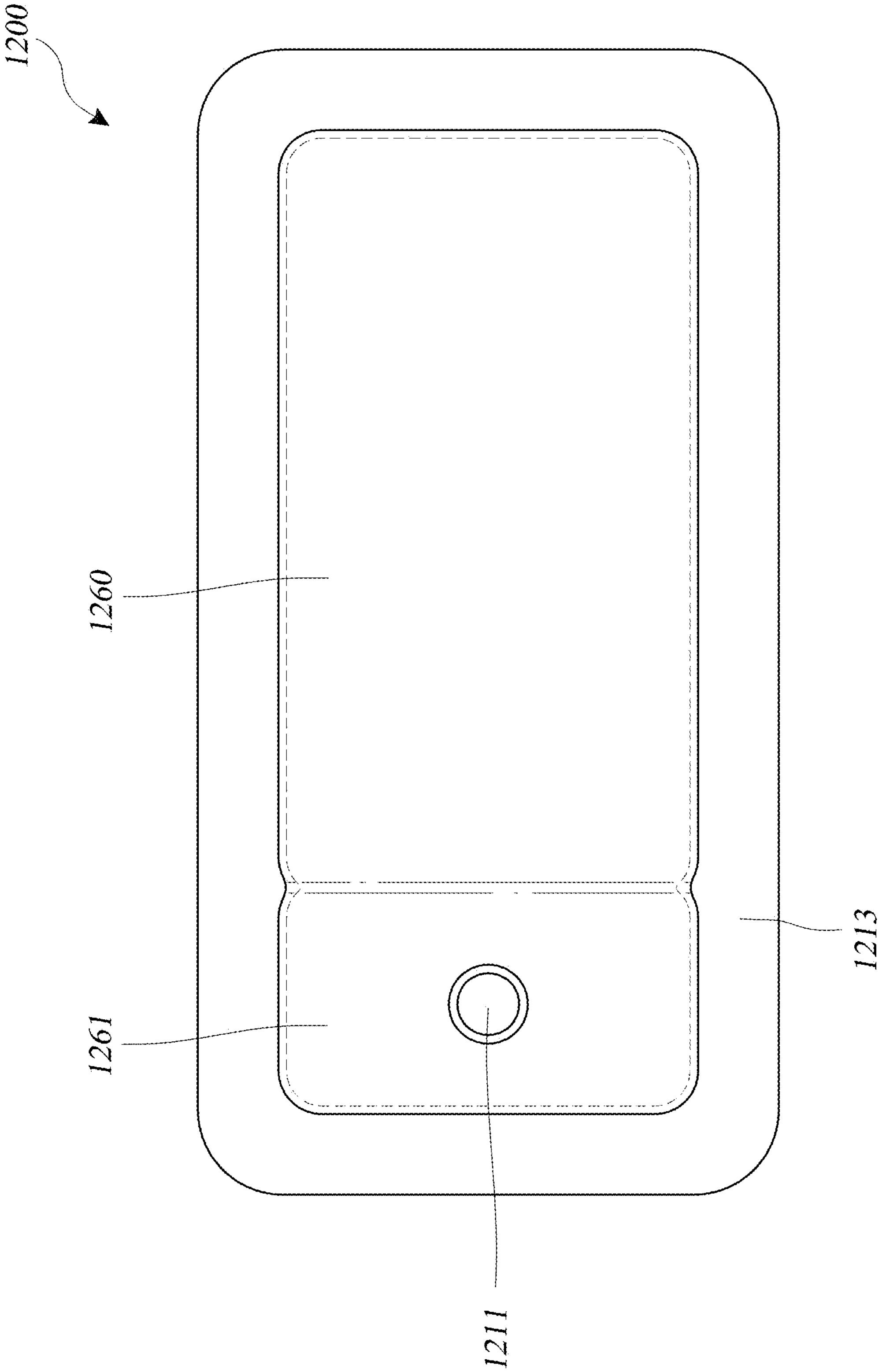
Figure 14C:
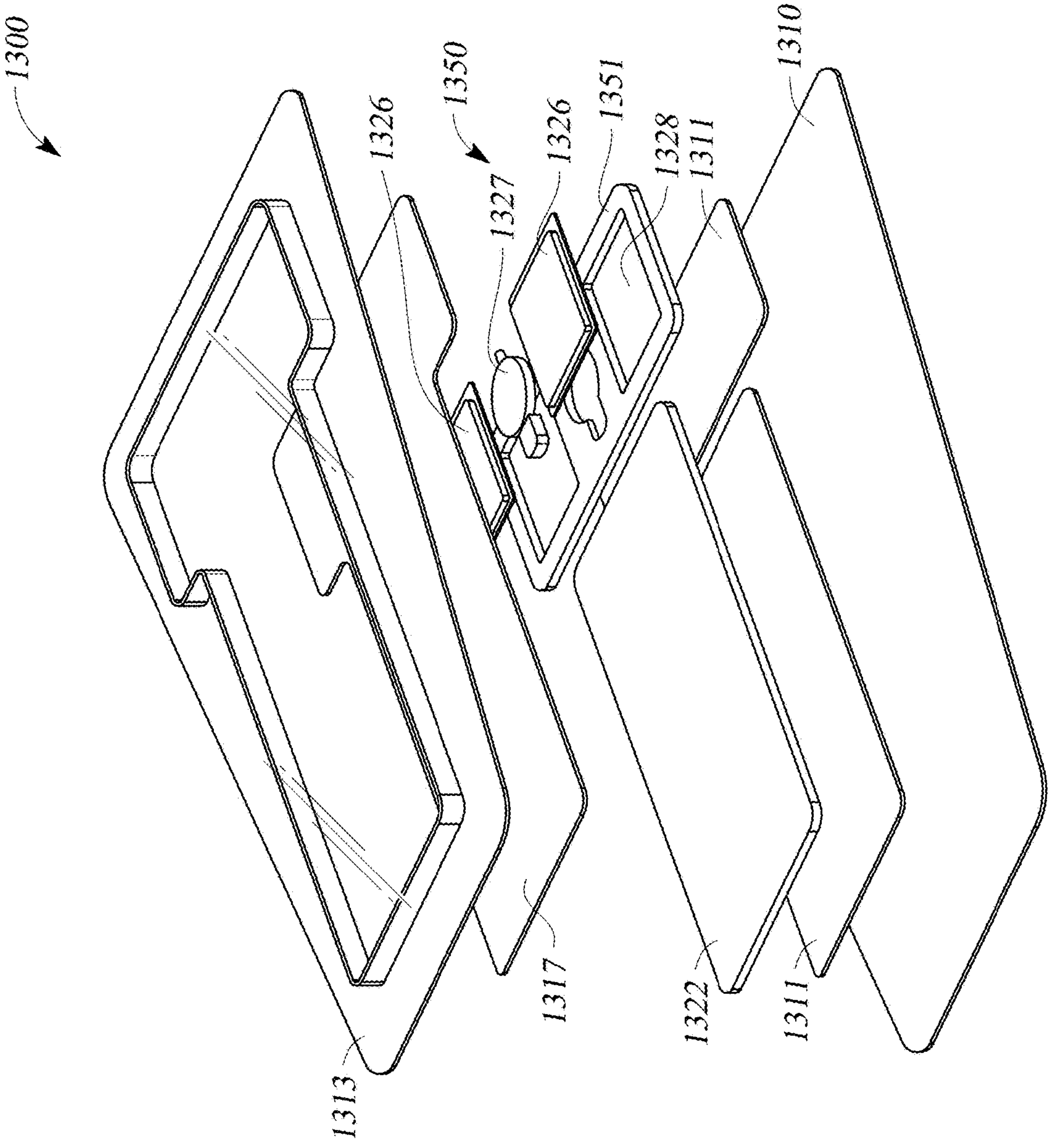
Figure 15A:
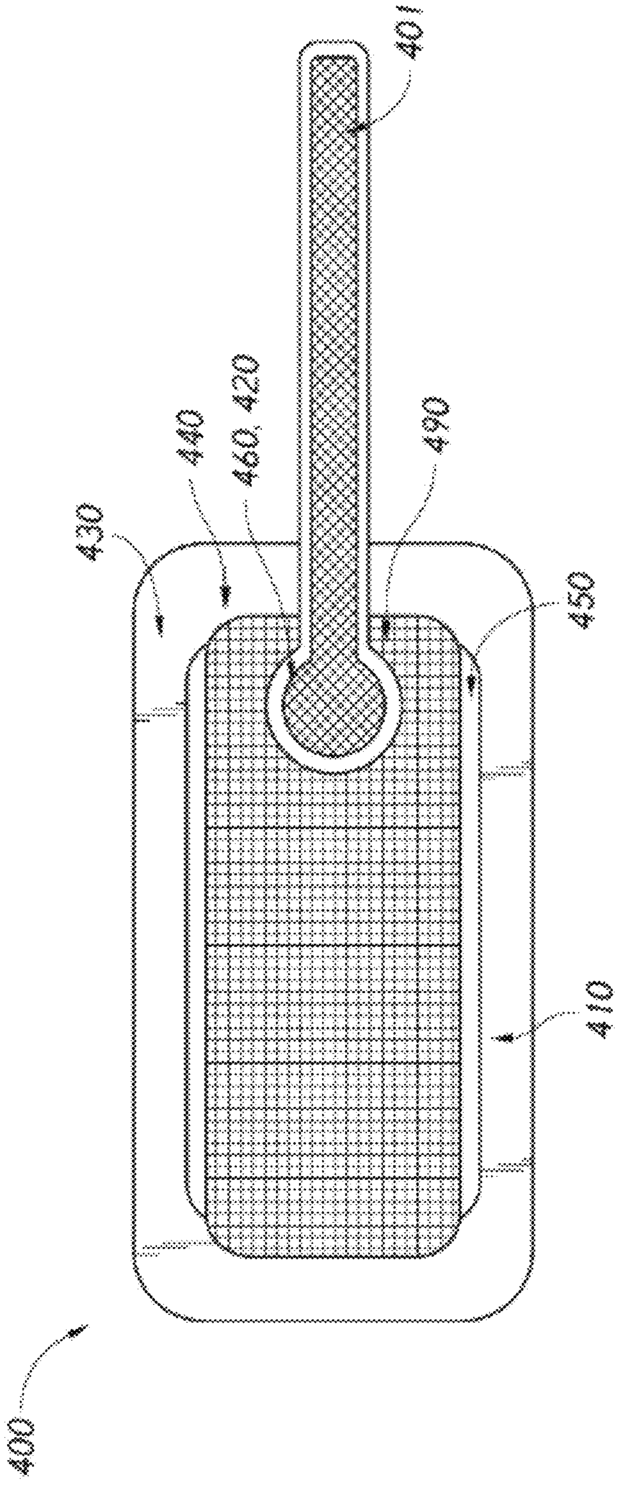
Figure 15B:
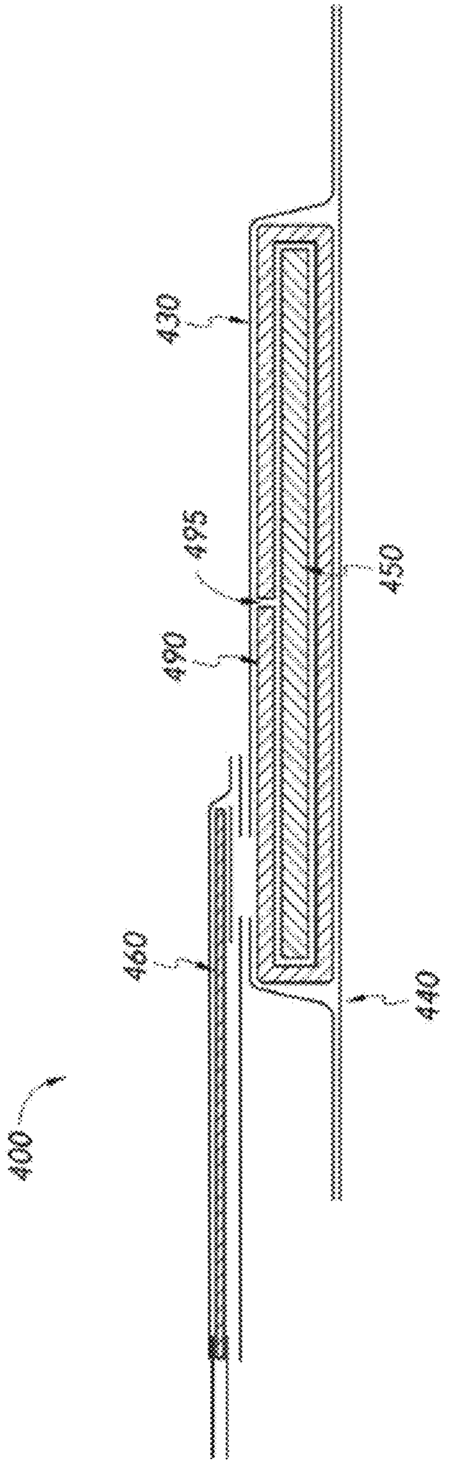
Figure 15C:
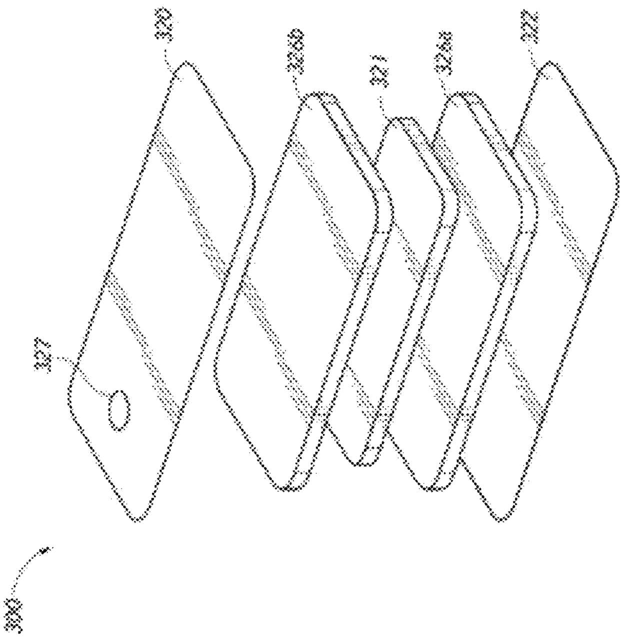
Figure 16A:
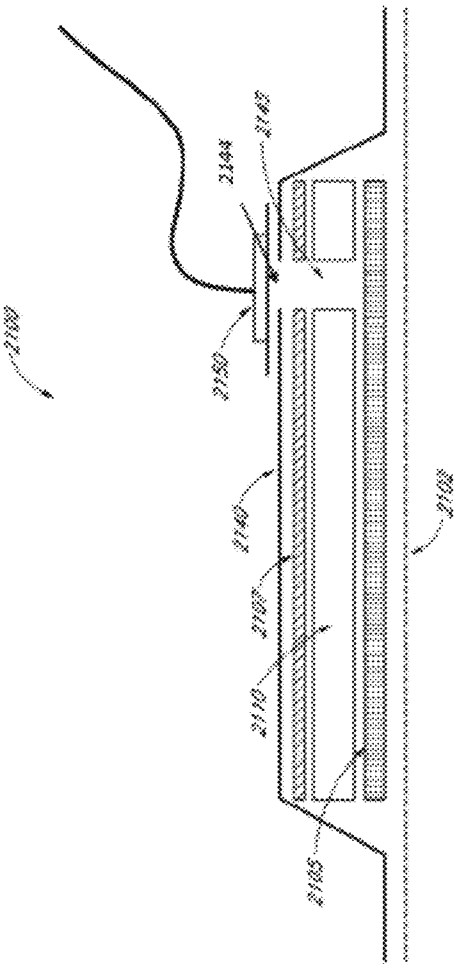
Figure 16B:
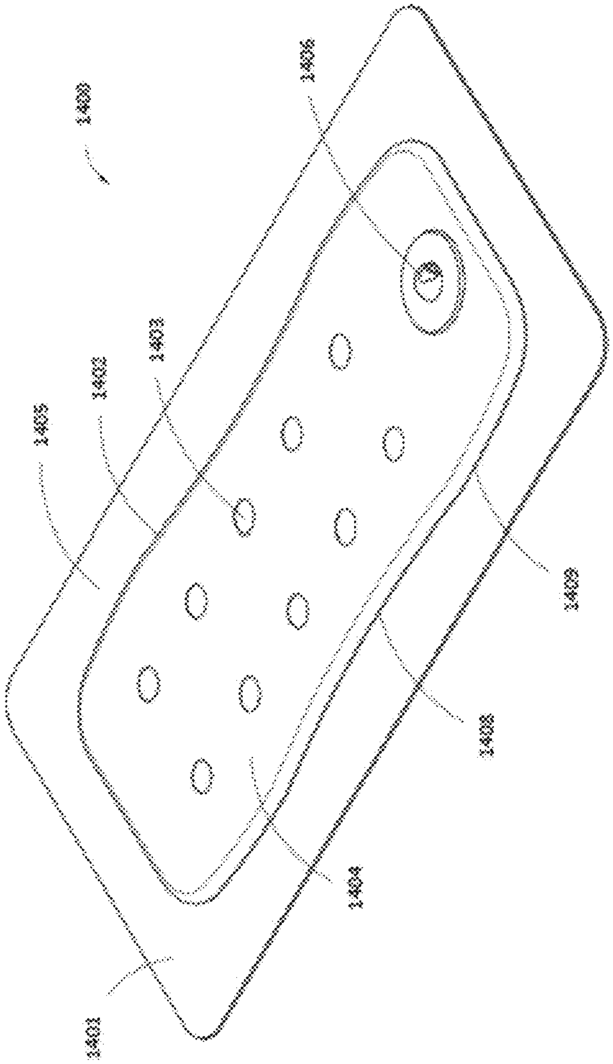
Figure 17:
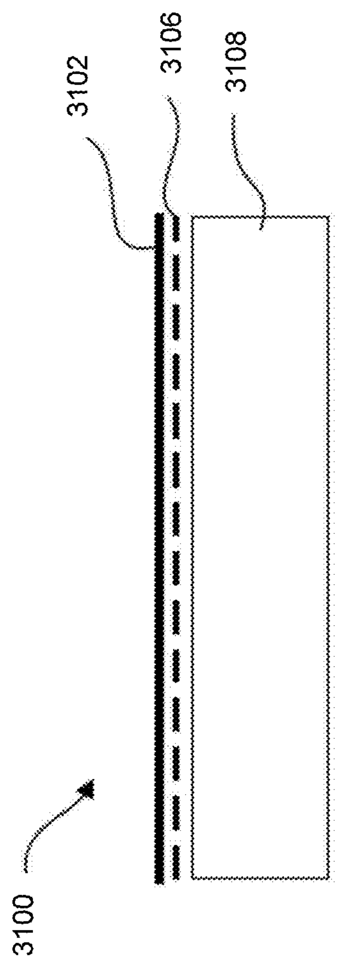
Figure 18:
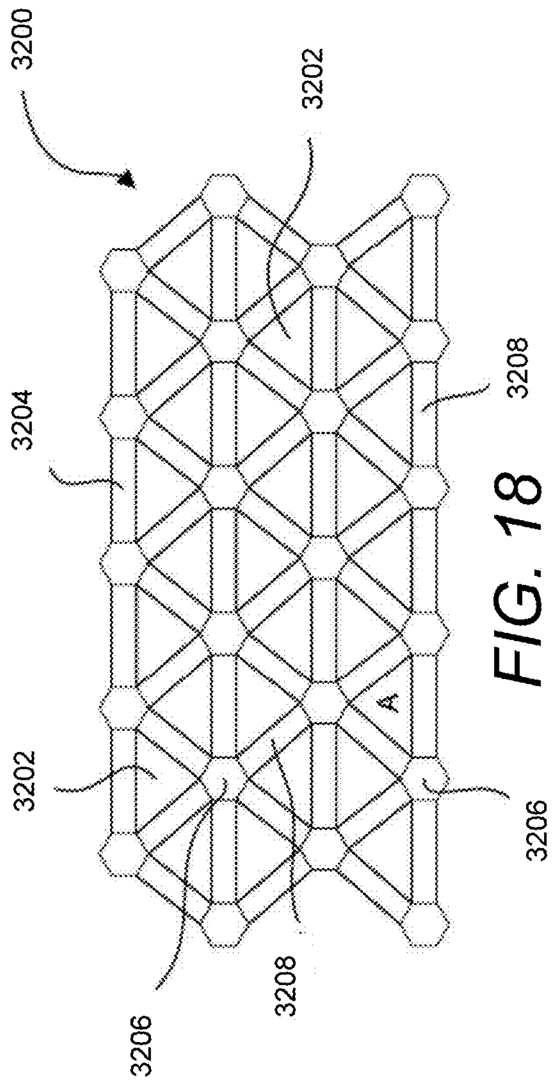
Figure 19A:
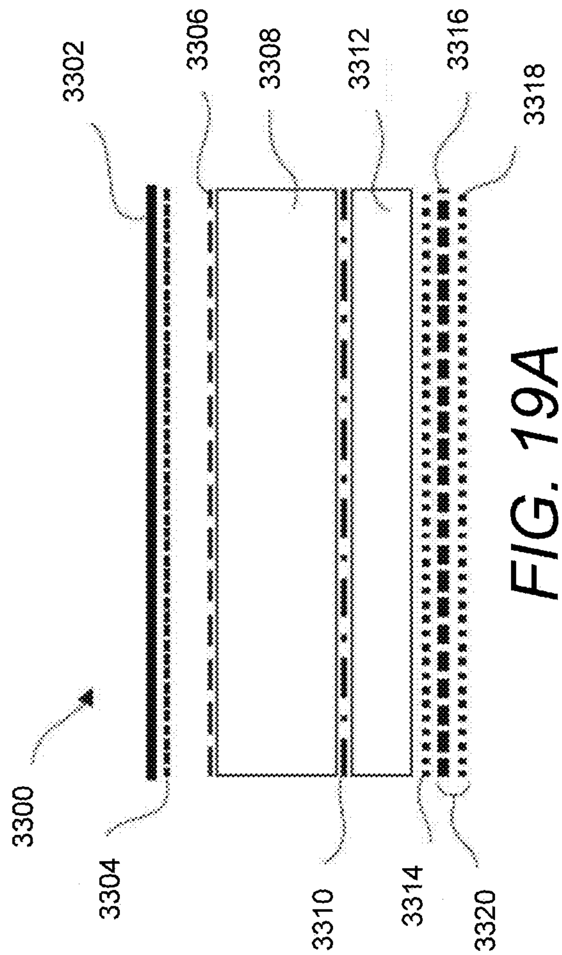
Figure 19B:
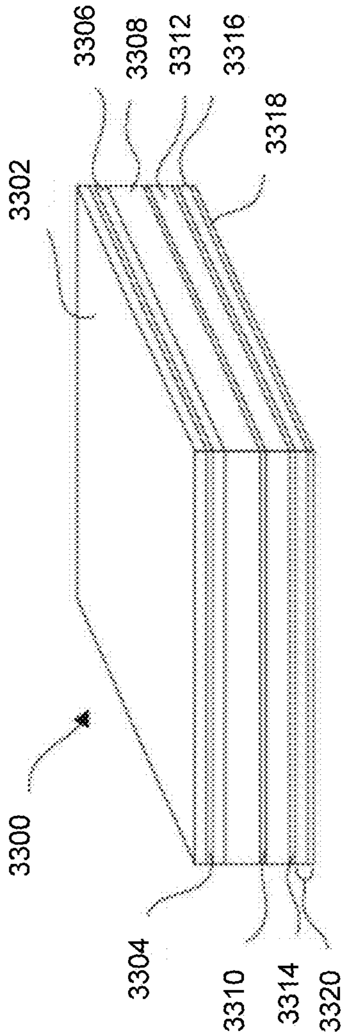
Figure 20:
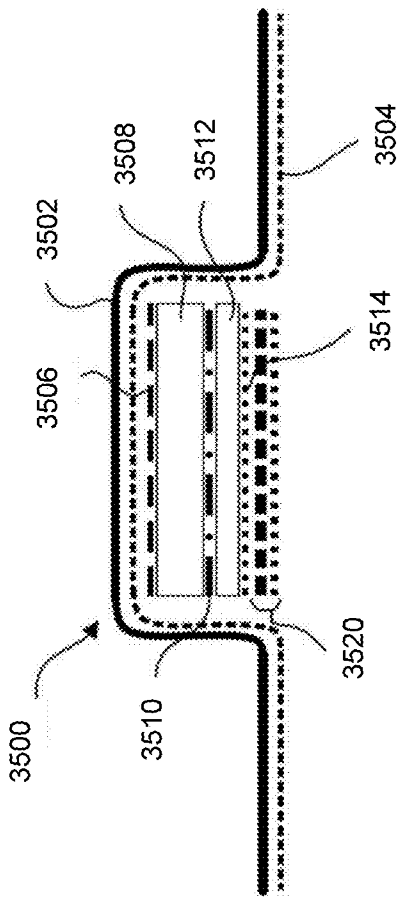
Figure 21:
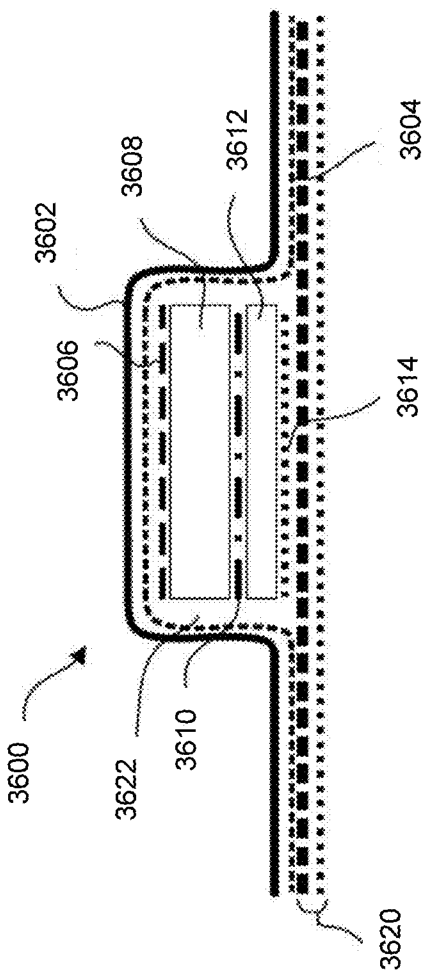

FIGS. **5*a*, 5*b* and 6** illustrate by cross-section SEM, point of manufacture loaded polyurethane material herein;

FIG. 7 illustrates stability of aged slurry phase or solid concentrate herein;

FIGS. **8*a-d*** illustrate wound dressing formats including polyurethane foam;

FIGS. 9 and 10 illustrate silver ion release from wound dressings herein;

FIG. 11 is a schematic diagram of an example of a negative pressure wound therapy system;

FIG. 12A illustrates an embodiment of a negative pressure wound treatment system employing a flexible fluidic connector and a wound dressing capable of absorbing and storing wound exudate;

FIG. 12B illustrates an embodiment of a negative pressure wound treatment system employing a flexible fluidic connector and a wound dressing capable of absorbing and storing wound exudate;

FIG. 12C illustrates an embodiment of a negative pressure wound treatment system employing a flexible fluidic connector and a wound dressing capable of absorbing and storing wound exudate;

FIG. 12D illustrates a cross section of an embodiment of a fluidic connector connected to a wound dressing;

FIGS. 13A-13D illustrates an embodiment of a wound treatment system employing a wound dressing capable of absorbing and storing wound exudate to be used without negative pressure;

FIG. 13E illustrates a cross section of an embodiment of a wound treatment system employing a wound dressing capable of absorbing and storing wound exudate to be used without negative pressure;

FIGS. 14A-14B illustrate an embodiment of a wound dressing incorporating the source of negative pressure and/or other electronic components within the wound dressing;

FIG. 14C illustrates an embodiment of layers of a wound dressing with the pump and electronic components offset from the absorbent area of the dressing;

FIG. 15A illustrates an embodiment of a negative pressure wound treatment system employing a flexible fluidic connector and a wound dressing with a wrapped around spacer layer, the wound dressing capable of absorbing and storing wound exudate;

FIG. 15B illustrates a cross sectional view of an embodiment of a negative pressure wound treatment system employing a flexible fluidic connector and a wound dressing with a wrapped around spacer layer, the wound dressing capable of absorbing and storing wound exudate;

FIG. 15C illustrates an embodiment of a negative pressure wound treatment system employing a wound dressing capable of absorbing and storing wound exudate;

FIG. 16A illustrates another embodiment of a wound dressing in cross-section;

FIG. 16B illustrates a perspective view of an embodiment of a wound dressing including an obscuring layer and viewing windows;

FIG. 17 is a schematic diagram of a section of an example of a wound dressing;

FIG. 18 is a schematic diagram of an example of a support layer;

FIG. 19A is a schematic diagram of a section of another example of a wound dressing;

FIG. 19B is a perspective view of the wound dressing of FIG. 19A;

FIG. 20 is a schematic diagram of a further example of a wound dressing; and FIG. 21 is a schematic diagram of a yet further example of a wound dressing.

DETAILED DESCRIPTION

Embodiments disclosed herein relate to apparatuses and methods of treating a wound with or without reduced pressure, including optionally a source of negative pressure and wound dressing components and apparatuses. The apparatuses and components comprising the wound overlay and packing materials, if any, are sometimes collectively referred to herein as dressings.

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

As used herein a chronic wound is one that does not heal in an orderly set of stages and in a predictable amount of time the way most wounds do; wounds that do not heal within three months are often considered chronic. For example, a chronic wound may include an ulcer such as a diabetic ulcer, a pressure ulcer (or pressure injury), or venous ulcer.

Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds. Other embodiments do not utilize negative pressure for the treatment of wounds or other parts of the body.

Material or foam as herein defined is fluid absorbent, more particularly absorbent for aqueous fluids such as body fluids for example wound fluids and components thereof. Material or foam is liquid, gas and vapour permeable, for example permeable to said aqueous fluids, moisture and air. When applied to a locus, material aids in regulating moisture and air circulation at a locus. Said material suitably provides a moist environment such as a moist wound environment.

Preferably material or foam are hydrocellular, i.e. characterised by an ability to create a moist environment and absorb high amounts of fluid. A hydrocellular wound dressing material is characterised by an ability to create a moist wound healing environment and absorb high amounts of exudate.

Material or foam herein is a shaped or cast continuous or discontinuous body such as a block, layer, slab, mattress, pad, sheet, strip web or a roll thereof or the like, of regular or irregular shape. Material and matrix are non-particulate.

Antimicrobial material herein is suitably for use to inhibit or kill microbes selected from bacteria, yeast and fungi, thus is selected from antifungal, antibacterial, antiyeast, and in particular fungicidal, bactericidal and yeasticidal, fungistatic, bacteriostatic and/or yeastistatic and combinations. For the avoidance of doubt antimicrobial additive as hereinbefore defined is other than the antibiotic class of antimicrobials.

Antimicrobial material is envisaged for contact with aqueous media, such as aqueous fluid, at a locus, such as waste fluid, contaminated fluid, body fluid such as wound fluid and the like. A particularly suitable locus is moist.

Material herein may be medical material such as wound care material, dental material, personal care material, hygiene or sanitation material such as clothing material or upholstery material, food industry material, packaging material or the like. Material may be for use directly or comprised within a device.

Thus for example silver salts, and/or other additives advantageous for wound dressings, are loaded in porous foam useful to wound dressing. The resulting material may then be used in the manufacture of a wound dressing for application to a moist wound locus which may be exuding or non-exuding.

In embodiments said material applied to a wound locus absorbs exudate and particulate matter from the surface of granulating wounds and, as the material becomes moist, antimicrobial species such as ionic silver or diatomic and ionic iodine species is released. The material thus has the dual effect of cleansing the wound and exerting an antimicrobial action.

Material herein may be sterile or non-sterile, preferably terminally sterile or non-terminally sterile, for example may be sterilised by steam, gamma radiation, x-ray or electron beam or ethylene oxide.

Material herein may have thickness of 0.5 mm to 20 mm, more suitably 0.8 mm to 15 mm, preferably 1 mm to 12 mm, for example 2 mm, 3 mm, 4 mm, 5 mm or 6 mm. but may be of lesser or greater thickness if desired.

Foam herein may have pore size of 30 micron to 1000 micron, such as 30 micron to 700 micron or 300 micron to 1000 micron. A porous foam matrix herein preferably has pore size in the range 50 micron to 500 micron, for example 100 micron-250 micron or 200 micron-250 micron in average diameter. Foam may have any desired open pore architecture. Foam may have 20% to 70% of the total surface area of pores as openings. Foam is suitably of very high free internal volume, e.g. of the order of 70% to 90%.

Silver salt is suitably loaded in foam herein in an amount of 0.05 mg to 3.5 mg or 0.05 mg to 4 mg silver ion/$cm^2$ of material as herein defined, such as 0.1 mg to 3.5 mg or 4 mg silver ion/$cm^2$ of material as herein defined or 0.2 mg to 3.5 mg or 4 mg silver ion/$cm^2$ material as herein defined.

Additive may be provided herein in form of a powder charge including agents such as processing agents, for example flowing agent, bulking agent, viscosity modifier and the like.

Additive herein is commercially available and may be loaded as supplied or may be processed, for example by drying as hereinbefore defined or by selection of a desired particle size grade thereof, by methods known in the art or by novel methods herein.

Preferably additive has particle size compatible with manufacturing requirements, such as dosing requirements, or species availability requirements such as release parameters. Particle size for a highly soluble salt such as silver nitrate may be selected for manufacturing requirements such as dosing, for example may be of the order of 50-1000 micron, for example 50-200 micron such as 100 micron compatible with 200 micron pore size matrix. Particle size for low solubility additive may be selected for release parameters thereof such as optimised surface area, for example may be of the order of 8 micron<D90<115 micron, for example 4 micron<D50<60 micron, more preferably 1 micron<D10<30 micron or D50<10 micron. "Particle" size and distribution herein refers to primary particle size and distribution.

Additive may be provided in any suitable particle size and particle size distribution as commercially available, as supplied additive or by particle size reduction, suitably micronisation by methods known in the art or novel methods disclosed herein and in our copending unpublished U.K. Provisional Application No. 1711179.0, filed Jul. 12, 2017, the contents of which are incorporated herein by reference.

In embodiments additive comprised in a slurry phase or solid concentrate of isocyanate phase or part thereof is micronized and has L.O.D less than 0.5 wt % as hereinbefore defined, said micronizing according to novel methods of our unpublished U.K. Provisional Application No. 1711179.0, filed Jul. 12, 2017, the contents of which are incorporated herein by reference, for example comprising providing additive or powder charge and dry micronization thereof by particle collision selected from gas phase self-collision and collision with fluidised solid particles, such as contacting with gaseous or particulate milling force such as high speed air jet or high density milling beads or micro-beads.

One or more additives may be provided in said foam as herein defined for example selected from antimicrobial, bacterial, bacteriostatic, and the like and from device conditioning additives such as fireproofing powders or wound care dressing additives including conditioning additives such as odour control, protein-breaking, enhanced wicking, colour or masking, conductive, structure-supporting, enhanced absorbency, aqueous absorber such as super absorbent polymer (SAP), prevention of PU foam yellowing (optical brighteners, oxidation prevention), activated charcoal, etc., and the like.

For example charcoal has function as odour control agent or as colouring agent masking matrix discoloration in case of light sensitivity of silver salt or absorption of coloured aqueous media such as wound fluids, blood.

To prepare a typical foam 100 parts by weight of isocyanate such as Hypol FHP 2000, 2001, 3000, 3001, 2002 or 2000HD is mixed as herein defined with 0.3 to 7 parts by weight of surfactant or mixtures of surfactants and 30 to 300 parts by weight of water and from 0.3 or less to 50 or more parts by weight of powder charge or additive and the foaming mixture cast onto a surface. Typical foaming mixtures have a cream time of about 20 secs., a rise time of about 250 secs and a cure time of about 400 secs.

In a continuous process for forming the foam the ingredients are fed into a continuous mixing and dispensing·machine. Suitable conformable hydrophilic polymer foam layers can be made by casting the foaming mixture before it sets onto a suitable surface by means of a casting head.

A suitable mixing and dispensing machine is known as Vario-mix supplied by Prodef Engineering Limited. The foam mix can conveniently be delivered to the casting head by means of a 'fish tail' die.

The method is suitably a continuous method, and may be any variant of a method illustrated in FIG. 1, for example as illustrated in FIG. 2*a*-3*b* or variant thereof.

In FIG. 1 is illustrated a continuous process line up, providing respective isocyanate phase circuit and aqueous phase circuit by means of respective streams in respective supply lines each with recirculation facility which may be regulated for example in case of processing downtime to prevent congealing of phases in supply lines.

A Mixing Head (MH) is provided with line in from each of said Isocyanate Phase (IP) and Aqueous Phase (AP) supply lines and line out to a suitable surface such as a casting mould or liner. MH may include a casting head (illustrated) for casting mixed streams or may feed to a dedicated casting head.

In FIG. 2*a* is illustrated the same line up with additive conveyed as aqueous slurry phase AP-SP via Aqueous phase circuit to MH, with recirculation facility as in FIG. 1.

In FIG. 2*b* is illustrated the method of embodiments herein with additive conveyed as isocyanate slurry phase IP-SP via Isocyanate phase circuit to MH, with recirculation facility as in FIG. 1.

MH provides line out to casting mould (not shown) for mixed stream comprising additive, via CH to CF, as in FIG. 1. The process line up of FIG. 2*a* or 2*b* requires flushing or clean up of equipment including Isocyanate phase or Aqueous phase recirculation circuit, MH, CH and interconnecting lines, in the event of switching manufacture to foam having no additive or different additive.

In FIG. 3*a* is illustrated the method of embodiments herein with additive conveyed as slurry phase, solid concentrate or organic carrier liquid phase SP/SC/CL via feed line to isocyanate phase downstream of IP recirculation circuit, and upstream of Mixing Head MH, which may be by dedicated mixing head mh.iu and may be by one or more of IP lines into MH.

In FIG. 3*b* is shown the analogous method operated on aqueous side of the system. In FIGS. 3*a* and 3*b* MH provides line out to CH for mixed stream comprising additive, via CH to CF, as in FIG. 1.

The process line up of FIGS. 3*a* and 3*b* overcome the need to flush or clean up Isocyanate phase or Aqueous phase recirculation line or circuit for example in the event of switching manufacture to foam having no additive or different additive.

One or more feed lines or recirculation lines may be heated as known in the art for ease of conveying fluid therein.

In a preceding step said method comprises preparing a slurry phase or solid concentrate comprising dosing powder charge or additive to fluid with agitation to generate said slurry or solid concentrate. Preferably said method comprises determining an amount of powder charge or additive and a volume of liquid according to required slurry or solid concentrate viscosity, stability, homogeneity and the like. Preferably said method comprises dosing powder charge or additive having L.O.D as hereinbefore defined less than 0.5%, to said isocyanate phase or a part thereof. Advantageously powder charge or additive retains powder form, for optimum property such as release, absorbency or the like.

Advantageously dosing to a part of said aqueous phase or of said isocyanate phase permits maintaining additive-free recirculation circuit, with ease of cleaning and prevention of contamination.

Dosing additive or powder charge to a fluid for slurry or solid concentrate formation may be from a hopper, canister or reservoir of additive or of powder charge. Additive or powder charge is fluidised or fluid flow induced by entraining in an air jet or by flowing or pouring from a hopper or like reservoir.

Preferably said method comprises in a preceding step micronizing additive or powder charge as hereinbefore defined. Advantageously micronizing by dry particle collision as hereinbefore defined provides L.O.D as hereinbefore defined.

Material herein may be for use in applications at a locus selected from the management of wounds; hygiene and sterilisation of articles including medical and dental articles and point of use sterilisation; hygiene and sterilisation of personal care preparations and articles such as sanitary pads, diapers, cosmetics; hygiene and sterilisation of food or of fluids, including air and water, or systems for their preparation and generation such as food preparation or packaging plants, ventilation systems, water management systems; and in particular such uses for which preventing or combatting microbial infection is beneficial.

The material may be for application to wounds which carry a risk of presence of, contamination by or infection with microbes harmful to the health of said wound or of a subject, particularly selected from bacteria, yeast and fungi and combinations thereof.

Wound management includes management of shallow granulating wounds, chronic and acute exudative wounds, full and partial thickness wounds, exuding wounds, infected wounds, malignant wounds, surgically dehisced wounds, first and second degree burns, donor sites, fungating wounds and the like. Wounds for which the hereinbefore defined material has particular use include for example ulcers and pressure sores such as pressure ulcers, leg ulcers and diabetic foot ulcers; surgical wounds; trauma wounds; partial thickness burns; skin flap and skin graft donor site wounds; tunnelling and fistulae wounds; wounds left to heal by secondary intent; and wounds that are prone to bleeding such as wounds that have been surgically or mechanically debrided, cavity wounds, sinus and open wounds.

Material herein may be suitable for combatting Gram positive bacteria and/or Gram negative bacteria, for example Gram positive bacteria selected from *Staphylococcus* such as *Staph. aureus, Staph. epidermidis* and MRSA, *Streptococcus, Enterococcus, Corynebacterium* and *Clostridium* such as *C. difficile*, also *Peptostreptococcus, Lactobacillus, Propionibacterium, Bifidobacterium* and *Actinomyces* and/or Gram negative bacteria selected from proteobacteria such as Enterobacteriaceae for example, *Escherichia coli, Salmonella, Shigella, Pseudomonas* such as *Pseudomonas aeruginosa, Proteus, Klebsiella*, also *Legionella, Hemophilus, Neisseria, Acinetobacter* such as *A. baumannii, Bacteroides, Prevotella, Fusobacterium, Porphyromonas* and the cyanobacteria and spirochaetes.

Material herein is particularly useful in combatting one or more microbes encountered in a wound environment, for example Gram negative aerobic bacteria such as *Pseudomonas aeruginosa*, Gram positive bacteria such as *Staphylococcus aureus*, more particularly MRSA (methicillin resistant *Staphylococcus aureus*) also known as ORSA (oxacillin resistant *Staphylococcus aureus*), anaerobic bacteria such as

*Bacteroides fragilis*, yeast such as *Candida albicans* and fungi such as Aspergillis braziliansis.

Visualisation of Additive Surface Enrichment

In some embodiments, after said powder charge is dosed or loaded to said matrix as described herein, said matrix may exhibit heterogeneous spatial distribution of said powder charge and/or said additive. In some embodiments, the highest enrichment of the powder charge and/or said additive may present at one or more foam surface (e.g. the locus contacting face, the wound contacting face) and gradually decreases with increasing depth, subsurface into the bulk foam. In some embodiments, the powder charge and/or said additive may be homogeneously distributed.

The surface enrichment of the loaded additive, such as silver sulfate, may be visualised in 2-dimensions using backscatter Scanning Electron Microscopy (b-SEM) of planar cross-sectioned surfaces across the depth of the foam and in 3-dimensions using high resolution (instrument used must be capable of better than 35 micron spatial resolution) micro-focussed X-ray Computed Tomography (μ-XCT). The use of both visualisation techniques may be beneficial, because of the limits of spatial resolution of micro-focused X-ray Computed Tomography instruments. The matrix and loaded additive can be simultaneously visualised by both b-SEM and by μ-XCT.

In some embodiments, a 2-dimensional visualisation method such as micro Raman spectroscopy could be employed to map the spatial distribution of the loaded additive across a planar cross-sectioned surface of the foam. The polyurethane foam and the silver sulfate can be simultaneously mapped by micro Raman spectroscopy.

In some embodiments, a 2-dimensional visualisation method such as micro X-ray Fluorescence (μ-XRF) could be employed to map the spatial distribution of silver and sulphur (elemental constituents of silver sulfate) across a planar cross-sectioned surface of the foam, where such an elemental map is overlaid upon a macroscopic optical image of the mapped area (the polyurethane foam cannot be mapped by μ-XRF).

Quantification of Additive Surface Enrichment

Quantification of the extent of the additive enrichment can be achieved by means of image analysis based on greyscale segmentation (brightness of backscatter signal) of b-SEM images. Areas of interest located at different foam depths in the cross-sectional images can be analysed to obtain a 2D percentage area coverage of silver sulfate (silver sulfate yields brighter contrast than polyurethane foam in b-SEM images).

Quantification of the extent of silver sulfate enrichment can be achieved by means of image analysis based on greyscale segmentation (X-ray opacity) of μ-XCT images. Volumes of interest located at different foam depths in the 3-dimensional image datasets can be analysed to obtain a 3D percentage area occupation of silver sulfate within each subsequently deeper volume of interest (silver sulfate yields higher X-ray opacity than polyurethane foam in μ-XCT images).

Device

A device as hereinbefore defined comprises (a) a locus contacting surface or layer and/or (b) an opposing non-locus contacting surface or layer together with (c) an aqueous medium absorbing layer of material as hereinbefore defined comprised between or in combination with (a) and/or (b).

For example a device is a medical or dental sponge or wipe, or together with additional functional materials is a wound dressing.

In preferred devices herein, layer (a) and/or (b) are independently selected from silicone, polyurethane and the like.

A device herein may comprise same or different antimicrobial material as hereinbefore defined provided in a plurality of layers, for example 2 or 3 layers of asymmetric material may provide strata of antimicrobial additive within said device.

In this embodiment a device may comprise a modification of commercially available hydrophilic absorbent foam or multilayer presentation comprising absorbent polyurethane foam, woven or non-woven, fiber, film or membrane.

Antimicrobial material comprising polyurethane foam herein is useful as modification of commercially available dressings such as ALLEVYN™ foam, ALLEVYN™ Life, ALLEVYN™ Adhesive, ALLEVYN™ Gentle Border, ALLEVYN™ Gentle, ALLEVYN™ Ag Gentle Border, ALLEVYN™ Ag Gentle, PICO™ and other commercially available absorbent, hydrophilic polyurethane foams.

FIG. 7 illustrates wound dressing formats including polyurethane material herein. In FIGS. 5*a* and 5*b* are illustrated dressings comprising layers (a), (b) and (c) above. In FIG. 7*b*, layers are held together by heat laminating outer layers (a) and (c) at the borders thereof. FIG. 7*c* shows variant 7*b* including additional layers (b') and (b") above. FIG. 7*d* illustrates a variant of FIG. 7*a*, comprising a foam and fiber matrix bilayer. The bilayer may constitute a bilayered antimicrobial material as herein defined comprising a bilayer matrix component with powder charge component as herein defined. Alternatively the bilayer may constitute independent antimicrobial material layers either or both comprising a matrix component with powder charge component as hereinbefore defined.

A packaged device herein is suitably packaged in a water proof pouch such as an aluminium foil pouch.

In a further aspect there is provided herein a method of manufacture of a device herein.

In embodiments the previously formed individual layers may be formed into a laminate by bonding the layers together in one or more laminating processes. Suitable bonding methods include heat sealing or adhesive bonding providing the adhesive layer is moisture vapour transmitting.

In alternative embodiments the foam layer is formed in contact with one or both of the other layers or additional layers. This process may be favoured as it reduces or eliminates the number of special bonding operations.

In another preferred process the outer conformable film layer is formed on the foam layer for example by spraying a solution of the polymer.

In a continuous process the wound dressing can be made in the form of a continuous strip which is then cut up into suitable sized dressings.

Normally the bringing together of the layers will be a lamination process.

In a preferred process of forming the dressing in which the foam layer is produced in contact with an external layer it is important that the other external layer should be laminated to the expanded foam while the foam is still tacky so as to obtain a good bond. Typically 2.5 minutes to 5 minutes, for example 3 minutes to 3.5 minutes after the foam has been cast is suitable for bringing the foam into contact with the other external layer.

A method of treatment as hereinbefore defined is for treating a locus such as a wound. A suitable locus for treatment is moist or comprises aqueous fluid. Antimicrobial species release is activated into said locus or wound on contact with moisture or aqueous fluid. A suitable wound is exuding.

Preferably the method of treatment herein comprises additionally securing material or device herein in contact with said locus or wound. Suitably securing means is sufficiently robust to retain material or device in position for the required duration, for example 7, 8 or 10 days or more. Securing may be by adhesion to said locus, such as skin surrounding said wound, of locus contacting surface such as wound contacting surface, or of cover layer or of a further adhesive layer or strips or a bandage applied over said material or device.

Embodiments herein are illustrated as follows with reference to examples which are non-limiting thereof.

EXAMPLES

Comparative Example 1 Preparation of PU Foam Point of Manufacture (P.O.M.) Loaded with Silver Sulfate

Example CE1.1: P.O.M. Loaded (Aqueous)

PU foam sample comprising silver sulfate (Alfa Aesar, 40-70 micron) was prepared using a variant of method of EP0059049 Example 8, replacing aqueous silver sulfadiazine solution with aqueous silver sulfate solution:

Silver sulfate (1.5 g) was blended with a high speed shear mixer into a Brij 72 emulsion (30 g as a 2.5% aqueous solution).

The mixed emulsion-additive was added to Hypol 2002 (20 g) in a beaker and mixed by stirring with a metal spatula and then with a mechanical stirrer until the Hypol was uniformly dispersed (approximately 20 seconds) and cast to a shaped liner to produce foam with equivalent loading dose (TS) of 1.9 mg/cm$^2$. In SEM images of the resulting material, shown in FIGS. 1*a* and 1*b*, silver sulfate (bright spots) is seen loaded in pores (dark grey against grey cross sectioned structural matrix framework or grey cross sectioned cell surface) throughout the 2 mm thick foam showing loading of particles precipitated from solution in sub-micron size.

Example CE1.2: P.O.M. Loaded (Aqueous Suspension)

PU foam comprises silver sulfate loaded within the structural matrix framework from a combined solution suspension of silver sulfate combined in the aqueous phase of the polyurethane foam polymerisation reaction, as disclosed in European Patent EP1964580.

Comparative Example 2 Preparation of Multi-Layer Dressing Compositions Example CE1.1D (P.O.M. Loaded (Aqueous)

Foam of Comparative Example CE1.1 was provided together with breathable top film and adhesive wound contact layer in multi-layer dressing composition format as CE1.1D.

Example CE1.2D (P.O.M. Loaded (Aqueous Suspension)

Commercially available Mepilex® Border Ag (Moelnlycke Health Care) is multilayer dressing CE1.2D herein (format of FIG. 7*c*), comprising hydrocellular PU foam layer manufactured using methodology of Example CE1.2 (P.O.M loaded (aqueous suspension)) source of silver sulfate unknown, together with superabsorbent fibre layer, PU breathable top film and gentle adhesive wound contact layer with equivalent loading dose (TS) of 1.3 mg/cm$^2$. Silver sulfate is comprised as part precipitated/part suspension derived particles within the PU foam structural matrix framework throughout the depth of the foam in one population including 15 micron particles and a second population of approx. 1 micron fines.

Example 1 Preparation of PU Foam P.O.M (Isocyanate) Loaded

Example 1.1 Preparation of Slurry Phase or Solid Concentrate

Foams were produced on a lab-scale by dosing powder charge comprising silver sulfate (Alfa Aesar 40-70 micron), a very dense silver salt, d=5, and thoroughly blending into a Hypol 2002 (PEG-TDI prepolymer) "isocyanate" phase to generate a slurry of powder charge in "isocyanate".

Example 1.2 P.O.M Loading

The "isocyanate" slurry phase was added on a basis of 20 g isocyanate to a Brij 72 emulsion (30 g as a 2.5% aqueous solution "water" phase), thoroughly blended and cast onto a shaped liner, using the methodology of EP0059049 and Comparative Example 1 above.

Foams were prepared in a variety of concentrations from slurries in different silver sulfate loading as indicated in Table 1. Equivalent loading in isocyanate phase is given for CE1.2 for comparison purpose.

TABLE 1

Additive (silver sulfate) loading in polyurethane foam

| Example | Silver sulfate (wt %) in isocyanate phase slurry | Silver sulfate (wt %) in water phase | Equivalent loading expressed as wt % of isocyanate phase |
|---|---|---|---|
| CE1.2 | | 3.6 | 2.98 |
| Ex.1.1 | 3.3 | | |
| Ex.1.2 | 5 | | |
| Ex.1.3 | 6.7 | | |
| Ex.1.4 | 8.35 | | |

Foams of examples Ex. 1.1-1.4 were found by SEM analysis of two different loadings each in 3 samples, to be homogeneous in distribution of silver sulfate. FIG. 2 shows SEM of one sample of each of foam blocks derived from slurry of silver salt in Hypol 2002 at a) 6.7% and b) 3.35%. Bright spots show the location of the silver element.

The results demonstrated that additive introduced as slurry phase or solid concentrate in isocyanate phase does not affect foaming performance.

Example 1.3 Scale Mixing and Production 71 scale mixing trials were performed to assess the feasibility of mixing a silver salt into a viscous isocyanate pre-polymer phase and handling the resulting slurry. Foams were manufactured using the method of Example 1 in 71 scale and showed upheld homogeneity in cell dimension, and distribution of silver as illustrated in FIG. 6 (Left: Top of block, Middle: Middle of block, Right: Bottom of block. Bright spots show the location of silver sulfate).

Example 2 Preparation of Micronized Additive

Example 2.1 Micronisation

Silver sulfate (40-70 micron, Alfa Aesar), a very dense silver salt, d=5, was introduced into the inlet of air jet milling apparatus (Dietrich Engineering Consultants, Conika dry mill). Settings were adjusted (injection and grinding line gas pressures and silver sulfate feed rate) to reduce the median particle size to 1-10 micron. Powder charge was obtained in a number of grades.

Grade of samples of micronized silver sulfate was measured by Malvern Mastersizer after sonicating a dispersion of the powder in methanol, for example as follows:

D50~3 micron;

D50~6 micron;

D50~14 micron.

Micronized silver sulfate was also assessed for particle size distribution, by methods disclosed herein, for example as follows:

average 1.6 (0.4-5.3) micron;

average 1.9 micron (0.7-5 micron)

Example 2.2 Preparation of Slurry Phase or Solid Concentrate (Loss on Drying)

Powder charge was sampled for loss on drying testing before providing as slurry phase or solid concentrate, as follows:

Samples were weighed, placed into vacuum oven at 50° C. for 4 hours and subsequently reweighed. All samples gave loss on drying <0.1%.

Loss on drying is important for point of manufacture (P.O.M.) loading into PU foam via isocyanate phase, to reduce the likelihood of premature polymerisation. Loss on drying is important for P.O.M or composite loading into pre-formed PU foam to increase accuracy of dosing by weight.

Powder charge was dosed and blended into isocyanate phase for use in Example 1.1.

Example 3 Ageing and Stability of Isocyanate Slurry

The stability of the slurry prepared in Example 1.1 was studied over 3 months, when subjected to gentle mixing and maintained at a standard temperature to ensure the flowability of a Hypol phase. The results are shown in FIG. 7 as viscosity of Hypol 2002, with 0% and 6.7% silver sulphate, over 3 months when gently rotated at 40° C.

The viscosity of the silver salt mixture in Hypol, although higher than virgin Hypol, did not increase over time, showing that the system could be stable in a re-circulating line attached to a production process, without any blockage of lines and breakdown in pumping of isocyanate phase, incurred by self-polymerisation induced viscosity increase.

Example 4 Preparation of Multi-Layer Dressing Compositions

Foams of Ex. 1.1-1.4 were provided as the corresponding Ex. 1.1D-1.4D in a variety of multi-layer commercial dressing composition formats as illustrated in FIG. 8:

ALLEVYN Gentle Border: **8*b***

ALLEVYN Life: FIG. **8*c***

ALLEVYN Gentle: **8*b***, no border

ALLEVYN Life Non-Bordered: **8*c***, no border

Example 5 Silver Release Performance

Silver release was determined for multilayer compositions CE1.1D, CE1.2D and Ex. 1.1D-1.4D using methodology herein described, i.e. amount released into 50 mL of aqueous media given as mg/cm$^2$ of material per unit time. Release was cumulative with the same media sampled over 7 days, leading to slow saturation of that particular fluid. Results are shown in FIG. 9.

All 3 multilayer composition types, P.O.M (aqueous), P.O.M (aqueous suspension) and P.O.M (isocyanate) showed a bolus release in the first 6 hours, then reached steady state, with release continuing beyond 170 hours. As illustrated in FIG. 9, all dressing compositions gave a bolus release up to approx. 0.1 mg Ag ion/cm$^2$ in first 24 hours, and thereafter gave continued increase up to between 1.2 mg/cm$^2$ and 1.8 mg/cm$^2$. This compares with results for CE1.1D which gave bolus of less than 0.1 mg/cm$^2$ in first 24 hours, with continued increase up to less than 0.12 mg/cm$^2$.

Example 6 Antimicrobial Performance Different Dressing Composition Format

Different multilayer compositions Ex. 1.1D-1.4D were successfully submitted for testing against *S. aureus* and *P. aeruginosa* using known methods. Results of log kill against *S. aureus* are shown in FIG. 10 for the same format dressing composition in each case, in which D is the dressing CE1.2D, C being a simpler presentation of D omitting some internal layers, and E, F and G are samples of Ex. 1D in different silver sulfate particle sizes <10 micron, and different loadings (E & F Ex. 1.3D, G Ex. 1.1D). Results are mean values for testing from 3-6 samples.

Negative Pressure Wound Therapy (NPWT)

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (e.g., heartbeat). Examples of such applications where additional disclosure relating to the preceding may be found include U.S. Pat. No. 8,235,955, titled “Wound treatment apparatus and method,” issued on Aug. 7, 2012; and U.S. Pat. No. 7,753,894, titled “Wound cleansing apparatus with stress,” issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled “APPARATUSES AND METHODS FOR NEGATIVE PRESSURE WOUND THERAPY,” International Application No. PCT/IB2013/002060, filed on Jul. 31, 2013, published as WO2014/020440, entitled “WOUND DRESSING,” the disclosures of which are hereby incorporated by reference in their entireties. Embodiments of the wound dressings, wound treatment apparatuses and methods described herein may also be used in combination or in addition to those described in U.S. Pat. No. 9,061,095, titled “WOUND DRESSING AND METHOD OF USE,” issued on Jun. 23, 2015; and U.S. Application Publication No. 2016/0339158, titled “FLUIDIC CONNECTOR FOR NEGATIVE PRESSURE WOUND THERAPY,” published on Nov. 24, 2016, the disclosures of which are hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Publication No. WO 2016/174048 A1, entitled “REDUCED PRESSURE APPARATUSES”, published on Nov. 3, 2016, the entirety of which is hereby incorporated by reference. In some of these embodiments, the pump or associate electronic components may be integrated into the wound dressing to provide a single article to be applied to the wound.

Multi-Layered Wound Dressings

Any multi-layered wound dressings may incorporate or comprise a loaded matrix as hereinbefore described. Such wound dressings may incorporate a loaded matrix layer, composite or laminate including the loaded matrix. For example, a loaded foam layer including a powder charge/additive-loaded polyurethane (PU) material as described previously herein and illustrated in FIGS. 1-10 may be incorporated into a multi-layered wound dressing. As described previously herein, the powder charge or additive loaded onto the polyurethane (PU) material may be configured to be activated to release chemical species, for example, antimicrobial species by contact with moist or aqueous medium. Accordingly, the loaded matrix may be configured to release, for example, antimicrobial species upon contact with moist or aqueous medium, for example wound exudate. To facilitate release and diffusion of antimicrobial species into the wound, the loaded matrix may be placed proximate to the wound within the wound dressing.

In some embodiments, there is provided a method to treat a wound or locus. The method may include placing a multi-layered wound dressing having a loaded matrix, such as a fiber or foam layer including a powder charge/additive as described herein, over the wound, such that the wound dressing touches the wound. Examples of such wound dressings were described above and are further described hereinafter. The wound dressing may be adhered to healthy skin around the wound. The method may further include allowing wound exudate to reach and/or touch the loaded matrix layer. In some embodiments, negative pressure may be applied to the wound dressing, such that wound exudate is suctioned into the wound dressing. In some embodiments, the wound exudate may be diffused or wicked into the wound dressing. In some embodiments, any moist or aqueous medium other than wound exudate may be provided to the wound dressing. Upon contact with moist or aqueous medium, either provided by wound exudate or not, the loaded matrix layer may release antimicrobial species as described herein previously. At least a portion of the released antimicrobial species may be released into the wound, for example by diffusion. In some embodiments, the antimicrobial species may be silver ions. In some embodiments, the antimicrobial species may be released to the wound for a prolonged duration, for example, up to a day, five days, seven days or 10 days or more. In some embodiments, the silver ion may be released up to 0.1 $mg/cm^2$ per day, up to 1.2 $mg/cm^2$ per day, up to 1.8 $mg/cm^2$ per day or more.

Multi-Layered Wound Dressings for NPWT

FIG. 11 illustrates an example of a negative pressure wound therapy system 700. The system includes a wound cavity 710 covered by a wound dressing 720, which can be a dressing according to any of the examples described herein. The dressing 720 can be positioned on or inside the wound cavity 710 and further seal the wound cavity so that negative pressure can be maintained in the wound cavity. For example, a film layer of the wound dressing 720 can provide substantially fluid impermeable seal over the wound cavity 710. In some embodiments, a wound filler, such as a layer of foam or gauze, may be utilized to pack the wound. The wound filler may include a loaded matrix as hereinbefore described. For example, in a traditional negative pressure wound therapy system utilizing foam or gauze, such as the Smith & Nephew RENASYS Negative Pressure Wound Therapy System utilizing foam (RENASYS-F) or gauze (RENASYS-G), the foam or gauze may be replaced with or may be supplemented with a loaded matrix layer, composite or laminate as described above. When supplementing a foam or gauze layer or other wound packing material, the loaded matrix layer, composite or laminate may either be separately inserted into the wound or may be pre-attached with the wound packing material for insertion into the wound.

A single or multi lumen tube or conduit 740 connects the wound dressing 720 with a negative pressure device 750 configured to supply reduced pressure. The negative pressure device 750 includes a negative pressure source. The negative pressure device 750 can be a canisterless device (meaning that exudate is collected in the wound dressing and/or is transferred via the tube 740 for collection to another location). In some embodiments, the negative pressure device 750 can be configured to include or support a canister. Additionally, in any of the embodiments disclosed herein, the negative pressure device 750 can be fully or partially embedded in, mounted to, or supported by the wound dressing 720.

The conduit 740 can be any suitable article configured to provide at least a substantially sealed fluid flow path or pathway between the negative pressure device 750 and the wound cavity 710 so as to supply reduced pressure to the wound cavity. The conduit 740 can be formed from polyurethane, PVC, nylon, polyethylene, silicone, or any other suitable rigid or flexible material. In some embodiments, the wound dressing 720 can have a port configured to receive an end of the conduit 740. For example, a port can include a hole in the film layer. In some embodiments, the conduit 740 can otherwise pass through and/or under a film layer of the wound dressing 720 to supply reduced pressure to the wound cavity 710 so as to maintain a desired level of reduced pressure in the wound cavity. In some embodiments, at least a part of the conduit 740 is integral with or attached to the wound dressing 720.

FIGS. 12A-B illustrate embodiments of a negative pressure wound treatment system 10 employing a wound dressing 100 in conjunction with a fluidic connector 110. Additional examples related to negative pressure wound treatment comprising a wound dressing in combination with a pump as described herein may also be used in combination or in addition to those described in U.S. Pat. No. 9,061,095, which is incorporated by reference in its entirety. Here, the fluidic connector 110 may comprise an elongate conduit, more preferably a bridge 120 having a proximal end 130 and a distal end 140, and an applicator 180 at the distal end 140 of the bridge 120. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 12A-12B, the pump 150 can be a canisterless pump such as the PICO™ pump, as sold by Smith & Nephew. The pump 150 may be connected to the bridge 120 via a tube 190, or the pump 150 may be connected directly to the bridge 120. In use, the dressing 100 is placed over a suitably-prepared wound, which may in some cases be filled with a wound packing material such as foam or gauze as described above. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the bridge 120. The pump is then activated, thereby supplying negative pressure to the wound. Application of negative pressure may be applied until a desired level of healing of the wound is achieved.

As shown in FIG. 12C, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In a preferred embodiment, the head 140 may measure 30 mm along its widest edge. The head 140 forms at least in part the applicator 180, described above, that is configured to seal against a top surface of the wound dressing.

FIG. 12D illustrates a cross-section through a wound dressing 100 similar to the wound dressing 10 as shown in FIG. 12B and described in International Patent Publication WO2013175306 A2, which is incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 12D, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A transmission layer 226 can be located above the wound contact layer 222. In some embodiments, the transmission layer can be a porous material. As used herein the transmission layer can be referred to as a spacer layer and the terms can be used interchangeably to refer to the same component described herein. This transmission layer 226 allows transmission of fluid including liquid and gas away from a wound site into upper layers of the wound dressing. In particular, the transmission layer 226 preferably ensures that an open-air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three-dimensional structure. For example, a knitted or woven spacer fabric (for example Baltex 7970 weft knitted polyester) or a non-woven fabric could be used. The three-dimensional material can comprise a 3D spacer fabric material similar to the material described in International Publication WO 2013/175306 A2 and International Publication WO2014/020440, the disclosures of which are incorporated by reference in their entireties.

The wound dressing 100 may incorporate or comprise a loaded matrix as hereinbefore described. For example, a loaded foam layer including a powder charge/additive-loaded polyurethane (PU) material or fibre material as described previously herein and illustrated in FIGS. 1-10 may be incorporated into the wound dressing 100. In some embodiments, the loaded matrix layer may be provided below the transmission layer 226. In some embodiments, the loaded matrix layer may be provided above the wound contact layer 222. In some embodiments, the loaded matrix layer may replace the transmission layer 226, such that the loaded matrix layer is provided between an absorbent layer 221 (described further below) and the wound contact layer 222. In some embodiments, the loaded matrix layer can supplement or replace the absorbent layer 221, or the absorbent layer 221 can be loaded with powder charge as described above. In some embodiments, the wound dressing 100 does not have the wound contact layer 222, and the loaded matrix layer may be the lowermost layer of the wound dressing 100. The loaded matrix may have same or substantially similar size and shape with the transmission layer 226 and/or the absorbent layer 221.

The loaded matrix layer may be constructed to be flexible but stiff enough to withstand negative pressure, such that the loaded matrix is not collapsed excessively and thereby transmits negative pressure sufficiently to the wound when negative pressure is supplied to the wound dressing 100. The loaded matrix layer may be constructed to include sufficient number or size of pores to enable transmission of negative pressure through it. Further, the loaded matrix layer may have suitable thickness to transmit enough negative pressure to the wound. For example, the loaded matrix layer may have a thickness of 1 mm to 5 mm, 1.5 mm to 4 mm, or 2 mm to 3 mm. In some embodiments, the loaded foam matrix may have a thickness of approximately 2 mm.

In some embodiments, the layer 221 of absorbent material is provided above the transmission layer 226. The absorbent material, which can comprise a foam or non-woven natural or synthetic material, and which may optionally comprise a super-absorbent material, forms a reservoir for fluid, particularly liquid, removed from the wound site. In some embodiments, the layer 221 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 or Chem-Posite™ M11C-450. In some embodiments, the absorbent layer 221 may comprise a composite comprising superabsorbent powder, fibrous material such as cellulose, and bonding fibers. In a preferred embodiment, the composite is an air-laid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Optionally, the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 12D a single through hole can be used to produce an opening underlying the fluidic connector 110. It will be appreciated that multiple openings could alternatively be utilized. Additionally, should more than one port be utilized according to certain embodiments of the present disclosure one or multiple openings may be made in the absorbent layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226 as illustrated in FIG. 12D. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described with reference to FIGS. 16A-16B and in International Patent Publication WO2014/020440, the entirety of which is hereby incorporated by reference, may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way, an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments, the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIGS. 12C-12D, the absorbent layer 221 may define a smaller perimeter than that of the backing layer 220, such that a boundary or border region is defined between the edge of the absorbent layer 221 and the edge of the backing layer 220.

As shown in FIG. 12D, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

In particular for embodiments with a single fluidic connector 110 and through hole, it may be preferable for the fluidic connector 110 and through hole to be located in an off-center position as illustrated in FIG. 12C. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Similar to the embodiments of wound dressings described above, some wound dressings comprise a perforated wound contact layer with silicone adhesive on the skin-contact face and acrylic adhesive on the reverse. In some embodiments, the wound contact layer may be constructed from polyurethane, polyethylene or polyester. Above this bordered layer sits a transmission layer. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Multi-Layered Dressing for Use Without Negative Pressure

FIGS. 13A-13D illustrates various embodiments of a wound dressing 500 that can be used for healing a wound without negative pressure. FIG. 13E illustrates a cross-section of the wound dressing in FIGS. 13A-13D, which is similar to the structure of FIG. 5*c*. As shown in the dressings of FIGS. 13A-13E, the wound dressings can have multiple layers similar to the dressings described with reference to FIGS. 12A-D except the dressings of FIGS. 13A-E do not include a port or fluidic connector. The wound dressings of FIGS. 13A-E can include a cover layer 501 and an optional wound contact layer 505 as described herein. In some embodiments, the cover layer 501 may be permeable to moisture and/or air. The wound dressing can include various layers positioned between the wound contact layer 505 and cover layer 501. For example, the dressing can include one or more absorbent layers or one or more transmission layers as described herein with reference to FIGS. 12A-D.

As shown in FIGS. 13A-13E, the dressing 500 includes a perforated wound contact layer 505 and a top film 501. Further components of the wound dressing 500 include a foam layer 504, such as a layer of polyurethane hydrocellular foam, of a suitable size to cover the recommended dimension of wounds corresponding to the particular dressing size chosen. An optional layer of activated charcoal cloth (not shown) of similar or slightly smaller dimensions than layer 504 may be provided to allow for odour control. An absorbent layer 502, such as a layer of superabsorbent air-laid material containing cellulose fibres and a superabsorbent polyacrylate particulates, is provided over layer 504, of dimensions slightly larger than layer 504, and allows allow for an overlap of superabsorbent material and acts as leak prevention. A masking or obscuring layer 503, such as a layer of three-dimensional knitted spacer fabric, is provided over layer 502, providing protection from pressure, while allowing partial masking of the top surface of the superabsorber where coloured exudate would remain. In this embodiment this is of smaller dimension (in plan view) than the layer 502, to allow for visibility of the edge of the absorbent layer, which can be used by clinicians to assess whether the dressing needs to be changed.

The wound dressing 500 may incorporate or comprise a loaded matrix as hereinbefore described. For example, a loaded foam or fibre layer including a powder charge/additive as described previously herein and illustrated in FIGS. 1-10 may be incorporated into the wound dressing 500. In some embodiments, the loaded matrix layer may be provided below the cover layer 501. In some embodiments, the loaded matrix layer may be provided above the wound contact layer 505. In other embodiments, the dressing 500 may not include the wound contact layer 505, such that the loaded matrix layer may be the lowermost layer and be configured to touch the wound surface. In some embodiments, the loaded matrix layer may be provided below the foam layer 504. In some embodiments, the loaded matrix layer may replace the foam layer 504.

As described previously herein, a loaded matrix, and for example a loaded foam including an antibacterial powder charge/additive-loaded polyurethane (PU) material, may be incorporated into commercially available dressings, such as ALLEVYN™ foam, ALLEVYN™ Life, ALLEVYN™ Adhesive, ALLEVYN™ Gentle Border, ALLEVYN™ Gentle, ALLEVYN™ Ag Gentle Border, ALLEVYN™ Ag Gentle. In some embodiments, the wound dressing 500 may include the cover layer 501 and the loaded foam layer placed below the cover layer 501 and configured to be placed over the wound, similarly with the wound dressing format described previously herein in relation to FIG. 5*a*. The loaded foam layer may include an adhesive such that the foam layer may be attached to healthy skin around the wound. In some embodiments, the wound dressing 500 may include the cover layer 501, the wound contact layer 505 and the loaded foam layer sandwiched therebetween, similarly with the wound dressing format described previously herein relation to FIG. 5*b*. In some embodiments, the wound dressing 500 may include the cover layer 501, the absorbent layer 502, the loaded foam layer below the absorbent layer 502, and the wound contact layer 505, similarly with the wound dressing format described previously herein relation to FIG. 5*c*.

Further details regarding wound dressings t that may be combined with or be used in addition to the embodiments described herein, are found in U.S. Pat. No. 9,877,872, issued on Jan. 30, 2018, titled "WOUND DRESSING AND METHOD OF TREATMENT," the disclosure of which are hereby incorporated by reference in its entirety, including further details relating to embodiments of wound dressings, the wound dressing components and principles, and the materials used for the wound dressings.

Multilayered Wound Dressing with an Integrated Source of Negative Pressure

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. Additionally, some embodiments related to wound treatment comprising a wound dressing described herein may also be used in combination or in addition to those described in International Application WO 2016/174048 and International Patent Application PCT/EP2017/055225, filed on Mar. 6, 2017, entitled "WOUND TREATMENT APPARATUSES AND METHODS WITH NEGATIVE PRESSURE SOURCE INTEGRATED INTO THE WOUND DRESSING," the disclosure of which is hereby incorporated by reference in its entirety herein, including further details relating to embodiments of wound dressings, the wound dressing components and principles, and the materials used for the wound dressings and wound dressing components.

In some embodiments, the pump and/or other electronic components can be configured to be positioned adjacent to or next to the absorbent and/or transmission layers in the wound dressing so that the pump and/or other electronic components are still part of a single apparatus to be applied to a patient with the pump and/or other electronics positioned away from the wound site. FIGS. 14A-14B illustrates a wound dressing incorporating the source of negative pressure and/or other electronic components within the wound dressing. FIGS. 14A-14B illustrates a wound dressing 1200 with the pump and/or other electronics positioned away from the wound site. The wound dressing can include an electronics area 1261 and an absorbent area 1260. The dressing can comprise a wound contact layer (not shown) and a moisture vapor permeable film or cover layer 1213 positioned above the contact layer and other layers of the dressing. The wound dressing layers and components of the electronics area as well as the absorbent area can be covered by one continuous cover layer 1213 as shown in FIGS. 14A-14B.

The electronics area 1261 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 1261 can include a button or switch 1211 as shown in FIG. 14A-14B. The button or switch 1211 can be used for operating the pump (e.g., turning the pump on/off).

The absorbent area 1260 can include an absorbent material 1212 and can be positioned over the wound site. The electronics area 1261 can be positioned away from the wound site, such as by being located off to the side from the absorbent area 1260. The electronics area 1261 can be positioned adjacent to and in fluid communication with the absorbent area 1260 as shown in FIGS. 14A-14B. In some embodiments, each of the electronics area 1261 and absorbent area 1260 may be rectangular in shape and positioned adjacent to one another.

In some embodiments, additional layers of dressing material can be included in the electronics area 1261, the absorbent area 1260, or both areas. In some embodiments, the dressing can comprise one or more spacer or transmission layers and/or one or more absorbent layers positioned above the contact layer and below the wound cover layer 1213 of the dressing.

The dressing can comprise a wound contact layer (not shown), a transmission layer (not shown), an absorbent layer 1212 over the transmission layer, a moisture vapor permeable film or cover layer 1213 positioned above the wound contact layer, transmission layer, absorbent layer, or other layers of the dressing. The wound contact layer can be configured to be in contact with the wound. The wound contact layer can include an adhesive on the patient facing side for securing the dressing to the surrounding skin or on the top side for securing the wound contact layer to a cover layer or other layer of the dressing. In operation, the wound contact layer can be configured to provide unidirectional flow so as to facilitate removal of exudate from the wound while blocking or substantially preventing exudate from returning to the wound. The one or more transmission layers assist in distributing negative pressure over the wound site and facilitating transport of wound exudate and fluids into the wound dressing. In some embodiments, the transmission layer can be formed at least partially from a three-dimensional (3D) fabric. Further, an absorbent layer (such as layer 1212) for absorbing and retaining exudate aspirated from the wound can be utilized. In some embodiments, a superabsorbent material can be used in the absorbent layer 1212. In some embodiments, the absorbent includes a shaped form of a superabsorber layer. The wound dressing layers of the electronics area and the absorbent layer can be covered by one continuous cover layer 1213. In some embodiments, the cover layer can include a moisture vapor permeable material that prevents liquid exudate removed from the wound and other liquids from passing through, while allowing gases through.

FIG. 14C illustrates an embodiment of layers of a wound dressing with the pump and electronic components offset from the absorbent area of the dressing. As illustrated in FIG. 14C, the dressing can include a wound contact layer 1310 for placing in contact with the wound. Lower spacer or transmission layers 1311 and 1311' are provided above the wound contact layer 1310. In some embodiments, the transmission layer 1311 can be a separate layer from spacer layer 1311' as shown in FIG. 14C. The lower transmission layers 1311 and/or 1311' can assist in distributing pressure evenly to the wound surface and/or wicking fluid away from the wound. An absorbent layer 1322 can be positioned above the lower transmission layer 1311. A dressing layer 1351 can include cutouts or recesses 1328 for embedding the electronic components 1350 within the layer 1351. In some embodiments, the cutouts or recesses 1328 can be sized and shaped to embed a pump 1327, power source 1326, and/or other electronic components. In some embodiments, the layer 1351 can include multiple spacer or transmission layers stacked together. In some embodiments, the layer 1351 can include multiple spacer or transmission layers pieced together to surround the electronic components 1350. An upper transmission layer 1317 can be provided above the absorbent layer 1322, layer 1351, and/or electronic components 1350.

The wound dressing 1200, 1300 may incorporate or comprise a loaded matrix as hereinbefore described. For example, a loaded foam or fibre layer including a powder charge/additive as described previously herein and illustrated in FIGS. 1-10 may be incorporated into the wound dressing. In some embodiments, the loaded matrix layer may be provided below the transmission layer 1311. In some embodiments, the loaded matrix layer may be provided below the wound contact layer 1310. In some embodiments, the loaded matrix layer may replace the transmission layer 1311, 1311' such that the loaded matrix layer is provided between an absorbent layer 1322 and the wound contact layer 1310. In some embodiments, the loaded matrix layer can supplement or replace the absorbent layer 1212, 1322, or the absorbent layer 1212, 1322 can be loaded with powder charge as described above. In some embodiments, the loaded matrix layer may be the lowermost layer of the wound dressing. The loaded matrix layer may have same or substantially similar size and shape with the transmission layers and/or the absorbent layers hereinbefore described.

The loaded matrix layer may be constructed to be flexible but stiff enough to withstand negative pressure, such that the loaded foam is not collapsed excessively and thereby transmits negative pressure sufficiently to the wound when negative pressure is supplied to the wound dressing 1200. The loaded matrix layer may be constructed to include sufficient number or size of pores to enable transmission of negative pressure through it. Further, the loaded matrix layer may have suitable thickness to transmit enough negative pressure to the wound. For example, the loaded matrix layer may have a thickness of 1 mm to 5 mm, 1.5 mm to 4 mm, or 2 mm to 3 mm. In some embodiments, the loaded matrix layer may have a thickness of approximately 2 mm.

A cover layer or backing layer 1313 can be positioned over the upper transmission layer 1317. The backing layer 1313 can form a seal to the wound contact layer 1310 at a perimeter region enclosing the transmission layers 1311, 1311', and 1317, the absorbent layer 1322, layer 1351, and electronic components 1350. In some embodiments, the backing layer 1313 can be a flexible sheet of material that forms and molds around the dressing components when they are applied to the wound. In other embodiments, the backing layer 1313 can be a material that is preformed or premolded to fit around the dressing components as shown in FIG. 14C.

Multi-Layered Wound Dressings for NPWT with a Wrapped Around Transmission Layer

FIG. 15A illustrates an embodiment of a TNP wound treatment device comprising a wound dressing. As stated above, the wound dressing 400 can be any wound dressing embodiment disclosed herein or have any combination of features of any number of wound dressing embodiments disclosed herein. For example, the wound dressing 400 may be similar to a PICO single unit dressing available from Smith & Nephew as described previously. The wound dressing 400 and associated system may also be similar to the system described in FIGS. 12A-12D previously. Embodiments of the wound dressings, wound dressing components, wound treatment apparatuses and methods described herein and with reference to FIGS. 15A-15C may also be used in combination or in addition to those described in International Publication No. WO 2017/114745 A1, published Jul. 6, 2017, titled "NEGATIVE PRESSURE WOUND THERAPY APPARATUS," the disclosure of which is hereby incorporated by reference in its entirety.

The dressing 400 may be placed over a wound, and a port 460 (which together with conduit 401 may form a fluidic connector as described with respect to FIGS. 12A-12D) may be used to provide negative pressure from a vacuum source to the wound. In the embodiment shown in FIG. 12A the dressing 400 may be provided with at least a portion of the conduit 401 pre-attached to the port 460. For example, the port/conduit combination may be a flexible suction adapter as described herein with reference to FIGS. 12A-12D. In some embodiments, the pre-attached conduit 401 can connect to a conduit extension, for example, a tubing (not shown). Preferably, the dressing 400 is provided as a single article with all wound dressing elements (including the port 460 and conduit 401) pre-attached and integrated into a single unit. The wound dressing 400 may then be connected, via the conduit 401 and/or conduit extension, to a source of negative pressure such as the pump as described with reference to FIGS. 12A-12D.

The cover layer 430, 320, which can be more clearly seen in FIG. 15B-15C, can be formed of substantially fluid impermeable material, such as film. The cover layer 430, 320 can be similar to the cover layer or backing layer described in FIGS. 12A-12D previously. The film may be transparent, such that from the top view of FIG. 15A, other layers underneath the cover layer are also visible. The cover layer can include an adhesive for securing the dressing to the surrounding skin or a wound contact layer. The dressing can utilize a wound contact layer 440, 322 and an absorbent layer 450, 321 within the dressing. The wound contact layer and the absorbent layer can be similar to the wound contact layer and absorbent layers described in FIGS. 12A-12D previously. The wound contact layer can be configured to be in contact with the wound. The wound contact layer can include an adhesive on the patient facing side for securing the dressing to the surround skin or on the top side for securing the wound contact layer 440, 322 to a cover layer 430, 320 or other layer of the dressing. In operation, in some embodiments the wound contact layer can be configured to provide unidirectional flow so as to facilitate removal of exudate from the wound while blocking or substantially preventing exudate from returning to the wound. Further, an absorbent layer (such as layer 450, 321) for absorbing and retaining exudate aspirated from the wound can be utilized. In some embodiments, the absorbent layer can include an absorbent material, for example, a superabsorbent material or other absorbent material known in the art. In some embodiments, the absorbent layer can include a shaped form of a superabsorber layer with recesses or compartments for the pump, electronics, and accompanying components. In some embodiments, the wound dressing can include multiple absorbent layers.

The absorbent material 450 as shown in FIG. 15A which may be a foam or non-woven natural or synthetic material and which may optionally include or be super-absorbent material, forms a reservoir for fluid, particularly liquid, removed from the wound site and draws those fluids towards a cover layer 430. The material of the absorbent layer can be similar to the absorbent material described with reference to FIGS. 12A-12D. The material of the absorbent layer also prevents liquid collected in the wound dressing from flowing in a sloshing manner. The absorbent layer 450 also helps distribute fluid throughout the layer via a wicking action so that fluid is drawn from the wound site and stored throughout the absorbent layer. This helps prevent agglomeration in areas of the absorbent layer.

In some embodiments, the absorbent layer 450 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. Also, all regions of the absorbent layer are provided with liquid.

The wicking action also assists in bringing liquid into contact with the upper cover layer to aid increase transpiration rates of the dressing.

The wicking action also assists in delivering liquid downwards towards the wound bed when exudation slows or halts. This delivery process helps maintain the transmission layer or lower spacer layer and lower wound bed region in a moist state which helps prevent crusting within the dressing (which could lead to blockage) and helps maintain an environment optimized for wound healing.

In some embodiments, the absorbent layer 450 may be an air-laid material. Heat fusible fibers may optionally be used to assist in holding the structure of the pad together. It will be appreciated that rather than using super-absorbing particles or in addition to such use, super-absorbing fibers may be utilized according to certain embodiments of the present invention. An example of a suitable material is the Product Chem-Posite™ 11 C available from Emerging Technologies Inc (ETi) in the USA.

Optionally, according to certain embodiments of the present invention, the absorbent layer 450 may include synthetic stable fibers and/or bi-component stable fibers and/or natural stable fibers and/or super-absorbent fibers. Fibers in the absorbent layer may be secured together by latex bonding or thermal bonding or hydrogen bonding or a combination of any bonding technique or other securing mechanism. In some embodiments, the absorbent layer is formed by fibers which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer 450 may comprise a layer of multiple fibers. Preferably, the fibers are strand-like and made from cellulose, polyester, viscose or the like. Preferably, dry absorbent particles are distributed throughout the absorbent layer ready for use. In some embodiments, the absorbent layer comprises a pad of cellulose fibers and a plurality of super absorbent particles. In additional embodiments, the absorbent layer is a non-woven layer of randomly orientated cellulose fibers.

Super-absorber particles/fibers may be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc.

Preferably, the particles of superabsorber are very hydrophilic and grab the fluid as it enters the dressing, swelling up on contact. An equilibrium is set up within the dressing core whereby moisture passes from the superabsorber into the dryer surrounding area and as it hits the top film the film switches and the fluid vapor starts to be transpired. A moisture gradient is established within the dressing to continually remove fluid from the wound bed and ensure the dressing does not become heavy with exudate.

The absorbent layer 450 can include at least one through hole. The through hole can be located so as to underlie the suction port as described with reference to FIG. 12D. A single through hole can be used to produce an opening underlying the port 460 (not shown in FIG. 15B). It will be appreciated that multiple openings could alternatively be utilized. Additionally, should more than one port be utilized according to certain embodiments of the present invention one or multiple openings may be made in the super-absorbent layer in registration with each respective port. Although not essential to certain embodiments of the present invention the use of through holes in the super-absorbent layer provide a fluid flow pathway which is particularly unhindered and this is useful in certain circumstances.

Use of one or more through holes in the absorption layer 450 also has the advantage that during use if the absorbent layer contains a gel forming material, such as superabsorber, that material as it expands to absorb liquid, does not form a barrier through which further liquid movement and fluid movement in general cannot pass. In this way each opening in the absorbent layer provides a fluid pathway between the lower transmission or spacer layer and the upper transmission or spacer layer to the wound facing surface of the filter and then onwards into the interior of the port.

These layers can be covered with one layer of a film or cover layer 430. The cover layer can include a filter that can be positioned over the absorbent layer, or a filter may be incorporated in the port 460 as described in International Application Publication No. WO 2013/175306 A2, U.S. Publication No. US2011/0282309, and U.S. Publication No. 2016/0339158 the entirety of which is hereby incorporated by reference. As shown in FIG. 7A gas impermeable, but moisture vapor permeable, cover layer 430 extends across the width of the wound dressing. The cover layer may be similar to the cover layer or backing layer described with reference to FIG. 12A-12D. The cover layer 430, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer and a wound site where a negative pressure can be established. The cover layer 430 is sealed to the wound contact layer 440 in a border region 410 around the circumference of the dressing, ensuring that no air is drawn in through the border area, for example via adhesive or welding techniques. The cover layer 430 protects the wound from external bacterial contamination (bacterial barrier) and allows liquid from wound exudates to be transferred through the layer and evaporated from the film outer surface. The cover layer 430 typically comprises two layers: a polyurethane film and an adhesive pattern spread onto the film. The polyurethane film is moisture vapor permeable and may be manufactured from a material that has an increased water transmission rate when wet.

The cover layer can include an aperture within the cover layer for providing fluid communication with a source of negative pressure or pump. The filter can be positioned in communication with the aperture in the wound cover4 430. The aperture in the wound cover 430 can be covered by a port 460. In some embodiments, the port 460 connects to a conduit for communication with a negative pressure source or pump. The port 460 can include a filter 420 provided to cover the aperture in the cover layer 430. In some embodiments, the filter 420 can be integral to the port 460. The filter 420 can include hydrophobic material to protect the pump and/or other components from liquid exudates. The filter 420 can block fluids while permitting gases to pass through. In some embodiments, the filter can be similar to the filter or filter system described in FIGS. 12A-12D previously. In some embodiments, the aperture in the cover layer 430 and the port 460 provide fluid communication between the wound dressing and a pump. In some embodiments, the pump, electronics, switch and battery can be positioned at a remote location from the dressing. In some embodiments, the pump, electronics, switch and battery can be positioned on top of the first cover layer and a second filter and second cover layer can be alternative or additionally used. For example, the second filter can be constructed from antibacterial and/or antimicrobial materials so that the pump can exhaust gases into the atmosphere. The second filter can also help to reduce noise produced by the pump.

Negative pressure can be lost at the wound bed when free absorbent capacity remains in the dressing. This can occur because some or all of the pores in the filter are blocked with liquid or particulates. In some embodiments, solutions are utilized to allow the full capacity of the dressing absorbent layer to be utilized whilst maintaining the air path between the source of negative pressure and the wound bed.

In dressing embodiments that utilize a cover layer directly over the absorbent layer the dressing can have a void underneath the filter which can fill with liquid, thus blocking the filter pores and preventing air flow to the wound bed. A spacer layer or transmission layer 490 can be used to provide a fluid flow path above the absorbent layer 450 preventing the blocking of the port 460. In some embodiments, the transmission layer 490 in the dressing can be provided above and below the absorbent layer. The transmission layer can be incompressible and maintain a path for fluid flow between the source of negative pressure and the wound bed, via the filter. In some embodiments, the transmission layer can encapsulate or wrap around the absorbent layer as shown in FIGS. 15A and 15B. The wrapped transmission layer can provide an uninterrupted length of transmission material from the filter 420 to the wound bed. The transmission layer can traverse the length of the top surface of the absorbent layer and wrap around at least one side of the absorbent layer and traverse the length of the bottom surface (wound facing surface) of the absorbent layer. In some embodiments, the transmission layer can wrap around two sides of the absorbent layer as shown in FIG. 15A.

In some embodiments, the transmission layer can be utilized to assist in distributing negative pressure over the wound site and facilitating transport of wound exudate and fluids into the wound dressing.

A lower portion of the transmission layer 490 of porous material can be located above the wound contact layer and below the absorbent layer and wrapped around the edges of the absorbent layer. As the transmission layer is wrapped around at least one edge of the absorbent layer, the transmission layer has an upper portion of the transmission layer that can be positioned between the cover layer and the absorbent layer. As used herein the edge of the absorbent layer or the dressing refers to the sides of the material that are substantially perpendicular to the wound surface and run along the height of the material.

In some embodiments, the transmission layer can be a porous layer. This spacer layer, or transmission layer 490 allows transmission of fluid including liquid and gas away from a wound site into upper layers of the wound dressing as described with reference to FIG. 12D. In particular, the transmission layer 490 ensures that an open-air channel can be maintained to communicate negative pressure over the wound area even when the absorbent layer has absorbed substantial amounts of exudates. The layer should remain open under the typical pressures that will be applied during negative pressure wound therapy as described previously, so that the whole wound site sees an equalized negative pressure. The transmission layer 490 may be formed of a material having a three-dimensional structure. For example, a knitted or woven spacer fabric (for example Baltex 7970 weft knitted polyester) or a non-woven fabric could be used. Other materials, such as those described previously herein, could of course be utilized.

The wound dressing 400 may incorporate or comprise a loaded matrix as hereinbefore described. For example, a loaded foam or fibre layer including a powder charge/additive as described previously herein and illustrated in FIGS. 1-10 may be incorporated into the wound dressing 400. In some embodiments, the loaded matrix layer may be provided below the transmission layer 490. In some embodiments, the loaded matrix layer may be provided above the wound contact layer 440. In some embodiments, the loaded matrix layer may replace all or part of the transmission layer 490, for example such that the loaded matrix layer wraps around the edges of the absorbent layer 450 (described further below) and the wound contact layer 440. In some embodiments, the loaded matrix layer can supplement or replace the absorbent layer 450, or the absorbent layer 450 can be loaded with powder charge as described above.

The loaded matrix layer may be constructed to be flexible but stiff enough to withstand negative pressure, such that the loaded matrix is not collapsed excessively and thereby transmits negative pressure sufficiently to the wound when negative pressure is supplied to the wound dressing 400. The loaded matrix layer may be constructed to include sufficient number or size of pores to enable transmission of negative pressure through it. Further, the loaded matrix layer may have suitable thickness to transmit enough negative pressure to the wound. For example, the loaded foam layer may have a thickness of 1 mm to 5 mm, 1.5 mm to 4 mm, or 2 mm to 3 mm. In some embodiments, the loaded matrix layer may have a thickness of approximately 2 mm.

Providing the transmission layer between the port and the absorbent layer prevents fluid or exudate removed from the wound from blocking the port and/or filter within the port. There can be some free particles in the hole of the absorbent layer positioned below the filter. The loose free particles in the hole can gel and block the hole and/or filter area. Therefore, the upper transmission layer can keep the superabsorber particles clear from the filter and allow the dressing to fill completely. In some embodiments, the transmission layer wrapped around the absorbent layer allow the port to be located at any location with respect to gravity. The transmission layer positioned above the absorbent layer can eliminate the concerns of the fluid or exudate removed from the wound from blocking the port and/or filter within the port on the section of the absorbent layer that is filled first.

As shown in FIG. 15C, a wound dressing 300 can include a wound contact layer 322. The wound contact layer 322 can be similar to the wound contact layer 225 described with reference to FIG. 12D. In some embodiments, the wound contact layer 322 can be a double-face coated (silicone-acrylic) perforated adhesive wound contact layer. A transmission layer 326*a* and absorbent layer 321 can be provided similar to the dressing described with reference to FIG. 12D but the transmission layer 326*a* over-borders the absorbent layer. The wound dressing 300 can include a second transmission layer 326*b* between the absorbent layer and the backing layer that over-borders the absorbent layer. The first and second transmission layers 326*a* and 326*b* can over-border the absorbent layer by 5 mm at the perimeter. This can be the reverse of the cut geometry in the dressings as described previously. In some embodiments, there is no through-hole or aperture in the absorbent layer 321 or second transmission layer 326*b*. In some embodiments, the hole in the absorbent layer could be disadvantageous because it could become filled with superabsorbent particles or other material and block the filter in the standard dressing. A backing layer 320 sits over the second transmission layer 326*b* and the backing layer can include an orifice 327 that allows connection of the fluidic connector to communicate negative pressure to the dressing. In some embodiments, the first and second transmission layer 326*a*, 326*b* can include a 3D fabric.

The wound dressing 300 may incorporate or comprise a loaded matrix as hereinbefore described. For example, a loaded foam or fibre layer including a powder charge/additive as described previously herein and illustrated in FIGS. 1-10 may be incorporated into the wound dressing 300. In some embodiments, the loaded matrix layer may be provided below the first transmission layer 326*a*. In some embodiments, the loaded matrix layer may be provided above the wound contact layer 322. In some embodiments, the loaded matrix layer may replace the first transmission layer 326*a*. In some embodiments, the loaded matrix layer can supplement or replace the absorbent layer 321, or the absorbent layer 321 can be loaded with powder charge as described above.

The loaded matrix layer may be constructed to be flexible but stiff enough to withstand negative pressure, such that the loaded matrix is not collapsed excessively and thereby transmits negative pressure sufficiently to the wound when negative pressure is supplied to the wound dressing 300. The loaded matrix layer may be constructed to include sufficient number or size of pores to enable transmission of negative pressure through it. Further, the loaded matrix layer may have suitable thickness to transmit enough negative pressure to the wound. For example, the loaded matrix layer may have a thickness of 1 mm to 5 mm, 1.5 mm to 4 mm, or 2 mm to 3 mm. In some embodiments, the loaded matrix layer may have a thickness of approximately 2 mm.

Multi-Layered Wound Dressings for NPWT with an Obscuring Layer

FIG. 16A illustrates a cross-section through a wound dressing 2100 similar to the wound dressing of FIGS. 12A-12D according to an embodiment of the disclosure. The wound dressing 2100, which can alternatively be any wound dressing embodiment disclosed herein including without limitation wound dressing 110 or any combination of features of any number of wound dressing embodiments disclosed herein, can be located over a wound site to be treated. The dressing 2100 may be placed to as to form a sealed cavity over the wound site. In a preferred embodiment, the dressing 2100 comprises a backing layer 2140 attached to a wound contact layer 2102, similar to the cover layer and wound contact layer described with reference to FIGS. 12A-12D. These two layers 2140, 2102 are preferably joined or sealed together so as to define an interior space or chamber. This interior space or chamber may comprise additional structures that may be adapted to distribute or transmit negative pressure, store wound exudate and other fluids removed from the wound, and other functions as described herein. Examples of such structures, described below, include a transmission layer 2105 and an absorbent layer 2110, similar to the transmission layer and absorbent layer described with reference to FIGS. 12A-12D.

A layer 2105 of porous material can be located above the wound contact layer 2102. This porous layer, or transmission layer, 2105 allows transmission of fluid including liquid and gas away from a wound site into upper layers of the wound dressing. In particular, the transmission layer 2105 preferably ensures that an open-air channel can be maintained to communicate negative pressure over the wound area even when the absorbent layer has absorbed substantial amounts of exudates. The layer 2105 should preferably remain open under the typical pressures that will be applied during negative pressure wound therapy as described above, so that the whole wound site sees an equalized negative pressure.

In some embodiments, the layer 2105 may be formed of a material having a three-dimensional structure. For example, a knitted or woven spacer fabric (for example Baltex 7970 weft knitted polyester) or a non-woven fabric could be used.

A layer 2110 of absorbent material is provided above the transmission layer 2105. The absorbent material, which comprise a foam or non-woven natural or synthetic material, and which may optionally comprise a super-absorbent material, forms a reservoir for fluid, particularly liquid, removed from the wound site. In some embodiments, the layer 2100 may also aid in drawing fluids towards the backing layer 2140.

With reference to FIG. 16A, a masking or obscuring layer 2107 can be positioned beneath at least a portion of the backing layer 2140. In some embodiments, the obscuring layer 2107 can have any of the same features, materials, or other details of any of the other embodiments of the obscuring layers disclosed herein, including but not limited to having any viewing windows or holes. Examples of wound dressings with obscuring layers and viewing windows are described in International Patent Publication WO2014/020440, the entirety of which is incorporated by reference in its entirety. Additionally, the obscuring layer 2107 can be positioned adjacent to the backing layer, or can be positioned adjacent to any other dressing layer desired. In some embodiments, the obscuring layer 2107 can be adhered to or integrally formed with the backing layer. Preferably, the obscuring layer 2107 is configured to have approximately the same size and shape as the absorbent layer 2110 so as to overlay it. As such, in these embodiments the obscuring layer 2107 will be of a smaller area than the backing layer 2140.

The material of the absorbent layer 2110 may also prevent liquid collected in the wound dressing 2100 from flowing freely within the dressing, and preferably acts so as to contain any liquid collected within the absorbent layer 2110. The absorbent layer 2110 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 2110 may typically be manufactured from ALLEVYN™ foam, Freudenberg 114-224-4 and/or Chem-Posite™11C-450. In some embodiments, the absorbent layer 2110 may comprise a composite comprising superabsorbent powder, fibrous material such as cellulose, and bonding fibers. In a preferred embodiment, the composite is an air-laid, thermally-bonded composite.

An orifice 2144 is preferably provided in the backing layer 2140 to allow a negative pressure to be applied to the dressing 2100. A suction port 2150 is preferably attached or sealed to the top of the backing layer 2140 over an orifice 2144 made into the dressing 2100, and communicates negative pressure through the orifice 2144. A length of tubing may be coupled at a first end to the suction port 2150 and at a second end to a pump unit (not shown) to allow fluids to be pumped out of the dressing. The port may be adhered and sealed to the backing layer 2140 using an adhesive such as an acrylic, cyanoacrylate, epoxy, UV curable or hot melt adhesive. The port 2150 is formed from a soft polymer, for example a polyethylene, a polyvinyl chloride, a silicone or polyurethane having a hardness of 30 to 90 on the Shore A scale. In some embodiments, the port 2150 may be made from a soft or conformable material.

Preferably the absorbent layer 2110 and the obscuring layer 2107 include at least one through hole 2145 located so as to underlie the port 2150. Of course, the respective holes through these various layers 2107, 2140, and 2110 may be of different sizes with respect to each other. As illustrated in FIG. 16A a single through hole can be used to produce an opening underlying the port 2150. It will be appreciated that multiple openings could alternatively be utilized. Additionally, should more than one port be utilized according to certain embodiments of the present disclosure one or multiple openings may be made in the absorbent layer and the obscuring layer in registration with each respective port. Although not essential to certain embodiments of the present disclosure the use of through holes in the super-absorbent layer may provide a fluid flow pathway which remains unblocked in particular when the absorbent layer 2110 is near saturation.

The aperture or through-hole 2144 is preferably provided in the absorbent layer 2110 and the obscuring layer 2107 beneath the orifice 2144 such that the orifice is connected directly to the transmission layer 2105. This allows the negative pressure applied to the port 2150 to be communicated to the transmission layer 2105 without passing through the absorbent layer 2110. This ensures that the negative pressure applied to the wound site is not inhibited by the absorbent layer as it absorbs wound exudates. In other embodiments, no aperture may be provided in the absorbent layer 2110 and/or the obscuring layer 2107, or alternatively a plurality of apertures underlying the orifice 2144 may be provided.

The backing layer 2140 is preferably gas impermeable, but moisture vapor permeable, and can extend across the width of the wound dressing 2100. The backing layer 2140, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 2140 and a wound site where a negative pressure can be established. The backing layer 2140 is preferably sealed to the wound contact layer 2102 in a border region 2200 around the circumference of the dressing, ensuring that no air is drawn in through the border area, for example via adhesive or welding techniques. The backing layer 2140 protects the wound from external bacterial contamination (bacterial barrier) and allows liquid from wound exudates to be transferred through the layer and evaporated from the film outer surface. The backing layer 2140 preferably comprises two layers; a polyurethane film and an adhesive pattern spread onto the film. The polyurethane film is preferably moisture vapor permeable and may be manufactured from a material that has an increased water transmission rate when wet.

In some embodiments, the absorbent layer 2110 may be of a greater area than the transmission layer 2105, such that the absorbent layer overlaps the edges of the transmission layer 2105, thereby ensuring that the transmission layer does not contact the backing layer 2140. This provides an outer channel 2115 of the absorbent layer 2110 that is in direct contact with the wound contact layer 2102, which aids more rapid absorption of exudates to the absorbent layer. Furthermore, this outer channel 2115 ensures that no liquid is able to pool around the circumference of the wound cavity, which may otherwise seep through the seal around the perimeter of the dressing leading to the formation of leaks.

The wound dressings 2100 may incorporate or comprise a loaded matrix as hereinbefore described. For example, a loaded foam or fibre layer including a powder charge/additive as described previously herein and illustrated in FIGS. 1-10 may be incorporated into the wound dressing 2100. In some embodiments, the loaded matrix layer may be provided below the transmission layer 2105. In some embodiments, the loaded matrix layer may be provided above the wound contact layer 2102. In some embodiments, the loaded matrix layer may replace the transmission layer 2105, such that the loaded matrix layer is provided between an absorbent layer 2110 (described further below) and the wound contact layer 2102. In some embodiments, the loaded matrix layer may be the lowermost layer of the wound dressing 2100. The loaded matrix may have same or substantially similar size and shape with the transmission layer 2105 and/or the absorbent layer 2110. In some embodiments, the loaded matrix layer can supplement or replace the absorbent layer 2110, or the absorbent layer 2110 can be loaded with powder charge as described above.

The loaded matrix layer may be constructed to be flexible but stiff enough to withstand negative pressure, such that the loaded matrix is not collapsed excessively and thereby transmits negative pressure sufficiently to the wound when negative pressure is supplied to the wound dressing 2100. The loaded matrix layer may be constructed to include sufficient number or size of pores to enable transmission of negative pressure through it. Further, the loaded matrix layer may have suitable thickness to transmit enough negative pressure to the wound. For example, the loaded matrix layer may have a thickness of 1 mm to 5 mm, 1.5 mm to 4 mm, or 2 mm to 3 mm. In some embodiments, the loaded matrix layer may have a thickness of approximately 2 mm.

FIG. 16B illustrates a view of an embodiment of a wound dressing with a waisted portion, an obscuring layer, and viewing windows. FIG. 16B illustrates a perspective view of an embodiment of a wound dressing 1400. The wound dressing 1400 preferably comprises a port 1406. The port 1406 is preferably configured to be in fluid communication with a pump, and may include a tube or conduit pre-attached to the port. Alternatively, negative pressure can be supplied to the wound dressing through other suitable fluidic connectors, including but not limited to the fluidic connectors of the type described below in FIGS. 12A-12D.

The wound dressing 1400 can be constructed similar to the embodiments of FIG. 16A above, and may comprise an absorbent material 1402 underneath or within a backing layer 1405. Optionally, a wound contact layer and a transmission layer may also be provided as part of the wound dressing 1400 as described above with reference to FIG. 16A. The absorbent material 1402 can contain a narrowed central or waisted portion 1408 to increase flexibility and conformability of the wound dressing to the skin surface. The backing layer 1405 may have a border region 1401 that extends beyond the periphery of the absorbent material 1402. The backing layer 1405 may be a translucent or transparent backing layer, such that the border region 1401 created from the backing layer 1405 can be translucent or transparent. The area of the border region 1401 of the backing layer 405 can be approximately equal around the perimeter of the entire dressing with the exception of the narrowed central portion, where the area of the border region is larger. One will recognize that the size of the border region 1401 will depend on the full dimensions of the dressing and any other design choices.

As illustrated in FIG. 16B, provided at least at the top of or over the absorbent layer 1402 and under the backing layer 1405 may be an obscuring layer 1404 that optionally has one or more viewing windows 1403. The obscuring layer 1404 may partially or completely obscure contents (such as fluids) contained within the wound dressing 1400 and/or the absorbent material (i.e., within the absorbent material 1402 or under the backing layer 1405). The obscuring layer may be a colored portion of the absorbent material, or may be a separate layer that covers the absorbent material. In some embodiments, the absorbent material 1402 may be hidden (partially or completely), colored, or tinted, via the obscuring layer 1404, so as to provide cosmetic and/or aesthetic enhancements, in a similar manner to what is described above. The obscuring layer is preferably provided between the topmost backing layer 1405 and the absorbent material 1402, although other configurations are possible. The cross-sectional view in FIG. 16A illustrates this arrangement with respect to the masking or obscuring layer 2107. Other layers and other wound dressing components can be incorporated into the dressing as herein described.

The obscuring layer 1404 can be positioned at least partially over the absorbent material 1402. In some embodiments, the obscuring layer 1404 can be positioned adjacent to the backing layer, or can be positioned adjacent to any other dressing layer desired. In some embodiments, the obscuring layer 1404 can be adhered to or integrally formed with the backing layer and/or the absorbent material.

As illustrated in FIG. 16B, the obscuring layer 1404 can have substantially the same perimeter shape and size as the absorbent material 1402. The obscuring layer 1404 and absorbent material 1402 can be of equal size so that the entirety of the absorbent material 1402 can be obscured by the obscuring layer 1404. The obscuring layer 1404 may allow for obscuring of wound exudate, blood, or other matter released from a wound. Further, the obscuring layer 1404 can be completely or partially opaque having cut-out viewing windows or perforations.

In some embodiments, the obscuring layer 1404 can help to reduce the unsightly appearance of a dressing during use, by using materials that impart partial obscuring or masking of the dressing surface. The obscuring layer 1404 in one embodiment only partially obscures the dressing, to allow clinicians to access the information they require by observing the spread of exudate across the dressing surface. The partial masking nature of this embodiment of the obscuring layer enables a skilled clinician to perceive a different color caused by exudate, blood, by-products etc. in the dressing allowing for a visual assessment and monitoring of the extent of spread across the dressing. However, since the change in color of the dressing from its clean state to a state containing exudate is only a slight change, the patient is unlikely to notice any aesthetic difference. Reducing or eliminating a visual indicator of wound exudate from a patient's wound is likely to have a positive effect on their health, reducing stress for example.

In some embodiments, the obscuring layer can be formed from a non-woven fabric (for example, polypropylene), and may be thermally bonded using a diamond pattern with 19% bond area. In various embodiments, the obscuring layer can be hydrophobic or hydrophilic. Depending on the application, in some embodiments, a hydrophilic obscuring layer may provide added moisture vapor permeability. In some embodiments, however, hydrophobic obscuring layers may still provide sufficient moisture vapor permeability (i.e., through appropriate material selection, thickness of the obscuring layer), while also permitting better retention of dye or color in the obscuring layer. As such, dye or color may be trapped beneath the obscuring layer. In some embodiments, this may permit the obscuring layer to be colored in lighter colors or in white. In the preferred embodiment, the obscuring layer is hydrophobic. In some embodiments, the obscuring layer material can be sterilizable using ethylene oxide. Other embodiments may be sterilized using gamma irradiation, an electron beam, steam or other alternative sterilization methods. Additionally, in various embodiments the obscuring layer can colored or pigmented, e.g., in medical blue. The obscuring layer may also be constructed from multiple layers, including a colored layer laminated or fused to a stronger uncolored layer. Preferably, the obscuring layer is odorless and exhibits minimal shedding of fibers.

The absorbent layer 1402, itself may be colored or tinted in some embodiments, however, so that an obscuring layer is not necessary. The dressing may optionally include a means of partially obscuring the top surface. This could also be achieved using a textile (knitted, woven, or non-woven) layer without openings, provided it still enables fluid evaporation from the absorbent structure. It could also be achieved by printing an obscuring pattern on the top film, or on the top surface of the uppermost pad component, using an appropriate ink or colored pad component (yarn, thread, coating) respectively. Another way of achieving this would be to have a completely opaque top surface, which could be temporarily opened by the clinician for inspection of the dressing state (for example through a window), and closed again without compromising the environment of the wound. Additionally, FIG. 16B illustrates an embodiment of the wound dressing including one or more viewing windows 1403. The one or more viewing windows 1403 preferably extend through the obscuring layer 1404. These viewing windows 1403 may allow visualization by a clinician or patient of the wound exudate in the absorbent material below the obscuring layer. FIG. 16B illustrates an array of dots (e.g., in one or more parallel rows) that can serve as viewing windows 1403 in the obscuring layer 1404 of the wound dressing. In a preferred embodiment, two or more viewing windows 1403 may be parallel with one or more sides of the dressing 1400. In some embodiments, the one or more viewing windows may measure between 0.1 mm and 20 mm, preferably 0.4 mm to 10 mm, and even more preferably, 1 mm to 4 mm. The viewing windows 1403 may be cut through the obscuring layer 1404 or may be part of an uncolored area of the obscuring layer 1404 and therefore may allow visualization of the absorbent material 1402. The one or more viewing windows 1403 can be arranged in a repeating pattern across the obscuring layer 1404 or can be arranged at random across the obscuring layer. Additionally, the one or more viewing windows can be a circular shape or dots. Preferably, the one or more viewing windows 1403 are configured so as to permit not only the degree of saturation, but also the progression or spread of fluid toward the fluid port 1406, as in some embodiments, dressing performance may be adversely affected when the level of fluid has saturated the fluid proximate the port 1406. In some embodiments, a "starburst" array of viewing windows 1403 emanating around the port 1406 may be suitable to show this progression, although of course other configurations are possible. In some embodiments, the viewing windows 1403 correspond to the area of the absorbent material 1402 that is not covered by the obscuring layer 1404. As such, the absorbent material 1402 is directly adjacent the backing layer 1405 in this area. Since the obscuring layer 1404 acts as a partial obscuring layer, the viewing windows 1403 may be used by a clinician or other trained user to assess the spread of wound exudate throughout the dressing. In some embodiments, the viewing windows 1403 can comprise an array of dots or crescent shaped cut-outs. For example, an array of dots as viewing windows 1403 are illustrated in FIG. 16B in which the array of dots are arranged in an 5×2 array. Additionally, in some embodiments, the dot pattern can be distributed evenly throughout the obscuring layer and across the entire or substantially the entire surface of the obscuring layer. In some embodiments, the viewing windows 1403 may be distributed randomly throughout the obscuring layer. Preferably, the area of the obscuring layer 1404 uncovered by the one or more viewing windows 1403 is balanced to as to minimize the appearance of exudate while permitting the inspection of the dressing 1400 and/or absorbent material 1402. In some embodiments, the area exposed by the one or more viewing windows 1403 does not exceed 20% of the area of the obscuring layer 1404, preferably 10%, and even more preferably 5%.

The viewing windows 1403 may take several configurations. In some embodiments, the viewing windows 1403 may comprise an array of regularly spaced uncolored dots (holes) made into the obscuring layer 1404. While the dots illustrated here are in a particular pattern, the dots may be arranged in different configurations, or at random. The viewing windows 1403 are preferably configured so as to permit a patient or caregiver to ascertain the status of the absorbent layer, in particular to determine its saturation level, as well as the color of the exudate (e.g., whether excessive blood is present). By having one or more viewing windows, the status of the absorbent layer can be determined in an unobtrusive manner that is not aesthetically unpleasing to a patient. Because a large portion of the absorbent layer may be obscured, the total amount of exudate may therefore be hidden. As such, the status and saturation level of the absorbent layer 1402 may therefore present a more discreet external appearance so as to reduce patient embarrassment and visibility and thereby enhance patient comfort. In some configurations, the one or more viewing windows 1403 may be used to provide a numerical assessment of the degree of saturation of the dressing 1400. This may be done electronically (e.g., via a digital photograph assessment), or manually. For example, the degree of saturation may be monitored by counting the number of viewing windows 1403 which may be obscured or tinted by exudate or other wound fluids.

In some embodiments, the absorbent layer 1402 or the obscuring layer 1404, in particular the colored portion of the absorbent layer, may comprise (or be colored because of) the presence of an auxiliary compound. The auxiliary compound may in some embodiments be activated charcoal, which can act to absorb odors. The use of antimicrobial, antifungal, anti-inflammatory, and other such therapeutic compounds is also possible. In some embodiments, the color may change as a function of time (e.g., to indicate when the dressing needs to be changed), if the dressing is saturated, or if the dressing has absorbed a certain amount of a harmful substance (e.g., to indicate the presence of infectious agents). In some embodiments, the one or more viewing windows 1403 may be monitored electronically, and may be used in conjunction with a computer program or system to alert a patient or physician to the saturation level of the dressing 1400.

Multi-Layered Wound Dressing with a Support Layer

FIG. 17 shows an example of a multi-layer wound dressing 3100. The wound dressing 3100 includes a liquid impermeable film layer 3102 located at the top of the wound dressing 3100. In use, the film layer 3102 is the top layer of the wound dressing 3100, most distal from a wound site. The film layer 3102 is also gas and vapour permeable to allow for evaporation of fluid or wound exudate from the wound dressing 3100, and help prevent maceration of the wound. In this example, the film layer 3102 is formed from a polyurethane blend, though other suitable materials may include other polymeric materials, for example polyethylene, or polypropylene.

An absorbent layer 3108 underlies the film layer 3102. The absorbent layer 3108 has a fibrous structure for absorbing exudate from a wound site. In this example, the absorbent layer 3108 includes superabsorbent fibres. The absorbent layer 3108 also includes other fibres. In this example, the absorbent layer includes superabsorbent fibres, viscose fibres and polyester fibres. In this example, the absorbent layer 3108 includes around 40% superabsorbent fibres, 40% viscose fibres, and 20% polyester fibres. In other examples, the absorbent layer may include around 0-50% superabsorbent fibres, 0-100% viscose fibres and 0-50% polyester fibres. Suitable superabsorbent fibres include crosslinked acrylate copolymer fibres that are partially neutralized to sodium salt however other superabsorbent fibres are available. The absorbent layer 3108 may be manufactured using a needling process in which the fibres are mechanically tangled together. In other examples, the absorbent layer 3108 may include other ratios of superabsorbent, viscose and polyester fibres. For example, the absorbent layer may include around 50% superabsorbent fibres, 35% viscose fibres and 20% polyester fibres. Alternatively, the absorbent layer may include 40% superabsorbent fibres and 60% viscose fibres. The film layer 3102 is located over the absorbent layer 3108 so that wound exudate collected in the absorbent layer 3108 can evaporate out of the wound dressing 3100 through the film layer 3102.

A support layer 3106 is located between the film layer 3102 and the absorbent layer 3108. The support layer 3106 helps to reinforce the structure of the absorbent layer 3108 and thereby reduce shrinkage of the wound dressing 3100. The support layer 3102 also helps to provide extra mechanical strength to the film layer 3102 to reduce or prevent wrinkling of the film layer 3102 over time. The mechanical strength also reduces the chance of the dressing deforming or rolling up causing a pressure point. Aptly, the support layer 3106 is configured to have a tensile strength from 0.05 to 0.06 Nm to provide mechanical strength to the surrounding layers (e.g. the film layer 3102 and the absorbent layer 3108) without compromising the flexibility of the wound dressing 3100. The support layer 3106 may have a thickness of from 50 to 150 μm. Aptly, the support layer 3106 may have a thickness of around 100 to 110 μm.

The wound dressing 3100 may incorporate or comprise a loaded matrix as hereinbefore described. For example, a loaded foam or fibre layer including a powder charge/additive as described previously herein and illustrated in FIGS. 1-10 may be incorporated into the wound dressing 3100. In some embodiments, the loaded matrix layer may be provided below the cover layer 3102. In some embodiments, the loaded matrix layer may be provided below the absorbent layer 3108. In some embodiments, the loaded matrix layer may be the lowermost layer of the wound dressing 3100. The loaded foam may have same or substantially similar size or shape with the cover layer 3102 and/or the absorbent layer 3108. In some embodiments, the loaded matrix layer can supplement or replace the absorbent layer 3108, or the absorbent layer 3108 can be loaded with powder charge as described above.

Referring to FIG. 18, the support layer 3106 includes a net 3200 configured to reduce shrinkage of the wound dressing 3100. Aptly, the net 3200 is configured to reduce shrinkage of the absorbent layer 3108 and/or the film layer 3102 to help reduce wrinkling of the film layer 3102. In this example, the net 3200 has a substantially hexagonal (or honeycomb) structure 3204 including a plurality of substantially triangular shaped apertures 3202 extending therethrough. The hexagonal structure 3204 is formed from a plurality of dots (or bosses) 3206 joined by polymer strands 3208. The dots 3206 are substantially evenly spaced with respect to each other. Each dot forms a vertex of the hexagonal pattern in the structure 3204. Each dot 3206 is joined to six surrounding dots 3206 by polymer strands 3208. That is, six polymer strands 3208 extend from each dot 3206 and each connect to a respective surrounding dot 3206 to form the hexagonal structure 3204 having triangular shaped apertures 3202 between the polymer strands 3208. Each of the triangular shaped apertures 3202 may have an area A of from 0.005 to 0.32 $mm^2$. This allows liquid vapour from a wound to pass freely through the apertures, whilst still providing sufficient strength to the support layer 3106. It can also be said that the structure 3204 is a structure comprising a plurality of strands or struts that are joined to form a plurality of triangles. In this example the triangles tessellate in rows. It will be appreciated that the strands or struts may be arranged in other formations, for example squares, diamonds or rectangles with different geometries and therefore differing open areas.

In this example, the support layer 3106 is located directly adjacent the absorbent layer 3108. As such, the support layer 3106 can effectively provide additional mechanical strength to fibres in the top surface of the absorbent layer 3108. This can help prevent movement of the fibres and reduce shrinking of the absorbent layer 3108. Aptly, the support layer 3106 is bonded to the fibres in the top surface of the absorbent layer 3108. This can help to lock the fibres in position and prevent or reduce any movement. In this example, the support layer 3106 further includes a bonding layer for heat laminating the net 3200 to the absorbent layer 3108. The support layer 3106 is thus heat laminated to fibres in the absorbent layer 108 via the bonding layer.

The bonding layer contained within the net has a lower melting temperature than the net 3200 so that the support layer 3106 can be heat laminated to the absorbent layer 3108 whilst maintaining the structure of the net 3200. The bonding layer can be formed from a low melting point polymer, for example a low melting point ethylene-vinyl acetate, whilst the net 3200 may be formed from a high-density polyethylene, which melts at a higher temperature than the bonding layer. Other polymers having a lower melting point than the net 3200 may also be suitable. For example the bonding layer may be a separate layer or alternatively include an ethylene-acrylate or thermoplastic polyurethane based adhesive. The net 3200 and the bonding layer can be coextruded to form the support layer 3106. Aptly, the bonding layer is extruded with a similar structural shape to the net 3200, so that the apertures 3202 in the net 3200 are not obstructed by the bonding layer. This helps to ensure that exudate the absorbent layer 3108 can pass through the support layer and evaporate out of the wound dressing 3100 through the film layer 3102.

FIGS. 19A-B illustrate another example of a multi-layered wound dressing 3300. The wound dressing 3300 includes a film layer 3302, support layer 3306 and absorbent layer 3308, the same as the film layer 3102, support layer 3106 and absorbent layer 3108 described in relation to FIG. 17. The wound dressing 3300 also includes a first adhesive layer 3304, located between the film layer 3302 and the support layer 3306, for attaching the film layer 3302 to the support layer 3306. The first adhesive layer 3304 is a hot melt adhesive applied to a wound facing side (underside) of the film layer 3302. Aptly, the first adhesive layer 3304 is pattern coated onto the film layer 3302, to include holes, so that gas and liquid vapour can pass through holes in the first adhesive layer 3304. In other examples the film layer 3302 may be laminated (e.g. heat laminated) directly onto the support layer 3306 without the need for an adhesive layer 3304 in between. In this example, the wound dressing 3300 also includes a foam layer 3312, which is a fluid transport layer. The foam layer 3312 is located under the absorbent layer 3306. The foam layer 3312 acts to draw fluid away from a wound site and transport the fluid to the absorbent layer 3308. The foam layer may be formed from an open cell polyurethane foam and other options are available, as will be recognised by those skilled in the art.

An adhesive web layer 3310 is located between the foam layer 3312 and the absorbent layer 3108 to adhere the foam layer 3312 to the absorbent layer 3308. The adhesive web layer may be formed from bicomponent polypropylene/polyethylene fibres. Such bicomponent fibres are known in the art, so for brevity will not be discussed in detail. The adhesive web layer 3310 includes a plurality of apertures extending therethrough to allow for passage of exudate from the foam layer 3312 to the absorbent layer 3108.

The wound dressing 3300 also includes a wound contact layer 3320, which includes a perforated film 3316. The perforated film 3316 is located under the foam layer 3312 and helps to prevent the wound dressing 3100 from attaching to the wound as the wound heals. For example, where the wound dressing 3300 includes the foam layer 3112, the perforated film 316 can prevent new tissue from growing into cells of the foam layer 3312. In other examples, the foam layer 3312 may not be present and the perforated film 3316 can help prevent fibres of the absorbent layer 3308 from becoming embedded in the wound. Perforations in the perforated film 3316 are: aptly substantially uniformly distributed and are of suitable size to allow passage of exudate into the wound dressing 3300, e.g. with holes having a diameter of 1-2.5 mm. The perforated film 3316 is aptly formed from polyurethane. The wound contact layer 3320 may also include an adhesive 3318 located under the perforated film 3316 (i.e. on the wound facing side of the perforated film 3316) for adhering the wound dressing 3300 to the skin. In this case the adhesive is silicone 3318 and is aptly spread onto the underside of the perforated film with a coat weight of around 30-200 $g/m^2$. In some other examples, an additional attachment element, for example bandages, strips of tape, or compression bandages may be used to secure the wound dressing 3300 to the patient.

The top side of the perforated film 3316 (i.e. the side distal from the wound) may be coated with a further adhesive layer 3314. The further adhesive layer 3314 adheres the wound contact layer 3320 to the foam layer 3312. Aptly, the further adhesive layer 3314 may be an acrylic adhesive, though other suitable adhesives may also be used. In other examples the wound contact layer 3320 may be laminated (e.g. heat laminated) directly to the foam layer 3312, without the need for the further adhesive layer 3314 in between.

The wound dressing 3300 may incorporate or comprise a loaded matrix as hereinbefore described. For example, a loaded foam or fibre layer including a powder charge/additive as described previously herein and illustrated in FIGS. 1-10 may be incorporated into the wound dressing 3300. In some embodiments, the loaded matrix layer may be provided below the cover layer 3302. In some embodiments, the loaded matrix layer may be provided between the absorbent layer 3308 and the wound contact layer 3320. In some embodiments, the loaded matrix layer may be provided between the foam layer 3312 and the wound contact layer 3320, and thus adhered to the adhesive layer 3314. In some embodiments, the loaded matrix layer can supplement or replace the absorbent layer 3308 and/or foam layer 3312, or the absorbent layer 3308 and/or the foam layer 3312 can be loaded with powder charge as described above. The loaded matrix may have same or substantially similar size or shape with the cover layer 3302 and/or the absorbent layer 3308.

In another example, as shown in FIG. 20, the film layer 3502 may have a larger surface area than the remainder of the wound dressing 3500 so that it extends further outwardly than the other layers of the wound dressing. The wound-facing (underside) of the film layer may be coated with a pressure sensitive adhesive 3504 (or other suitable adhesive) for sticking the dressing to the patient around the wound periphery. The pressure sensitive adhesive 3504 may also adhere the film layer 3502 to the support layer 3506 of the wound dressing 3500. The wound dressing may also include an absorbent layer 3508, adhesive web layer 3510, foam layer 3512, further adhesive layer 3514 and wound contact layer 3520. Each of the layers in this example may be similar to corresponding layers described above in relation to FIGS. 19A and 19B, so for brevity will not be described again in detail.

In a further example, as shown in FIG. 21, both the wound contact layer 3620 and the film layer 3602 may extend beyond the remaining layers of the wound dressing 3600. The wound contact layer 3620 and the film layer may be adhered together around the periphery (e.g. via an adhesive layer 3604), so that the remaining layers of the wound dressing are sandwiched between the wound contact layer 3620 and the film layer 3602. In other words, the support layer 3606, the absorbent layer 3608, the adhesive web layer 3610, and the foam layer 3612 may be sealed within a cavity 3622 between the film layer 3602 and the wound contact layer 3620. In this example, a further adhesive layer 3614 adheres the foam layer 3612 to the wound contact layer 3620, though in other examples the further adhesive layer 614 may not be required. Each of the layers in this example may be similar to corresponding layers described above in relation to FIGS. 19A and 19B, so for brevity will not be described again in detail.

The wound dressing 3600 in this example may be manufactured similarly to the wound dressing 3300, but with the film layer 3602 and the wound contact layer 3620 being laminated together around the periphery (e.g. via the adhesive layer 3604) to sandwich the remaining layers between the film layer 3602 and the wound contact layer 620. Alternatively, the film layer 3602 may be directly laminated around the periphery (e.g. heat laminated) to the wound contact layer 3620, without the need for the additional adhesive layer 3604.

In similar fashion with the wound dressing 3300 described in relation to FIGS. 19A-19B, the wound dressings 3500 and 3600 may incorporate or comprise a loaded matrix as hereinbefore described. For example, a loaded foam or fibre layer including a powder charge/additive as described previously herein and illustrated in FIGS. 1-10 may be incorporated into the wound dressings 3500 and 3600. For example, the loaded matrix layer may be provided between the absorbent layer and the wound contact layer. In some embodiments, the loaded matrix layer may be provided between the foam layer and the wound contact layer, and thus adhered to the adhesive layer. In some embodiments, the loaded matrix layer can supplement or replace the absorbent layer 3508 and/or the foam layer 3512, or the absorbent layer 3508 and/or the foam layer 3512 can be loaded with powder charge as described above. The loaded foam may have same or substantially similar size or shape with the cover layer, the absorbent layer and/or the foam layer 3312.

Although the wound dressings 3300, 3500, 3600 have been described having several adhesive layers, one or more of these layers may not be present. For example, the perforated film itself may be formed from a hot melt adhesive material so that it can be directly heat laminated onto the foam layer, in which case the further adhesive layer may not be needed. In another example, the adhesive web layer may not be present if the foam and absorbent layers are adhered in another way. For example, the foam and absorbent layers may be directly chemically bonded together. Similarly, the first adhesive layer may not be needed. For example, if the support layer includes an adhesive material, or if the film layer itself is formed from a hot melt adhesive then the film layer and the support layer may be directly adhered together.

In another example, the wound dressing may be provided without the foam layer. The foam layer helps to transport exudate away from the wound. However in some cases, and depending on the severity of a wound, the absorbent layer may sufficiently draw exudate from the wound without the need for the foam layer.

Although in the examples described above, the support layer is heat laminated to the absorbent layer via a bonding layer, other laminating techniques may be suitable. For example, the bonding layer may include a pressure sensitive adhesive. In this case, heat may not be required to laminate the support layer and adhesive layer together.

Although in the example described above, the net layer has been described as having a substantially hexagonal shaped structure, other geometric structures may also be suitable. With other geometric structures, the apertures may also have different geometric shapes.

In another example, the wound dressing may include more than one support layer to provide support to other layers in the wound dressing. For example, a first support layer may be located between the liquid impermeable film layer and the absorbent layer, and a further support layer may be located between the absorbent layer and the fluid transport layer (foam layer). This may help to support the absorbent layer from both sides to further reduce shrinking of the absorbent layer.

Any of the examples described herein may be adapted for use with a negative pressure system (sometimes referred to as a reduced pressure system) including a source of negative pressure, such as a negative pressure pump. For example, the film layer may include a negative pressure interface, such as a port, to which a negative pressure supply tube may be connected. The supply tube may be connected to a negative pressure source so that, in use, the negative pressure source applies a negative pressure to the wound dressing between the film layer and the wound to help draw wound exudate away from the wound and into the absorbent layer of the dressing.

Terminology

Depending on the embodiment, certain operations, acts, events, or functions of any of the processes described herein can be performed in a different sequence, can be added, merged, or left out altogether (such as not all are necessary for the practice of the processes). Moreover, in certain embodiments, operations, acts, functions, or events can be performed concurrently, such as through multi-threaded processing, interrupt processing, or multiple processors or processor cores or on other parallel architectures, rather than sequentially.

The processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices. Likewise, the data repositories shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Any patents and applications and other references noted above, including any that may be listed in accompanying filing papers, are incorporated herein by reference. Aspects of the disclosure can be modified, if necessary, to employ the systems, functions, and concepts of the various references described herein to provide yet further implementations.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Any of the embodiments described herein can be used with a canister or without a canister. Any of the dressing embodiments described herein can absorb and store wound exudate.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

What is claimed is:

1. A flexible polyurethane (PU) material which comprises:

a flexible hydrophilic polyurethane foam porous matrix comprising two matrix faces and therebetween a structural matrix framework defining a network of cells, having a cell network surface and therein a network of pores; and a powder charge comprising at least two additives loaded in said structural matrix framework;

wherein said material is a foamed polymer produced from a system comprising an isocyanate prepolymer or monomer phase and an aqueous phase, wherein said system comprises one or more slurry phases or solid concentrates of said powder charge, or an insoluble portion thereof, in said isocyanate phase or part thereof;

wherein the powder charge retains solid form after polymerization of the flexible polyurethane material and the powder charge is homogeneously distributed within the flexible hydrophilic polyurethane foam porous matrix;

wherein a first additive comprises silver salt;

wherein a second additive comprises an absorbent additive that retains a capacity for aqueous absorption properties of the powder charge; and wherein the flexible polyurethane material provides an accumulated release of approximately 1.2 $mg/cm^2$ to 1.8 $mg/cm^2$ of the silver salt into 50 mL of aqueous media over a period of 7 days or more.

2. The flexible polyurethane material of claim 1, wherein the aqueous phase is selected from water and admixtures thereof with non-ionic surfactants selected from low molecular weight polyethylene glycol (PEG), oxypropylene-oxyethylene block copolymers and polyoxyethylene stearyl ether, and wherein the isocyanate phase comprises a polymerisable isocyanate-terminated prepolymer or monomer;

wherein the material is a hydrophilic foam, generated from hydrophilic isocyanate prepolymer comprising isocyanate selected from TDI and MDI and a polyol backbone selected from PEG and polypropylene glycol (PPG) of varying molecular weight or chain length.

3. The flexible polyurethane material of claim 1, wherein the first additive is insoluble or of very low solubility in said isocyanate phase.

4. The flexible polyurethane material of claim 1, wherein the first additive has a particle size on the order of 4 $\mu m < D50 < 60\ \mu m$.

5. The flexible polyurethane material of claim 1, wherein the first additive is selected from a group consisting of silver sulfadiazine, silver zeolite, silver sulfate, silver carbonate, silver chloride, silver nitrate, silver phosphate, silver citrate, silver acetate, silver lactate, and combinations thereof.

6. The flexible polyurethane material of claim 1, wherein the second additive comprises a super absorbent polymer (SAP).

7. The flexible polyurethane material of claim 6, wherein the super absorbent polymer is selected from a group consisting of sodium polyacrylate, carboxymethyl cellulose or cross linked carboxymethyl cellulose derivatives, cross linked polyethylene oxide, and PVA copolymer.

8. A method of treating a wound comprising:

placing the material of claim 1 into or over the wound;

wherein the powder charge is activated for release of an antimicrobial agent into the wound from the wound dressing upon contact with moist or aqueous medium.

9. The method of claim 8, additionally comprising securing the wound dressing in contact with said wound.

10. A method for manufacture of a flexible hydrophilic polyurethane foam porous matrix comprising two matrix faces and therebetween a structural matrix framework defining a network of cells, having a cell network surface and therein a network of pores and a powder charge comprising at least two additives loaded in said structural matrix framework, said method comprising:

providing an isocyanate phase and an aqueous phase making up a foamable polymerisable system;

providing one or more slurry phase or solid concentrate of said powder charge, or insoluble portion thereof, making up said isocyanate phase or part thereof; and intimately admixing said isocyanate phase and said aqueous phase with reaction and foaming thereof;

wherein the one or more slurry phase or solid concentrate makes up a part of one of said phases, said method comprises prior to, simultaneously with, or subsequent to admixing the other part thereof with the other phase thereof, or admixing said phases, combining the one or more slurry phase or solid concentrate with the other part thereof or with one or both of said phases;

wherein the powder charge retains solid form after polymerization of the flexible polyurethane material and the powder charge is homogeneously distributed within the flexible hydrophilic polyurethane foam porous matrix;

wherein a first additive comprises silver salt;

wherein a second additive comprises an absorbent additive that retains a capacity for aqueous absorption properties of the powder charge; and wherein the flexible polyurethane material provides an accumulated release of approximately 1.2 $mg/cm^2$ to 1.8 $mg/cm^2$ of the silver salt into 50 mL of aqueous media over a period of 7 days or more.

11. The method of claim 10, wherein the first additive has a particle size on the order of 4 $\mu m < D50 < 60\ \mu m$.

12. The method of claim 10, further comprising providing continuous flow and steady flow rate of isocyanate phase and aqueous phase in supply lines, and batchwise admixing at mixing head and casting at casting head, by provision of recirculation circuits for respective phases upstream of said mixing head wherein said slurry or solid concentrate of powder charge in a part of said isocyanate phase is provided intermittently to said mixing head or point upstream or downstream thereof without recirculation thereof or is provided in an independent recirculation circuit.

13. The method of claim 10, further comprising processing the first additive by drying or by particle size reduction prior to providing the powder charge in the slurry phase or solid concentrate.

14. The method of claim 10, wherein the slurry phase or solid concentrate comprises the powder charge in isocyanate and has a L.O.D less than 0.5%.

15. The method of claim 10, wherein the first additive is selected from a group consisting of silver sulfadiazine, silver zeolite, silver sulfate, silver carbonate, silver chloride, silver nitrate, silver phosphate, silver citrate, silver acetate, silver lactate, and combinations thereof.

16. The method of claim 10, wherein the homogeneous distribution of the first additive within the flexible hydrophilic polyurethane foam is formed by including the powder charge within the isocyanate phase prior to polymerization.

17. The method of claim 10, wherein said method is continuous and comprises dosing the slurry phase or solid concentrate to a 2-way mixing head with a stream of said isocyanate phase or part thereof;

or to a 2-way mixing head with a stream of said intimately admixed isocyanate phase or part thereof and aqueous phase or part thereof, or to a 3-way mixing head with respective streams of said isocyanate phase or part thereof and said aqueous phase or part thereof.

* * * * *